(12) United States Patent
Magnani et al.

(10) Patent No.: US 10,519,181 B2
(45) Date of Patent: Dec. 31, 2019

(54) HETEROBIFUNCTIONAL INHIBITORS OF E-SELECTINS AND CXCR4 CHEMOKINE RECEPTORS

(71) Applicant: GlycoMimetics, Inc., Rockville, MD (US)

(72) Inventors: John L. Magnani, Gaithersburg, MD (US); Arun K. Sarkar, North Potomac, MD (US); John M. Peterson, Slate Hill, NY (US)

(73) Assignee: GLYCOMIMETICS, INC., Rockville, MD (US)

( * ) Notice: Subject to any disclaimer, the term of this patent is extended or adjusted under 35 U.S.C. 154(b) by 131 days.

(21) Appl. No.: 15/531,951

(22) PCT Filed: Dec. 1, 2015

(86) PCT No.: PCT/US2015/063191
§ 371 (c)(1),
(2) Date: May 31, 2017

(87) PCT Pub. No.: WO2016/089872
PCT Pub. Date: Jun. 9, 2016

(65) Prior Publication Data
US 2017/0305951 A1    Oct. 26, 2017

Related U.S. Application Data

(60) Provisional application No. 62/087,085, filed on Dec. 3, 2014.

(51) Int. Cl.
*C07H 15/26* (2006.01)
*C07H 15/207* (2006.01)
*C07H 3/06* (2006.01)

(52) U.S. Cl.
CPC .............. *C07H 15/26* (2013.01); *C07H 3/06* (2013.01); *C07H 15/207* (2013.01)

(58) Field of Classification Search
None
See application file for complete search history.

(56) References Cited

U.S. PATENT DOCUMENTS

| | | |
|---|---|---|
| 4,471,057 A | 9/1984 | Koprowski et al. |
| 4,851,511 A | 7/1989 | Hakomori et al. |
| 4,859,769 A | 8/1989 | Karlsson et al. |
| 4,876,199 A | 10/1989 | Hakamori |
| 4,925,796 A | 5/1990 | Bergh et al. |
| 4,946,830 A | 8/1990 | Pulverer et al. |
| 5,143,712 A | 9/1992 | Brandley et al. |
| 5,151,360 A | 9/1992 | Handa et al. |
| 5,211,937 A | 5/1993 | Brandley et al. |
| 5,268,364 A | 12/1993 | Kojima et al. |
| 5,304,640 A | 4/1994 | Lasky et al. |
| 5,352,670 A | 10/1994 | Venot et al. |
| 5,369,096 A | 11/1994 | Yamada et al. |
| 5,412,123 A | 5/1995 | Rao et al. |
| 5,444,050 A | 8/1995 | Kogan et al. |
| 5,464,778 A | 11/1995 | Cummings et al. |
| 5,464,815 A | 11/1995 | Chamow et al. |
| 5,470,843 A | 11/1995 | Stahl et al. |
| 5,484,891 A | 1/1996 | Lasky et al. |
| 5,486,536 A | 1/1996 | Ward et al. |
| 5,519,008 A | 5/1996 | Rao et al. |
| 5,527,785 A | 6/1996 | Bevilacqua et al. |
| 5,538,724 A | 7/1996 | Butcher et al. |
| 5,559,103 A | 9/1996 | Gaeta et al. |
| 5,576,305 A | 11/1996 | Ratcliffe |
| 5,580,858 A | 12/1996 | Ippolito et al. |
| 5,580,862 A | 12/1996 | Rosen et al. |
| 5,589,465 A | 12/1996 | Ishida et al. |
| 5,604,207 A | 2/1997 | DeFrees et al. |
| 5,618,785 A | 4/1997 | Heavner et al. |
| 5,622,937 A | 4/1997 | Kogan et al. |
| 5,632,991 A | 5/1997 | Gimbrone, Jr. |
| 5,639,734 A | 6/1997 | Esko et al. |
| 5,646,123 A | 7/1997 | Ippolito et al. |
| 5,646,248 A | 7/1997 | Sawada et al. |
| 5,648,344 A | 7/1997 | Brandley et al. |
| 5,654,282 A | 8/1997 | Tang et al. |
| 5,654,412 A | 8/1997 | Srivastava et al. |

(Continued)

FOREIGN PATENT DOCUMENTS

| | | |
|---|---|---|
| DE | 2434953 | 2/1975 |
| EP | 319253 A2 | 6/1989 |

(Continued)

OTHER PUBLICATIONS

Wolff, Manfred E. "Burger's Medicinal Chemistry, 5ed, Part I", John Wiley & Sons, 1995, pp. 975-977 (Year: 1995).*
Banker, G.S. et al, "Modern Pharmaceutics, 3ed.", Marcel Dekker, New York, 1996, p. 451 (Year: 1996).*
Abraham, W.M. et al., "Selectin Blockade Prevents Antigen-induced Late Bronchial Response and Airway Hyperresponsiveness in Allergic Sheep," Am J. Respir Crit Care Med. 159: 1205-1214, 1999.
Acord, J. et al., "A rapid microplate method for quantifying inhibition of bacterial adhesion to eukaryotic cells," Journal of Microbiological Methods 60: 55-62, 2005.

(Continued)

*Primary Examiner* — Traviss C McIntosh, III
(74) *Attorney, Agent, or Firm* — Finnegan, Henderson, Farabow, Garrett & Dunner LLP

(57) ABSTRACT

Compounds, compositions, and methods for treatment and/or prevention of cancer and inflammatory diseases, and for releasing cells such as stem cells (e.g., bone marrow progenitor cells) into circulating blood and enhancing retention of the cells in the blood are disclosed. For example, heterobifunctional compounds that inhibit both E-selectins and CXCR4 chemokine receptors are described and pharmaceutical compositions comprising at least one of the same.

31 Claims, 11 Drawing Sheets

(56) References Cited

U.S. PATENT DOCUMENTS

| | | |
|---|---|---|
| 5,658,880 A | 8/1997 | Dasgupta et al. |
| 5,663,151 A | 9/1997 | Martel et al. |
| 5,679,321 A | 10/1997 | Dasgupta et al. |
| 5,679,644 A | 10/1997 | Rao et al. |
| 5,686,426 A | 11/1997 | Martel et al. |
| 5,693,621 A | 12/1997 | Toepfer et al. |
| 5,695,752 A | 12/1997 | Rosen et al. |
| 5,710,023 A | 1/1998 | Collins et al. |
| 5,710,123 A | 1/1998 | Heavner et al. |
| 5,723,583 A | 3/1998 | Seed et al. |
| 5,728,685 A | 3/1998 | Abbas et al. |
| 5,739,300 A | 4/1998 | Toepfer et al. |
| 5,747,463 A | 5/1998 | Marinier et al. |
| 5,750,508 A | 5/1998 | Dasgupta et al. |
| 5,753,617 A | 5/1998 | Heavner et al. |
| 5,753,631 A | 5/1998 | Paulson et al. |
| 5,763,413 A | 6/1998 | Numata et al. |
| 5,763,582 A | 6/1998 | Rao et al. |
| 5,789,385 A | 8/1998 | Anderson et al. |
| 5,789,573 A | 8/1998 | Baker et al. |
| 5,795,958 A | 8/1998 | Rao et al. |
| 5,811,404 A | 9/1998 | De Frees et al. |
| 5,811,405 A | 9/1998 | Toepfer et al. |
| 5,817,742 A | 10/1998 | Toepfer et al. |
| 5,817,807 A | 10/1998 | Bridger et al. |
| 5,827,817 A | 10/1998 | Larsen et al. |
| 5,827,837 A | 10/1998 | Bevilacqua et al. |
| 5,830,871 A | 11/1998 | Wong et al. |
| 5,837,689 A | 11/1998 | Anderson et al. |
| 5,837,690 A | 11/1998 | Rao et al. |
| 5,840,679 A | 11/1998 | Larsen et al. |
| 5,854,218 A | 12/1998 | DeFrees |
| 5,856,300 A | 1/1999 | Rittershaus et al. |
| 5,858,983 A | 1/1999 | Seed et al. |
| 5,858,994 A | 1/1999 | Kretzschmar et al. |
| 5,880,091 A | 3/1999 | Cummings et al. |
| 5,916,910 A | 6/1999 | Lai |
| 5,919,768 A | 7/1999 | Korgan et al. |
| 5,919,769 A | 7/1999 | Tsukida et al. |
| 5,962,422 A | 10/1999 | Nagy et al. |
| 5,976,540 A | 11/1999 | Rittershaus et al. |
| 5,977,080 A | 11/1999 | Rosen et al. |
| 5,985,852 A | 11/1999 | Nagy et al. |
| 5,994,402 A | 11/1999 | Rotstein et al. |
| 6,001,819 A | 12/1999 | Simon et al. |
| 6,001,988 A | 12/1999 | Parma et al. |
| 6,033,665 A | 3/2000 | Yednock et al. |
| 6,037,333 A | 3/2000 | Panjwani |
| 6,043,348 A | 3/2000 | Lawman et al. |
| 6,110,897 A | 8/2000 | Unverzagt et al. |
| 6,111,065 A | 8/2000 | Heavner et al. |
| 6,120,751 A | 9/2000 | Unger |
| 6,121,233 A | 9/2000 | Magnani et al. |
| 6,124,267 A | 9/2000 | McEver et al. |
| 6,133,239 A | 10/2000 | Handa et al. |
| 6,133,240 A | 10/2000 | Taylor et al. |
| 6,136,790 A | 10/2000 | Toepfer et al. |
| 6,169,077 B1 | 1/2001 | Oehrlein |
| 6,177,547 B1 | 1/2001 | Cummings et al. |
| 6,187,754 B1 | 2/2001 | Oehrlein |
| 6,193,973 B1 | 2/2001 | Tuttle |
| 6,193,979 B1 | 2/2001 | Rittershaus et al. |
| 6,197,752 B1 | 3/2001 | Schmidt et al. |
| 6,225,071 B1 | 5/2001 | Cummings et al. |
| 6,235,309 B1 | 5/2001 | Nagy et al. |
| 6,280,932 B1 | 8/2001 | Parma et al. |
| 6,287,556 B1 | 9/2001 | Portnoy et al. |
| 6,309,639 B1 | 10/2001 | Cummings et al. |
| 6,372,712 B1 | 4/2002 | Briesewitz |
| 6,387,884 B1 | 5/2002 | Magnani et al. |
| 6,391,857 B1 | 5/2002 | Magnani et al. |
| 6,407,135 B1 | 6/2002 | Lai et al. |
| 6,465,434 B1 | 10/2002 | Magnani et al. |
| 6,492,332 B1 | 10/2002 | Demopulos et al. |
| 6,503,885 B1 | 1/2003 | Kiso et al. |
| 6,506,770 B1 | 1/2003 | Bridger et al. |
| 6,515,117 B2 | 2/2003 | Ellsworth et al. |
| 6,528,487 B1 | 3/2003 | Heavner et al. |
| 6,569,998 B2 | 5/2003 | Cummings et al. |
| 6,592,872 B1 | 7/2003 | Klimpel et al. |
| 6,683,056 B2 | 1/2004 | Washburn et al. |
| 6,756,391 B2 | 6/2004 | Bridger et al. |
| 6,844,125 B2 | 1/2005 | Bistrup et al. |
| 6,872,714 B1 | 3/2005 | Schols |
| 6,875,738 B1 | 4/2005 | Clark-Lewis et al. |
| 6,887,842 B1 | 5/2005 | Briesewitz |
| 6,921,531 B2 | 7/2005 | Briesewitz |
| 6,943,239 B2 | 9/2005 | Holgersson et al. |
| 6,967,093 B2 | 11/2005 | Bistrup et al. |
| 7,060,685 B2 | 6/2006 | Magnani et al. |
| 7,087,212 B2 | 8/2006 | Cantrell et al. |
| 7,160,872 B2 | 1/2007 | Bridger et al. |
| 7,226,949 B2 | 6/2007 | Crooks et al. |
| 7,300,656 B2 | 11/2007 | Ashkenazi et al. |
| 7,361,644 B2 | 4/2008 | Magnani et al. |
| 7,390,784 B2 | 6/2008 | Briesowitz |
| 7,414,065 B2 | 8/2008 | Bridger et al. |
| 7,422,733 B2 | 9/2008 | Ranganathan et al. |
| 7,449,176 B2 | 11/2008 | Ashkenazi et al. |
| 7,517,980 B2 | 4/2009 | Magnani et al. |
| 7,563,760 B2 | 7/2009 | Larsen et al. |
| 7,709,486 B2 | 5/2010 | Bridger et al. |
| 7,728,117 B2 | 6/2010 | Magnani et al. |
| 7,741,312 B2 | 6/2010 | Magnani et al. |
| 7,951,816 B2 | 5/2011 | Kokubo et al. |
| 7,964,569 B2 | 6/2011 | Ernst et al. |
| 7,989,601 B2 | 8/2011 | Magnani et al. |
| 8,026,222 B2 | 9/2011 | Magnani et al. |
| 8,039,442 B2 | 10/2011 | Magnani |
| 8,258,290 B2 | 9/2012 | Magnani et al. |
| 8,361,975 B2 | 1/2013 | Magnani |
| 8,410,066 B2 * | 4/2013 | Magnani ............ A61K 31/7034 514/35 |
| 8,518,896 B2 | 8/2013 | Magnani et al. |
| 8,530,448 B2 | 9/2013 | Magnani et al. |
| 8,633,303 B2 | 1/2014 | Magnani et al. |
| RE44,778 E | 2/2014 | Magnani et al. |
| 8,895,510 B2 | 11/2014 | Magnani |
| 8,921,328 B2 | 12/2014 | Ernst et al. |
| 9,109,002 B2 | 8/2015 | Magnani et al. |
| 9,254,322 B2 | 2/2016 | Levesque et al. |
| 9,486,497 B2 | 11/2016 | Levesque et al. |
| 9,534,009 B2 | 1/2017 | Magnani |
| 2001/0046970 A1 | 11/2001 | Nagy et al. |
| 2001/0051370 A1 | 12/2001 | Bistrup et al. |
| 2002/0031508 A1 | 3/2002 | Wagner et al. |
| 2002/0040008 A1 | 4/2002 | Wagner et al. |
| 2002/0086356 A1 | 7/2002 | Tuschi et al. |
| 2002/0128225 A1 | 9/2002 | Liu et al. |
| 2002/0132220 A1 | 9/2002 | Berens et al. |
| 2002/0155429 A1 | 10/2002 | Allaway et al. |
| 2002/0164336 A1 | 11/2002 | Harrison et al. |
| 2002/0164748 A1 | 11/2002 | Bistrup et al. |
| 2002/0165178 A1 | 11/2002 | Schetter et al. |
| 2002/0168366 A1 | 11/2002 | Stewart et al. |
| 2003/0012787 A1 | 1/2003 | Ashkenazi et al. |
| 2003/0012790 A1 | 1/2003 | Ashkenazi et al. |
| 2003/0018181 A1 | 1/2003 | Larsen et al. |
| 2003/0036560 A1 | 2/2003 | Sonis et al. |
| 2003/0039683 A1 | 2/2003 | Cantrell et al. |
| 2003/0073632 A1 | 4/2003 | Ciacci et al. |
| 2003/0211078 A1 | 11/2003 | Heavner |
| 2004/0067220 A1 | 4/2004 | Sykes |
| 2004/0072796 A1 | 4/2004 | Embury et al. |
| 2004/0096396 A1 | 5/2004 | Magnani et al. |
| 2004/0097403 A1 | 5/2004 | Ranganathan et al. |
| 2004/0219158 A1 | 11/2004 | Magnani |
| 2005/0112124 A1 | 5/2005 | Frenette et al. |
| 2005/0181987 A1 | 8/2005 | Blaszczyk-Thurin et al. |
| 2005/0187171 A1 | 8/2005 | Magnani et al. |
| 2005/0214283 A1 | 9/2005 | Sackstein et al. |
| 2006/0194745 A1 | 8/2006 | Magnani et al. |
| 2006/0217303 A1 | 9/2006 | Kriegler |
| 2006/0264451 A1 | 11/2006 | Shim et al. |

(56) References Cited

U.S. PATENT DOCUMENTS

| | | |
|---|---|---|
| 2006/0287253 A1 | 12/2006 | Kriegler et al. |
| 2007/0021378 A1 | 1/2007 | Varki et al. |
| 2007/0054870 A1 | 3/2007 | Magnani et al. |
| 2007/0054930 A1 | 3/2007 | Shim et al. |
| 2007/0213278 A1 | 9/2007 | Wong et al. |
| 2008/0025992 A1 | 1/2008 | Fabene et al. |
| 2008/0112955 A1 | 5/2008 | Embury et al. |
| 2008/0161546 A1 | 7/2008 | Ernst et al. |
| 2008/0200406 A1 | 8/2008 | Magnani |
| 2008/0227799 A1 | 9/2008 | Liotta et al. |
| 2008/0300220 A1 | 12/2008 | Ranganathan et al. |
| 2008/0306098 A1 | 12/2008 | Mutz et al. |
| 2009/0036386 A1 | 2/2009 | Magnani et al. |
| 2009/0053198 A1 | 2/2009 | Sackstein |
| 2009/0054334 A1 | 2/2009 | Mutz et al. |
| 2009/0175792 A1 | 7/2009 | Magnani et al. |
| 2009/0176717 A1 | 7/2009 | Magnani |
| 2009/0253646 A1 | 10/2009 | Magnani |
| 2009/0312278 A1 | 12/2009 | Magnani et al. |
| 2010/0145032 A1 | 6/2010 | Laine et al. |
| 2010/0215575 A1 | 8/2010 | O'Neill et al. |
| 2010/0240773 A1 | 9/2010 | Korzekwa et al. |
| 2010/0292095 A1 | 11/2010 | Laukkanen et al. |
| 2010/0303766 A1 | 12/2010 | Miyaji et al. |
| 2010/0311105 A1 | 12/2010 | Lu et al. |
| 2011/0002881 A1 | 1/2011 | Levesque et al. |
| 2011/0020270 A1 | 1/2011 | Levesque et al. |
| 2011/0142856 A1 | 6/2011 | Kokubo et al. |
| 2011/0229409 A1 | 9/2011 | Ranganathan et al. |
| 2011/0245265 A1 | 10/2011 | Zuk et al. |
| 2011/0251148 A1 | 10/2011 | Magnani et al. |
| 2011/0257380 A1 | 10/2011 | Ernst et al. |
| 2012/0093782 A1 | 4/2012 | Grove et al. |
| 2012/0129712 A1 | 5/2012 | Satomaa et al. |
| 2012/0202762 A1 | 8/2012 | Magnani |
| 2012/0258043 A1 | 10/2012 | Ranganathan et al. |
| 2012/0329755 A1 | 12/2012 | Magnani et al. |
| 2013/0184229 A1* | 7/2013 | Magnani ............ A61K 31/7034 514/35 |
| 2013/0261070 A1 | 10/2013 | Magnani et al. |
| 2013/0281646 A1 | 10/2013 | Korzekwa et al. |
| 2013/0331350 A1 | 12/2013 | Ernst et al. |
| 2014/0073594 A1 | 3/2014 | Magnani et al. |
| 2014/0178303 A1 | 6/2014 | Magnani et al. |
| 2015/0051164 A1 | 2/2015 | Magnani |
| 2015/0110808 A1 | 4/2015 | Magnani et al. |
| 2015/0284420 A1 | 10/2015 | Magnani et al. |
| 2016/0145290 A1 | 5/2016 | Magnani et al. |
| 2016/0184339 A1 | 6/2016 | Magnani |
| 2016/0193294 A1 | 7/2016 | Magnani et al. |
| 2016/0243145 A1 | 8/2016 | Magnani et al. |
| 2016/0289257 A1 | 10/2016 | Magnani et al. |
| 2016/0333043 A1 | 11/2016 | Magnani et al. |

FOREIGN PATENT DOCUMENTS

| | | |
|---|---|---|
| EP | 381310 A1 | 8/1990 |
| EP | 408859 B1 | 1/1991 |
| EP | 671407 A2 | 9/1995 |
| EP | 0 867 722 | 9/1998 |
| JP | 06-0306092 | 11/1994 |
| JP | 9-176047 | 7/1997 |
| JP | 2002-520323 | 7/2002 |
| JP | 2004-518704 | 6/2004 |
| JP | 2009-507031 | 2/2009 |
| WO | WO 90/13300 | 11/1990 |
| WO | WO 91/19502 | 12/1991 |
| WO | WO 92/01718 | 2/1992 |
| WO | WO 92/07572 | 5/1992 |
| WO | WO 94/25043 | 11/1994 |
| WO | WO 94/26760 | 11/1994 |
| WO | WO 94/29477 | 12/1994 |
| WO | WO 95/00527 | 1/1995 |
| WO | WO 95/03059 | 2/1995 |
| WO | WO 95/29681 | 11/1995 |
| WO | WO 95/31210 | 11/1995 |
| WO | WO 96/20204 | 7/1996 |
| WO | WO 96/25418 | 8/1996 |
| WO | WO 96/26950 | 9/1996 |
| WO | WO 96/40942 | 12/1996 |
| WO | WO 97/01335 | 1/1997 |
| WO | WO 97/01569 | 1/1997 |
| WO | WO 97/14707 | 4/1997 |
| WO | WO 97/28173 | 8/1997 |
| WO | WO 97/28174 | 8/1997 |
| WO | WO 98/06730 | 2/1998 |
| WO | WO 98/13058 | 4/1998 |
| WO | WO 98/046771 | 10/1998 |
| WO | WO 99/42130 | 8/1999 |
| WO | WO 99/43353 | 9/1999 |
| WO | WO 99/43356 | 9/1999 |
| WO | WO 99/065712 | 12/1999 |
| WO | WO 00/02870 | 1/2000 |
| WO | WO 00/050032 | 8/2000 |
| WO | WO 00/066112 | 11/2000 |
| WO | WO 01/89564 | 11/2001 |
| WO | WO 02/22820 | 3/2002 |
| WO | WO 02/062810 | 8/2002 |
| WO | WO 03/032925 | 4/2003 |
| WO | WO 03/055876 | 7/2003 |
| WO | WO 03/088980 | 10/2003 |
| WO | WO 03/097658 | 11/2003 |
| WO | WO 04/004636 | 1/2004 |
| WO | WO 04/033663 | 4/2004 |
| WO | WO 04/058304 | 7/2004 |
| WO | WO 04/094619 | 11/2004 |
| WO | WO 05/016349 | 2/2005 |
| WO | WO 05/046597 | 5/2005 |
| WO | WO 05/051920 | 6/2005 |
| WO | WO 05/054264 | 6/2005 |
| WO | WO 05/058934 | 6/2005 |
| WO | WO 05/085219 | 9/2005 |
| WO | WO 05/116088 | 12/2005 |
| WO | WO 06/017180 | 2/2006 |
| WO | WO 06/022454 | 3/2006 |
| WO | WO 06/062946 | 6/2006 |
| WO | WO 06/074426 | 7/2006 |
| WO | WO 06/074428 | 7/2006 |
| WO | WO 06/089106 | 8/2006 |
| WO | WO 06/127906 | 11/2006 |
| WO | WO 07/021721 | 2/2007 |
| WO | WO 07/022089 | 2/2007 |
| WO | WO 07/022385 | 2/2007 |
| WO | WO 07/028050 | 3/2007 |
| WO | WO 07/033329 | 3/2007 |
| WO | WO 08/008852 | 1/2008 |
| WO | WO 08/008854 | 1/2008 |
| WO | WO 08/011094 | 1/2008 |
| WO | WO 08/060378 | 5/2008 |
| WO | WO 08/100453 | 8/2008 |
| WO | WO 08/109154 | 9/2008 |
| WO | WO 09/011889 | 1/2009 |
| WO | WO 09/073911 | 6/2009 |
| WO | WO 09/073916 | 6/2009 |
| WO | WO 09/126556 | 10/2009 |
| WO | WO 09/152245 | 12/2009 |
| WO | WO 10/126888 | 11/2010 |
| WO | WO 12/037034 | 3/2012 |
| WO | WO 12/045913 | 4/2012 |
| WO | WO 12/061662 | 5/2012 |
| WO | WO 12/151576 | 11/2012 |
| WO | WO 13/096926 | 6/2013 |
| WO | WO 14/070991 | 5/2014 |
| WO | WO 14/149837 | 9/2014 |
| WO | WO 15/048616 | 4/2015 |
| WO | WO 05/046997 | 5/2015 |
| WO | WO 15/109049 | 7/2015 |
| WO | WO 16/089872 | 6/2016 |

(56) References Cited

FOREIGN PATENT DOCUMENTS

| WO | WO 16/164394 | 10/2016 |
|---|---|---|
| WO | WO 17/095904 | 6/2017 |

OTHER PUBLICATIONS

Adams, E. W. et al., "Oligosaccharide and Glycoprotein Microarrays as Tools in HIV Glycobiology: Glycan-Dependent gp120/Protein Interactions," Chemistry & Biology 11:875-881, Jun. 2004.
Aggoune et al., "The Vascular Niche Is Involved in Regulating Leukemic Stem Cells in Murine Chronic Myelogenous Leukemia" Blood, 124(21):516, Dec. 6, 2014.
Alessandro, et al., "Role of S128R polymorphism of E-selectin in colon metastasis formation," Int. J. Cancer, 121(3): 528-535 (2007).
Ali, M., et al., "Polymers bearing sLex-mimetics are superior inhibitors of E-selectin-dependent leukocyte rolling in vivo", The FASEB Journal 18(1), (2004), 152-154.
Alousi, A., et al., "Reduced-Intensity Conditioning Allogeneic Hematopoietic Stem Cell Transplantation", Clinical Advances in Hematoloav & Oncoloav. 5(7), (2007), 560-570.
Arakaki, R. et al., "T134, a Small-Molecule CXCR4 Inhibitor, Has No Cross-Drug Resistance with AMD3100, a CXCR4 Antagonist with a Different Structure," Journal of Virology 73(2):1719-1723, Feb. 1999.
Arshad, S. et al., "Primary prevention of asthma and allergy," J. Allergy Clin. Immunol., 116: 3-14 (2005).
Arshad, S. et al., "Primary prevention of asthma and atopy during childhood by allergen avoidance in infacny: a randomised controlled study," Thorax., 58:489-493 (2003).
Astronomo, R.D. et al., "A Glycoconjugate Antigen Based on the Recognition Motif of a Broadly Neutralizing Human Immunodeficiency Virus Antibody, 2G12, Is Immunogenic but Elicits Antibodies Unable to Bind to the Self Glycans of gp120," Journal of Virology 82(13):6359-6368, Jul. 2008.
Azab et al, "Role of Selectins in the Pathogenesis of Multiple Myeloma", ASCO Annual Meeting 2009, Poster #11103, May 2009.
Azab et al., "P-selectin Glycoprotein Ligand Regulates the Interaction of Multiple Myeloma Cells with the Bone Marrow Microenvironment", Blood, 119:1468-1478, Nov. 16, 2011.
Azab et al., "Role of Selectins in the Pathogenesis of Multiple Myeloma", J Clin Oncol, 27(15s):absrt 11103, 2009.
Baeckstrom et al., "Purification and Characterization of a Membrane-bound and a Secreted Mucin-type Glycoprotein Carrying the Carcinoma-associated Sialyl-Le.sup.a Epitope on Distinct Core Proteins," J. Biol. Chem. 266(32):21537-21547, 1991.
Banteli et al., "Synthesis of sialyl lewisx mimics. Modifications of the 6-position of galactose," Bioorganic & Medicinal Chemistry Letters, 11(4): 459-462 (2001).
Banteli, R. et al., "Potent E-Selectin Antagonists," Helvetica Chimica Acta 83(11): 2893-2907, 2000.
Barasch et al., "Palifermin for Management of Treatment-Induced Oral Mucositis in Cancer Patients", Biologics: Targets & Therapy, 3:111-116, 2009.
Barnes, P. et al., "How do corticosteroids work in asthma?" Ann. Intern. Med., 139: 359-370 (2003).
Bastin, R.. et al,"Salt Selection and Optimisation Procedures for Pharmaceutical New Chemical Entities" Organic Process Research & Development (2000), vol. 4, pp. 427-435.
Bedard et al., "Expert Opinion: Selectin Inhibitors: A Patent Review," Rights Link, 20(6):781-793, 2010.
Belcher, J.D. et al., "Activated monocytes in sickle cell disease: potential role in the activation of vascular endothelium and vaso-occlusion," Blood 96(7):2451-2459, Oct. 1, 2000.
Belcher, J.D. et al., "Inflammatory response in transgenic mouse models of human sickle cell anemia," Blood 96(11)Pt. 1 :600a, Abstract #2574, Nov. 16, 2000.
Bennett, C. F., et al., "Inhibition of Endothelial Cell Adhesion Molecule Expression with Antisense Oligonucleotides", Journal of Immunoloav. 152(7), (1994), 3530-3540.
Berg et al., "A Carbohydrate Domain Common to Both Sialyl Le.sup.a and Sialyl Le.sup.x Is Recognized by the Endothelial Cell Leukocyte Adhesion Molecule ELAM-1," J. Biol. Chem. 266(23):14869-14872, 1991.
Berg et al., "The Cutaneous Lymphocyte Antigen Is a Skin Lymphocyte Homing Receptor for the Vascular Lectin Endothelial Cell-Leukocyte Adhesion Molecule 1," J. Exp. Med. 174:1461-1466, 1991.
Berger et al., "Adoptive transfer of effector CD8+ T cells derived from central memory cells establishes persistent T cell memory in primates." J. Clin. Invest. 118(1):294-305 (2008).
Bevilacqua, et al., "Endothelial-leukocyte adhesion molecules in human disease," Ann. Rev. Med., 45: 361-378 (1994).
Bhaskar, V. et al. "E-selectin Up-regulation Allows for Targeted Drug Delivery in Prostrate Cancer," Cancer Research, 63: 6387-6394 (Oct. 2003).
Bird and Kimber, "Oligosaccharides Containing Fucose Linked .alpha.(1-3) and .alpha.(1-4) to N-Acetylglucosamine Cause Decompaction of Mouse Morulae," Devel. Biol. 104:449-460, 1984.
Bjercke,"Rational Design and Synthesis of Oligosaccharide Mimetics: Selectin Antagonists as Cell Adhesion Inhibitors," Abstracts of Papers, 210th ACS National Meeting, American Chemical Society, Chicago, IL, Aug. 20-24, 1995, MEDI-18.
Blanc-Muesser et al., "Syntheses Stereoselective de 1-Thioglycosides," Carbohydrate Research 67:305-328, 1978, and English Translation.
Bochner, B. et al., "Glycan array screening reveals a candidate ligand for Siglec-8," Journal of Biological Chemistry, 280(6): 4307-4312 (2005).
Bock, K. et al., "Conformations in Solution of a, a-Trehalose, a-D-Glucopyranosyl a-D-Mannopyranoside, and Their 1-Thioglycosyl Analogs, and a Tentative Correlation of Their Behaviour with Respect to the Enzyme Trehalase," European Journal of Biochemistry, 131:595-600, 1983.
Bogden, A. E., et al., "Amelioration of Chemotherapy-Induced Toxicity by Cotreatment with AcSDKP, a Tetrapeptide Inhibitor of Hematopoietic Stem Cell Proliferation", Annals New York Academy of Sciences. 628, (1991), 126-139.
Bowen et al., "Characterization of a Human Homologue of the Murine Peripheral Lymph Node Homing Receptor," Journal of Cell Biology, 109:421-427, 1989.
Bradford, G. B., et al., "Quiescence, cycling, and turnover in the primitive hematopoietic stem cell compartment", Experimental Hematoloav. 25, (1997), 445-453.
Brandley et al., "Carbohydrate Ligands of LEC Cell Adhesion Molecules," Cell, 63:861-863, 1990.
Bridger, GJ et al. "Synthesis and Structure—Activity Relationships of Phenylenebis(methylene)-Linked Bis-Tetraazamacrocycles That Inhibit HIV Replication. Effects of Macrocyclic Ring Size and Substituents on the Aromatic Linker," J. Med. Chem., 38: 366-378 (1995).
Brodt et al., "Liver endothelial E-selectin mediates carcinoma cell adhesion and promotes liver metastasis," Int. J. Cancer, 71(4): 612-619 (1997).
Broquet et al., "Effect of Desipramine on a Glycoprotein Sialyltransferase Activity in C6 Cultured Glioma Cells," J. Neurochem., 54:388-394, 1990.
Burkhardt, K., et al., "The Significance of Adhesion Molecules in Nephrology", Artificial Oraans 20(5), (1996), 433-436.
Calarese, D. A. et al., "Antibody Domain Exchange is and Immunological Solution to Carbohydrate Cluster Recognition," Science 300:2065-2071, Jun. 2003.
Calarese, D. A. et al., "Dissection of the Carbohydrate Specificity of the Broadly Neutralizing Anti-HIV-1 Antibody 2G12," Proceedings of the National Academy of Sciences 102(38):13372-13377, Sep. 2005.
Cao, X. et al., "Defective Lymphoid Development in Mice Lacking Expression of the Common Cytokine Receptor Y Chain," Immunity, 2:223-238, Mar. 1995.
Ceder, O. et al., "On the Absolute Configuration of3-Cyclohexene-I-carboxylic Acid," Acta Chemica Scandivavica, 24(8):2693-2698, 1970.

(56) References Cited

OTHER PUBLICATIONS

Chang et al., "Effects of Pan-Selectin Antagonist GMI-1070 on the Treatment of Vaso-Occlusion in Sickle Cell Mice", Blood, 112(11), Abstract #535, Nov. 2008.

Chang, J. et al. "GMI-1070, a novel pan-selectin antagonist, reverses acute vascular occlusions in sickle cell mice," Blood, 116(10): 1779-1786 (Sep. 2010).

Chase et al., "E-Selectin Ligands as Mechanosensitive Receptors on Neutrophils in Health and Disease", Annals of Biomedical Engineering, DOI:10.1007/s10439-011-0507-y, Jan. 24, 2012.

Chemical Abstracts (STN), Accession No. 1997:584307, Jul. 8, 1997.

Chien et al., "A Novel Small Molecule E-Selectin Inhibitor GMI-1271 Blocks Adhesion of AML Blasts to E-Selectin and Mobilizes Blood Cells in Nodscid IL2Rgc-/- Mice Engrafted with Human AML", Blood, 120(21), Abstract #4092, Nov. 16, 2012.

Chien et al., "A Novel Small Molecule E-Selectin Inhibitor GMI-1271 Blocks Adhesion of AML Blasts to E-Selectin and Mobilizes Blood Cells in Nodscid IL2Rgc-/- Mice Engrafted with Human AML", 2012 ASH Annual Meeting, Poster #54715, Dec. 10, 2012.

Chien et al., "Adhesion of Acute Myeloid Leukemia Blasts to E-Selectin in the Vascular Niche Enhances Their Survival by Mechanisms Such as Wnt Activation", Blood, 122(21):61, Nov. 15, 2013.

Chien et al., "Novel Dual E-Selectin-CXCR4 Inhibitors Mobilize Human Acute Myeloid Leukemia (AML) Cells in the NODscid IL2R{gamma}c-/- Xenograft and Confer Susceptibility to Cytarabine", Blood, 118(21), Abstract #579, Nov. 18, 2011.

Childs et al. ,"High-molecular-weight glycoproteins are the major carriers of the carbohydrate differentiation antigens I, I and SSEA-1 of mouse teratocarcinoma cells," Biochem. J., 215:491-503 (1983).

Choi, S. et al., "Synthetic Multivalent Molecules: Concepts and Biomedical Applications," Wiley-Interscience, p. xxi-xxvi, 1-17, 2004.

Christianson, S.W. et al.,"Enhanced Human CD4+ T Cell Engraftment in ß2-Microglobulin-Deficient NOD-scid Mice," The Journal of Immunology, 158:3578-3586 (1997).

Cleophax, J. et al., "A chiral synthesis of D-(+)-2,6-dideoxystreptamine and its microbial incorporation into novel antibodies," Journal of the American Chemical Society, 98 (22): 7110-7112 (Oct. 27, 1976).

Collier, et al., "Membrane translocation by anthrax toxin," Molecular Aspects of Medicine, 30(6): 413-422 (Dec. 1, 2009).

Corral et al., "Requirements for Sialic Acid on Neutrophils in a GMP-140 (PADGEM) Mediated Adhesive Interaction with Activated Platelets," Biochem. Biophys. Res. Commun., 172:1349-1356, (1990).

Corson, Timothy W. et al., "Design and Applications of Bifunctional Small Molecules: Why Two Heads Are Better Than One," ACS Chemical Biology 3(11):677-692, Nov. 2008.

Cottler-Fox, M.H. et al., "Stem Cell Mobilization," Amer. Sci. Hematology, 419-437, (2003).

Crawford et al., "AMD070, a CXCR4 Chemokine Receptor Antagonist: Practical Large-Scale Laboratory Synthesis," Org. Process Res. Devel. 12:823-830, 2008.

Cumpstey, I. et al. "C2-Symmetrical Thiodigalactoside Bis-Benzamido Derivatives as High-Affinity Inhibitors of Galectin-3: Efficient Lectin Inhibition through Double Arginine—Arene Interactions," Angew Chem., 117:5240-5242 (2005).

Dagia, Nilesh et al., "G-CSF induces E-selecting ligand expression on human myeloid cells," Nature Medicine, 12(10): 1185-90, Oct. 1, 2006.

Daoudii, Jean-Michel et al., "New bicyclam-GalCer analogue conjugates: synthesis and in vitro anti-HIV activity," Bioorg. & Med. Chem. Letters 14:495-498, 2004.

Datta and Takayama, "Isolation and purification of trehalose 6-mono- and 6,6'-di-corynomycolates from Cornyebacterium matruchotii. Structural characterization of $^1H$ NMR," Carbohydrate Research 245: 151-158, 1993.

De Clercq, Erik, "The bicyclam AMD3100 story," Nat. Rev. Drug Disc. 2:581-587, Jul. 2003.

Decastro et al., "Effects of GMI-1070, a Pan-Selectin Inhibitor, On Pain Intensity and Opioid Utilization in Sickle Cell Disease", Blood, 122(21):775, Nov. 15, 2013.

Definition of allogenic. Medline Plus-Merriam-Webster Medical Dictionary (last accessed Jun. 3, 2013).

Definition of syngeneic. Medline Plus-Merriam-Webster Medical Dictionary (last accessed Jun. 3, 2013).

Definition of xenogeneic. Medline Plus-Merriam-Webster Medical Dictionary (last accessed Jun. 3, 2013).

Demain et al. "Natural products for cancer chemotherapy," Microbio. Biotechnol. 4(6): 687-699, 2011.

Devereux, J., et al., "A comprehensive set of sequence analysis programs for the VAX", Nucleic Acids Research 12(1), (1984), 387-395.

Devine, "Rapid Mobilization of CD34+ Cells Following Administration of the CXCR4 Antagonist AMD 3100 to Patients With Multiple Myeloma and Non-Hodgkin's Lymphoma," Journal of Clinical Oncology, 22(6): 1095-1102 (Feb. 23, 2004).

Deweerdt, "Animal models: Towards a myeloma mouse," Nature, 480 (7377): S38-39 (2011).

Diamandis et al., "Reflection on the Discovery of Carcinoembryonic Antigen, Prostate-Specific Antigen, and Cancer Antigens CA125 and CA19-9", Clin Chem, 59(1), Nov. 30, 2012.

Diaz-Ricart et al., "rPSGL-Ig" Drugs of the Future 27(4):346 (2002).

Dittmar, Thomas et al., "Adhesion Molecules and Chemokines: the Navigation System for Circulating Tumor (Stem) Cells to Metastasize in an Organ-Specific Manner," Clin. Exp. Metastasis 25:11-32, 2008.

Doranz, B.J. et al., "Safe Use of the CSCR4 Inhibitor ALX40-4C in Humans," AIDS Research and Human Retroviruses 17(6):475-486, 2001.

Duijvestijn et al., "High Endothelial Differentiation in Human Lymphoid and Inflammatory Tissues Defined by Monoclonal Antibody HECA-452," Am. J. Path. 130:147-155, 1988.

Dupre, B. et al., "Glycomimetic Selectin Inhibitors: (.alpha.-D-Mannopyranosyloxy)methylbiphenyls," Bioorganic & Medicinal Chemistry Letters 6(5): 569-572, 1996.

Dutta P. et al "E-selectin inhibition mitigates splenic HSC activation and myelopoiesis in hypercholesterolemic mice with myocardial infarction highlights" Arteriosclerosis, Thrombosis, and Vascular Biology 36(9):1802-08 (2016).

Dykewicz, C. "Summary of the Guidelines for Preventing Opportunistic Infections among Hematopoietic Stem Cell Transplant Recipients," Clin. Infectious Diseases, 33:139-144, Jul. 15, 2001.

Edgington, "How Sweet It Is: Selectin-Mediating Drugs," Biotechnology 10: 383-389, 1992.

Edwards, W. Barry et al., "Generally Applicable, Convenient Solid-Phase Synthesis and Receptor Affinities of Octreotide Analogs," J. Med. Chem. 37:3749-3757, 1994.

Egberink, H. et al. "Bicyclams, Selective Antagonists of the Human Chemokine Receptor CXCR4, Potently Inhibit Feline Immunodeficiency Virus Replication," Journal of Virology, 73(8): 6346-6352 (1999).

Eggens et al., "A Role of Carbohydrate-Carbohydrate Interaction in the Process of Specific Cell Recognition During Embryogenesis and Organogenesis: A Preliminary Note," Biochem. Biophys. Res. Commun. 158(3):913-920, 1989.

Eggens et al., "Specific Interaction between Le.sup.X and Le.sup.X Determinants. A Possible Basis for Cell Recognition in Preimplantation Embryos and in Embryonal Carcinoma Cells," J. Biol. Chem. 264(16):9476-9484, 1989.

Egger, J. et al. "Nanomolar E-Selectin Antagonists with Prolonged Half-Lives by a Fragment-Based Approach," JACS, 135(26): 9820-9828 (Jul. 2013).

Embury, S.H. et al., "The contribution of endothelial cell P-selectin to the microvascular flow of mouse sickle erythrocytes in vivo," Blood 104(10):3378-3385, Nov. 15, 2004.

English Abstract for DE 2434953, Feb. 6, 1975.

English Abstract for JP 9-176047, published Jul. 8, 1997.

English Abstract for WO 96/20204, published Jul. 4, 1996.

(56) References Cited

OTHER PUBLICATIONS

English Translation of JP 06-0306092, dated Nov. 1, 1994.
Ernst and Oehrlein, "Substrate and donor specificity of glycosyl transferases," Glycoconjugate Journal 16: 161-170, 1999.
Ernst B. et al., "Design and Synthesis of E-Selectin Antagonists," Chimia 55:268-274, 2001.
Ernst, B. et al., "From carbohydrate leads to glycomimetic drugs," Nature Reviews 8:661-677, Aug. 2009.
Esposito et al., "Exploration of a Potent E-selectin Antagonist (GMI-1271) as a Potential Therapeutic for Treating Breast Cancer Metastasis to the Lung and Bone", AACR Annual Meeting 2014, Poster #4039, Apr. 8, 2014.
Esposito et al., "Exploration of a Potent E-selectin Antagonist (GMI-1271) as a Potential Therapeutic for Treating Breast Cancer Metastasis to the Lung and Bone", Cancer Res, Abstract #4039, Oct. 1, 2014.
Faber et al., "The Many Facets of SDF-1a, CXCR4 Agonists and Antagonists on Hematopoietic Progenitor Cells," J. Biomed. & Biotech. Article ID 26065:1-10, 2007.
Feletou, M. et al., "Endothelial dysfunction: a multifaceted disorder," Am. J. Physiol. Heart Circ. Physiol., 291: H985-H1002 (2006).
Fenderson et al., "A Multivalent Lacto-N-Fucopenataose III-Lysyllysine Conjugate Decompacts Preimplantation Mouse Embryos, While the Free Oligosaccharide is Ineffective," J. Exp. Med. 160:1591-1596, 1984.
Fenderson et al., "Coordinate Expression of X and Y Haptens during Murine Embryogenesis," Devel. Biol. 114:12-21, 1986.
Fenderson et al., "The blood group I antigen defined by monoclonal antibody C6 is a marker of early mesoderm during murine embryogenesis," Differentiation 38:124-133, 1988.
Filser, C. et al., "Synthetic glycopeptides from the E-selectin ligand 1 with varied sialyl Lewis(x) structure as cell-adhesion inhibitors of E-selectin," Angewandte Chemie—International Edition, 46(12): 2108-2111 (2007).
Flanner et al., "Comparison of Predicted GMI-1070 Human Intravenous Pharmacokinetics from in silico PBPK and Allometric Scaling Models", AAPS Annual Meeting, Abstract, Nov. 2009.
Frenette, Paul S. et al., "Sulfated Glycans Induce Rapid Hematopoietic Progenitor Cell Mobilization: Evidence for Selectin-Dependent and Independent Mechanisms," Blood, 96:2460-2468, (2000).
Frison, N. et al., "Oligolysine-Based Oligosaccharide Clusters: Selective Recognition and Endocytosis by the Mannose Receptor and Dendritic Cell-Specific Intercellular Adhesion Molecule 3 (ICAM-3)-Grabbing Nonintegrin," The Journal of Biological Chemistry 278(26):23922-23929, Apr. 2003.
Fruehauf, S., et al., "Protection of hematopoietic stem cells from chemotherapy-induced toxicity by multidrug-resistance 1 gene transfer," Recent Results in Cancer Research, 144, Abstract Only), (1998), 1 pQ.
Fukushi et al., "Novel Fucolipids Accumulating in Human Adenocarcinoma," J. Biol. Chem. 259(16):10511-10517 (1984).
Fukushi et al., "Novel Fucolipids Accumulating in Human Adenocarcinoma. II. Selective Isolation of Hybridoma Antibodies That Differentially Recognize Mono-, Di-, and Trifucosylated Type 2 Chain," J. Biol. Chem. 259(7):4681-4685, 1984.
Gabius et al., "Endogenous Tumor Lectins: Overview and Perspectives," Anticancer Res. 6:573-578, 1986.
Gats, H.-J. et al., "Enantioselective and Enantioconvergent Syntheses of Building Blocks for the Total Synthesis of Cyclopentanoid Natural Products," Angewandte Chemie, Int. Ed. Eng. 23(2):142-143, 1984.
Gallatin et al., "A cell-surface molecule involved in organ-specific homing of lymphocytes," Nature 304:30-34, 1983.
Garber, N. et al., "On the specificity of the D-galactose-binding lectin (PA-I) of Pseudomonas aeruginosa and its strong binding to hydrophobic derivatives of D-galactose and thiogalactose," Biochimica et Biophysica Acta, 1116:331-333 (1992).
Gelbrich, T. et al., "Preparation of 4-benzylsulfanyl[1,2,3,5]dithiadiazol-1-ylium chlorides: potential precursors to meso-ionic 1,2,3,5-dithiadiazolium-4-thiolate," Arkivoc, (vi): 224-223 (2002).
Ghobrial, IM, "Myeloma as a model for the process of metastasis: implications for therapy," 120(1): 20-30 (2012).
Gilboa-Gardner, N. et al., "A new mitogenic D-galactosephilic lectin isolated from seeds of the coral-tree Erythrina corallodendron. Comparison with Glycine max (soybean) and Pseudomonas aeruginosa lectins," Canadian Journal of Biochemistry, 59(5):315-320 (1981).
Goodman and Gillman's, "Pharmacological Basis of Therapeutics," 10th edition, p. 54 (2001).
Gooi et al., "Stage-specific embryonic antigen involves alpha 1—3 fucosylated type 2 blood group chains," Nature 292:156-158, 1981.
Gout, et al., "Selectins and selectin ligands in extravasation of cancer cells and organ selectivity of metastasis," Clin. Exp. Metastasis, 25(4): 335-344 (2008).
Hakomori et al., "Novel Fucolipids Accumulating in Human Adenocarcinoma. I. Glycolipids With Di-or Trifucosylated Type 2 Chain," J. Biol. Chem. 259(7):4672-4680, 1984.
Hakomori et al., "The Hapten Structure of a Developmentally Regulated Glycolipid Antigen (SSEA-1) Isolated From Human Erythrocytes and Adenocarcinoma: A Preliminary Note," Biochem. Biophys. Res. Comm. 100(4):1578-1586, 1981.
Hakomori S., "Aberrant Glycosylation in Cancer Cell Membranes as Focused on Glycolipids: Overview and Perspectives," Cancer Res. 45:2405-2414, 1985.
Halloran, M. et al., "Ley/H: An endothelial-selective cytokine-inducible angiogenic mediator," Journal of Immunology, 164(9): 4868-4877 (May 1, 2000).
Hamamoto, N., et al., "Inhibition of Dextram Sulphat Sodium (DSS)-induced Colitis in Mice by Intracolonically Administered Antibodies Against Adhesion Molecules (Endothelial Leucocyte Adhesion Molecule-1 (ELAM-1) or Intercellular Adhesion Molecule-1 (ICAM-1))", Clinical ExperimentalImmunoloqv, 117, (1999), 462-468.
Handa et al., "Selectin GMP-140 (CD62; PADGEM) Binds to Sialosyl-Le$^a$ and Sialosyl-Le$^x$, and Sulfated Glycans Modulate this Binding," Biochemical and Biophysical Research Communication 181(3):1223-1230, 1991.
Handschel J. et al., "Irradiation induces increase of adhesion molecules and accumulation of beta2-integrin-expressing cells in humans" International Journal of Radiation Oncology, Biology, Physics 45(2): 475-481 (1999).
Hansson and Zopf, "Biosynthesis of the Cancer-associated Sialyl-Le.sup.a Antigen," Journal of Biological Chemistry 260(16):9388-9392, 1985.
Harlan, J.M., "Introduction-anti-adhesion therapy in sickle cell disease," Blood 95:365-367, 2000.
Hasegawa et al., "Synthesis of deoxy-L-fucose-containing sialyl Lewis X ganglioside analogues," Carbohydrate Research 257: 67-80, 1994.
Hasegawa et al., "Synthesis of sialyl Lewis X ganglioside analogues containing modified L-fucose residues," Carbohydrate Research 274: 165-181, 1995.
Hebbel, P.R., "Blockade of Adhesion of Sickle Cells to Endothelium by Monoclonal Antibodies," The New England Journal of Medicine 342:1910-1912, Jun. 22, 2000.
Hendrix, C.W. et al., "Pharmacokinetics and Safety of AMD-3100, a Novel Antagonist of the CXCR-4 Chemokine Receptor, in Human Volunteers," Antimicrobial Agents and Chemotherapy 44(6):1667-1673, Jun. 2000.
Hilal et al., "Electronic structure of orotic acid I. Geometry, conformational preference and tautomerism:, Journal of Molecular Structure (Theochem)" 685 (2004) 35-42.
Hilgenbrink, A. et al., "Folate receptor-mediated drug targeting: from therapeutics to diagnostics," J. Pharm. Sci., 94(10): 2135-2146 (2005).
Holgate, ST et al., "Epithelium dysfunction in asthma," Current Reviews of Allergy and Clinical Immunology, 120: 1233-1234 (2007).
Holmes et al., "Enzymatic Basis for the Accumulation of Glycolipids with X and Dimeric X Determinants in Human Lung Cancer Cells (NCI-H69)," J. Biol. Chem. 260(12):7619-7627, 1985.

(56) References Cited

OTHER PUBLICATIONS

Hong, P. W.-P. et al., "Identification of the Optimal DC-SIGN Binding Site on Human Immunodeficiency Virus Type 1 gp120," Journal of Virology 18(15):8325-8336, Aug. 2007.
Huse et al., "Generation of a Large Combinatorial Library of the Immunoglobulin Repertoire in Phage Lambda," Science 246:1275-1281, 1989.
Huwe, C. M. et al., "Design, Synthesis and Biological Evaluation of Aryl-substituted Sialyl Lewis X Mimetics Prepared Via Cross-metathesis of C-Fucopeptides," Biological & Medicinal Chemistry 7:773-788, 1999.
Hynes, R., "Integrins: A Family of Cell Surface Receptors," Cell 48:549-554, 1987.
Ikeuchi, Yoshihiro et al., "Synthesis and Antitumor Activities of Novel 5-Deazaflavin-Sialic Acid Conjugate Molecules," Bioorg. & Med. Chem. 8:2027-2035, 2000.
International Search Report for PCT/US2015/063191 dated Mar. 1, 2016.
Inwald, D. P. et al., "Platelet and leucocyte activation in childhood sickle cell disease: association with nocturnal hypoxaemia," British Journal of Haematology! 11:474-481, Nov. 2000.
Ishikawa, F. et al., "Chemotherapy-resistant human AML stem cells home to and engraft within the bone-marrow endosteal region," Nature Biotechnology 25(11):1315-1321, Nov. 2007.
Issekutz, T., "Inhibition of in Vivo Lymphocyte Migration of Inflammation and Homing to Lymphoid Tissues by the TA-2 Monoclonal Antibody. A Likely Role for VLA-4 in Vivo," Journal of Immunology 147:4178-4184, 1991.
Itai, S. et al., "Differentiation-dependent Expression of I and Sialyl I Antigens in the Developing Lung of Human Embryos and in Lung Cancers," Cancer Research 50: 7603-7611, 1990.
Jeffrey et al., "Affinity Chromatography of Carbohydrate-Specific Immunoglobulins: Coupling of Oligosaccharides to Sepharose ," Biochem. Biophys. Res. Commun. 62:608-613, 1975.
Jentsch, K.D. et al., "Inhibition of Human Immunodeficiency Virus Type I Reverse Transcriptase by Suramin-related Compounds," The Journal of General Virology 68(8): 2183-2192, 1987.
Jentsch, TJ et al. "Ion Channels: Function Unravelled by Dysfunction," Nature Cell Biology, 6(11): 1039-1047 (Nov. 2004).
Kaila, N. et al., "Design and synthesis of sialyl Lewis(x) mimics as E- and P-selectin inhibitors," Med Res Rev 22(6):566-601, Nov. 2002.
Kaila, N. et al., "ß-C-Mannosides as Selectin Inhibitors," Journal of Medicinal Chemistry 45(8): 1563-1566, 2002.
Kannagi et al., "New Globoseries Glycosphingolipids in Human Teratocarcinoma Reactive with the Monoclonal Antibody Directed to a Developmentally Regulated Antigen, Stage-specific Embryonic Antigen 3," J. Biol. Chem. 258(14):8934-8942, 1983.
Kannagi et al., "Stage-specific embryonic antigens (SSEA-3 and -4) are epitopes of a unique globo-series ganglioside isolated from human teratocarcinoma cells," Embo J. 2(12):2355-2361, 1983.
Kannagi, R. et al. "Carbohydrate-mediated cell adhesion in cancer metastasis and angiogenesis," Cancer Sci., 95(5): 377-384 (2004).
Kansas, G., "Selectins and Their Ligands: Current Concepts and Controversies," Blood, 88(9): 3259-3287 (1996).
Karaivanova et al., "Partial Characterization of Microsomal Sialyltransferase From Chicken Liver and Hepatoma Mc-29: II. Measurement of Enzyme Activities Utilizing Microsomal Glycoproteins as Exogenous Acceptors," Cancer Biochem. Biophys. 11:311-315, 1990.
Katayama, Y. et al., "PSGL-1 Participates in E-Selectin-Mediated Progenitor Homing to Bone Marrow: Evidence for Cooperation Between E-Selectin Ligands and a4 Integrin," Blood, 102:2060-2067, (2003).
Katayama, Y., et al., "CD 44 is a physiological E-selectin ligand on neutrophils", J. Exp. Med. 201(8), (2005), 1183-1189.
Kaul, D.K. et al., "Hypoxia/reoxygenation causes inflammatory response in transgenic sickle mice but not in normal mice," The Journal of Clinical Investigation 106(3):411-420, Aug. 2000.

Khatib, A.-M., et al., "Inhibition of Hepatic Endothelial E-Selectin Expression by C-raf antisense Oligonucleotides Blocks Colorectal Carcinoma Liver Metastasis", Cancer Research 62(19), (2002), 5393-5398.
Kiel, M. J., et al., "SLAM Family Receptors Distinguish Hematopoietic Stem and Progenitor Cells and Reveal Endothelial Niches for Stem Cells" Cell 121 (7) (2006), 11 09-1121.
Kilgore K. S. et al., "Reducation of myocardial infarct size in vivo by carbohydrate-based glycomimetics" Journal of Pharmacology and Experimental Therapeutics, American Society for Pharmacology and Experimental Therapeutics, 284(1):427-435 (1998).
Kim et al., "Inhibition of the CXCR4/CXCL12 Chemokine Pathway Reduces the Development of Murine Pulmonary Metastases," Clin. Exp. Metastasis 25(3):201-211, 2008.
Kitagawa et al., "Characterization of Mucin-Type Oligosaccharides With the Sialyl-Le.sup.a Structure From Human Colorectal Adenocarcinoma Cells," Biochem. Biophys. Res. Commun. 178(3):1429-1436, 1991.
Kitagawa et al., "Immunoaffinity Isolation of a Sialyl-Le$^a$ Oligosaccharide from Human Milk," J. Biochem. 104:591-594, 1988.
Kneuer et al: "Selectins—potential pharmacological targets?" Drug Discovery Today vol. 11, No. 21-22, pp. 1034-1040, Oct. 2006.
Ko, HL et al. "In Vitro and In Vivo Inhibition of Lectin Mediated Adhesion of Pseudomonas aeruginosa by Receptor Blocking Carbohydrates," Infection, 15(4): 21-24 (1987).
Koch, Alisa E et al., "Angiogenesis mediated by soluble forms of E-selectin and vascular cell adhesion molecule-1," Nature, 376(6540): 517-519 (1995).
Koenig et al., "Selectin Inhibition: Synthesis and Evaluation of Novel Sialylated, Sulfated and Fucosylated Oligosaccharides, Including the Major Capping Group of Glycam-1", Glycobiology, 7(1):79-93 (1997).
Kogan, T.P. et al., "Novel Synthetic Inhibitors of Selectin-Mediated Cell Adhesion: Synthesis of 1,6-Bis[3-(3-carboxymethylphenyl)-r-(2-.alpha.-.sub.D-monnopyranosyloxy)p- henyl]hexane (TBC1269)," J Med. Chem 41:1099-1111, 1998.
Kogan, T.P. et al., "Rational Design and Synthesis of Oligosaccharide Mimetics: Selectin Antagonists as Cell Adhesion Inhibitors," Abstracts of Papers, 210.sup.th ACS National Meeting, American Chemical Society, Chicago, IL, Aug. 20-24, 1995, MEDI-18.
Kogan, T.P. et al., "Rational Design and Synthesis of Small Molecule, Non-oligosaccharide Selectin Inhibitors: (.alpha.-D-Mannopyranosyloxy)biphenyl-Substituted Corboxylic Acids," J. Med. Chem. 38: 4976-4984, Dec. 22, 1995.
Kohler and Milstein, "Continuous cultures of fused cells secreting antibody of predefined specificity," Nature 256:495-497, 1975.
Kohler and Milstein, "Derivation of specific antibody-producing tissue culture and tumor lines by cell fusion," Eur. J. Immunol. 6:511-519, 1976.
Kojima and Hakomori, "Specific Interaction between Gangliotriaosylceramide (G.sub.g3) and Sialosyllactosylceramide (G.sub.M3) as a Basis for Specific Cellular Recognition between Lymphoma and Melanoma Cells," J. Biol. Chem. 264(34):20159-20162, 1989.
Kolb, H. C. et al., "Development of Tool for the Design of Selectin Antagonists," Chem. Eur. J. 3(10):1571-1578, 1997.
Kolb, H. C. et al., "Recent progress in the glycodrug area," Pure & Applied Chemistry 69(9):1879-1884, 1997.
Komrokji, Rami S., et al., "The Colony-Stimulating Factors: Use to Prevent and Treat Neutropenia and Its Complications," Expert Opin.Biol. Ther., 4:1897-1910, (2004).
Koprowski et al., "Colorectal Carcinoma Antigens Detected by Hybridoma Antibodies," Somatic Cell Genetics 5(6):957-972, 1979.
Kuzuoka, "Antitumor activity of murine monoclonal antibody NCC-ST-421," Chem. Ab. 115:27344v, 1991.
Kwiatskowski et al., "Tautomerism and Electronic Structure of Biological Pyrimidines" Adv Het Chem 1975, pp. 199-335.
Kwong et al., "An Antagonist of the Chemokine Receptor CXCR4 Induces Mitotic Catastrophe in Ovarian Cancer Cells," Mol. Cancer Ther. 8(7): 1893-1905, Jul. 2009.
Kwong, P. D. et al., "Rational Design of Vaccines to Elicit Broadly Neutralizing Antibodies to HIV-1," Cold Spring Harbor Perspectives in Medicine 1-16, 2011.

(56) References Cited

OTHER PUBLICATIONS

Kyriakides et al., Surgery, 128(2):327-31, Aug. 2000.
Lamblin et al., "Primary Structure Determination of Five Sialylated Oligosaccharides Derived from Bronchial Mucus Glycoproteins of Patients Suffering from Cystic Fibrosis.," Journal of Biological Chemistry 259(14):9051-9058, 1984.
Lanne, B. et al., "Binding of the galactose-specific Pseudomonas aeruginose lectin, PA-I, to glycosphingolipids and other glycoconjugates," Glycoconjugate Journal, 11:292-298 (1994).
Larsen et al., "PADGEM-Dependent Adhesion of Platelets to Monocytes and Neutrophils is Mediated by a Lineage-Specific Carbohydrate, LNF III (CD15)," Cell 63:467-474, 1990.
Lee et al., "A new method of sequencing linear oligosaccharides on gels using charged, fluorescent coniugates" Carbohydrate Research, vol. 214, 1991, pp. 155-168, XP000226749.
Lemoli et al., "Hematopoietic stem cell mobilization," Haematologica, 93 (3): 321-324 (2008).
Leppla, S H et al., "Anthrax Toxin Fusion Proteins for Intracellular Delivery of Macromolecules," Journal of Applied Microbiology., 87(2): p. 284 (Aug. 1, 1999).
Ley, K. et al., "Selectins in T-cell Recruitment to Non-Lymphoid Tissues and Sites of Inflammation," Nature Reviews, 4: 1-11 (May 2004).
Ley, K., "The role of selectins in inflammation and disease," Trends in Molecular Medicine, 9(6): 263-268 (Jun. 2003).
Li, B., et al., "Delaying Acute Graft-Versus-Host Disease in Mouse Bone Marrow Transplantation by Treating Donor Cells with Antibodies Directed at L-Selectin and a4 Integrin Prior to Infusion," Scand. J, I Immunol 59:464-468, 2004.
Lindenberg et al., "Carbohydrate binding properties of mouse embryos," J. Reprod. Fert. 89:431-439, 1990.
Lipartiti et al., "Monosialoganglioside GM1 Reduces Nmda Neurotoxicity in Neonatal Rat Brain," Experimental Neurology 113:301-305, 1991.
Loetscher et al., "N-terminal Peptides of Stromal Cell-derived Factor-1 with CXC Chemokine Receptor 4 Agonist and Antagonist Activities," J. Biol. Chem. 273(35):22279-22283, 1998.
Lowe et al., "A transfected human fucosyltransferase cDNA determines biosynthesis of oligosaccharide ligand(s) for endothelial-leukocyte adhesion molecule I," Biochem. Soc. Trans. 19(3):649-653, 1991.
Lowe et al., "ELAM-1-Dependent Cell Adhesion to Vascular Endothelium Determined by a Transfected Human Fucosyltransferase cDNA," Cell 63:475-484, 1990.
Luallen, R. J. et al., "A Yeast Glycoprotein Shows High-Affinity Binding to the Broadly Neutralizing Human Immunodeficiency Virus Antibody 2G12 and Inhibits gp120 interactions with 2G12 and DC-SIGN," Journal of Virology 83(1):4861-4870, May 2009.
Macher et al., "A Novel Carbohydrate, Differentiation Antigen on Fucogangliosides of Human Myeloid Cells Recognized by Monoclonal Antibody VIM-2," Journal of Biological Chemistry 263(21):10186-10191, 1988.
Magnani et al., "A Monoclonal Antibody-defined Antigen Associated with Gastrointestinal Cancer Is a Ganglioside Containing Sialylated Lacto-N-fucopentaose II," Journal of Biological Chemistry 257(23):14365-14369, 1982.
Magnani et al., "Identification of the Gastrointestinal and Pancreatic Cancer-associated Antigen Detected by Monoclonal Antibody 19-9 in the Sera of Patients as a Mucin," Cancer Res. 43:5489-5492, 1983.
Magnani et al., "Pan-selectin Antagonist GMI-1070 affects Biomarkers of Adhesion, Activation and the Coagulation Cascade in Sickle Cell Adults at Steady State", Blood, 120, Abstract #87, Nov. 2012.
Magnani, "The Discovery, Biology, and Drug Development of Sialyl Le$^a$ and Sialyl Le$^x$", Archives of Biochemistry and Biophysics, 426:122-131, May 8, 2004.
Magnani, J., "Carbohydrate Sequences Detected by Murine Monoclonal Antibodies," Chemistry and Physics of Lipids 42:65-74, 1986.
Magnani, J., "Potent Glycomimetic Inhibitors of the Adhesion Molecule, PA-IIL, for the Bacterial Pathogen, Pseudomonas auroginosa," Glycobiology 13(11): 854, Abstract No. 104, Oct. 2003.
Maly, P., et al., "The a(1,3)Fucosyltransferase Fuc-TVII Controls Leukocyte Trafficking through an Essential Role in L-, E-, and P-selection Ligand Biosynthesis", Cell. 86(4), It 1996), 643-653.
Mann, AP et al., "Identification of Thioaptamer Ligand against E-Selectin: Potential Application for Inflamed Vasculature Targeting," PLoS ONE, 5(9): 1-11 (Sep. 2010).
Matsuda, Masao et al., "Heterobifunctional Ligands: Practical Chemoenzymatic Synthesis of a Cell Adhesive Glycopeptide That Interacts With Both Selectins and Integrins," J. Med. Chem. 44:715-724, 2001.
Matsui, N. M. et al., "Heparin inhibits the flow adhesion of sickle red blood cells to Pselectin," Blood 100(10):3790-3796, Nov. 15, 2002.
Matsui, N. M. et al., "The Novel Adhesion of Erythrocytes to P-Selectin in Sickle Cell Disease," Blood 96(11) Pt. 1:600a, Abstract #2575, Nov. 16, 2000.
Matsui, N. M.et al., "P-selectin mediates the adhesion of sickle erythrocytes to the endothelium," Blood 98(6):1955-1962, Sep. 15, 2001.
Mauch, P., et al., "Hematopoietic Stem Cell Compartment: Acute and Late Effects of Radiation Therapy and Chemotherapy", Int. J. Radiation Oncology Bioi. Phys .. 31(5), 1995), 1319-1339.
McCavit et al., "An Analysis of the Pediatric Sub-Group From the Phase 2 Study of GMI-1070—A Novel Agent for the Vaso-Occlusive Crisis of Sickle Cell Anemia", Blood, 122(21):2206, Nov. 15, 2013.
McCavit et al., "An Analysis of the Pediatric Sub-Group From the Phase 2 Study of GMI-1070—A Novel Agent for the Vaso-Occlusive Crisis of Sickle Cell Anemia", ASH Annual Meeting 2013, Poster #56448, Dec. 8, 2013.
McEver et al., "Leukocyte trafficking mediated by selectin-carbohydrate interactions," J. Biol. Chem., 270 (19): 11025-11028 (1995).
Mckenzie, J. L., et al., "Low rhodamine 123 retention identifies long-term human hematopoietic stem cells with the Lin -CD34+ CD38-population", Blood. 109, (2007), 543-545.
McLean P. et al., "Effects of a small molecule inhibitor of ICAM-1 and E-selectin expression on colonic inflammatory hyperalgesia and colitis" Digestive Disease 2003, Orlando FL, May 2003, abstract.
Menendez, A., et al., "A Peptide Inhibitor of HIV-1 Neutralizing Antibody 2G12 is not a Structural Mimic of the Natural Carbohydrate Epitope on gp120," The FASEB Journal 22:1380-1382, May 2008.
Mimeault, et al., "Stem cells: a revolution in therapeutics-recent advances in stem cell biology and their therapeutic applications in regenerative medicine and cancer therapies," Clin. Pharmacol. Therapeutics, 82(3): 252-264 (2007).
Mitsiades, et al., "Preclinical studies in support of defibrotide for the treatment of multiple myeloma and other neoplasias," Clin. Cancer Res., 15 (4): 1210-1221 (2009).
Moore, M., "Waking Up HSCs: A new Role for E-Selectin," Nat. Med., 18:16131614, (2012).
Moore, P. L. et al., "Evolution of an HIV Glycan-Dependent Broadly Neutralizing Antibody Epitope Through Immune Escape," Nature Medicine doi:10.1038/nm.2985 pp. 1-6, Oct. 2012.
Mosley et al., "Recent Patents Regarding the Discovery of Small Molecule CXCR4 Antagonists," Expert Opin. Ther. Patents 19(1):23-38, 2009.
Mulligan and Berg "Selection for animal cells that express the *Escherichia coli* gene coding for xanthine-gunine phosphoribosyltransferase," Proc. Natl. Acad. Sci. USA 78:2072-2076, 1981.
Mulligan et al., "Role of Endothelial-Leukocyte Adhesion Molecule 1 (ELAM-1) in Neutrophil-mediated Lung Injury in Rats," J Clin Invest.,88(4):1396-406, Oct. 1991.
Myers et al., "E-Selectin Inhibitor GMI-1271 Works in Combination with Low-Molecular Weight Heparin to Decrease Venous Thrombosis and Bleeding Risk in a Mouse Model", Blood, 124(21):593, Dec. 6, 2014.

(56) References Cited

OTHER PUBLICATIONS

Myers et al., "Novel E-Selectin Antagonist GMI-1271 Decreases Venous Thrombosis without Increased Bleeding Potential in a Mouse Model", ASH Annual Meeting 2012, Poster #53444, Dec. 10, 2012.
Myers et al., "Pan-Selectin Antagonist, GMI-1070 Decreases Venous Thrombosis in a Mouse Model", Blood, 118, Abstract #3273, Nov. 2011.
Nagel, R. L., "A Knockout of a Transgenic Mouse-Animal Models of Sickle Cell Anemia," The New England Journal of Medicine 339:194-195, Jul. 16, 1998.
Narita, T. et al., "Corticosteroids and medroxyprogesterone acetate inhibit the induction of breast cancer cells," Anticancer Research, 15(6B): 2523-2527 (1995)—Abstract.
Narum, Tetsuo et al., "Synthesis and Biological Evaluation of Selective CXCR4 Antagonists Containing Alkene Dipeptide Isosteres," Organic & Biomolecular Chemistry, 8(3): 616-621(Feb. 7, 2010).
Natarajan, M.M. et al., "Adhesion of sickle red blood cells and damage to interleukinlbeta stimulated endothelial cells under flow in vitro," Blood 87:4845-4852, 1996.
Natoni et al., "Multiple Myeloma Cells Express Functional E-Selectin Ligands Which Can be Inhibited Both in-Vitro and in-Vivo Leading to Prolongation of Survival in a Murine Transplant Model", Blood, 124(21):4718, Dec. 6, 2014.
Nguyen, M et al., "Novel synthetic analogs 1-29 of sialyl Lewis X can inhibit angiogenesis in vitro and in vivo," Biochemical and Biophysical Research Communications, 228(3): 716-723 (Nov. 21, 1996).
Nicolaou et al., "Total Synthesis of the Tumor-Associated Le$^x$ Family of Glycosphingolipids," J. Amer. Chem. Soc. 112:3693-3695, 1990.
Noguchi, M. et al. "A minor E-selectin ligand, CD65, is critical for extravascular infiltration of acute myeloid leukemia cells," Leukemia Research, 25: 847-853 (2001).
Norman et al., "Sialyl Lewisx(sLex) and an sLex Mimetic, CGP69669A, Disrupt E-Selectin-Dependent Leukocyte Rolling In Vivo," Blood , 91(2):475-483 (Jan. 15, 1998).
Notice of Allowance dated Jun. 22, 2017 in U.S. Appl. No. 14/752,056.
Notice of Allowance dated Jun. 23, 2017 in U.S. Appl. No. 14/650,102.
Nudelman et al., "Novel Fucolipids of Human Adenocarcinoma: Disialosyl Lea Antigen (III.sup.4FucIII.sup.6NeuAcIV.sup.3NeuAcLc.sub.4) of Human Colonic Adenocarcinoma and the Monoclonal Antibody (FH7) Defining This Structure," J. Biol. Chem. 261:5487-5495,1986.
Nutku, E. et al., "Ligation of Siglec-8: a selective mechanism for induction of human eosinophil apoptosis," Blood, 101(12): 5014-5020 (2003).
Obermajer, N. et al., "Design, synthesis and activity evaluation of mannose-based DC-SIGN antagonists," Molecular Diversity 15:347-360, May 2011.
Office Action dated Apr. 5, 2012 in U.S. Appl. No. 12/418,774.
Orhlein, R., "Carbohydrates and Derivatives as Potential Drug Candidates with Emphasis on the Selectin and Linear-B Area," Mini Reviews in Medicinal Chemistry 1: 349-361, 2001.
Oxford Textbook of Oncology, vol. 1, published 1995 by Oxford University Press, pp. 447-453.
Palcic et al., "A Bisubstrate Analog Inhibitor for .alpha.(1.fwdarw.2)-Fucosyltransferase," J. Biol. Chem. 264:17174-17181, 1989.
Palcic et al., "Enzymic Synthesis of Oligosaccharides Terminating in the Tumor-Associated Sialyl-Lewis-a Determinant," Carbohydr. Res. 190:1-11, 1989.
Palcic et al., "Regulation of N-Acetylglucosaminyltransferase V Activity. Kinetic Comparisons of Parental, Rous Sarcoma Virus-Transformed BHK, and .sub.L-Phytohemagglutinin-Resistant BHK Cells Using Synthetic Substrates and an Inhibitory Substrate Analog," J. Biol. Chem. 265:6759-6769, 1990.
Palma-Vargas, J.M. et al., "Small-Molecule Selectin Inhibitor Protects Against Liver Inflammatory Response After Ischemia and Reperfusion," J. Am. Coll. Surg. 185: 365-372, 1997.
Pamphilon et al., "Stem Cell Donation—What advice can be given to the donor?," Br. J. Haematol. 147(1):71-76, Oct. 2009, Author manuscript available at NIH Public access Aug. 1, 2012.
Patton, J. T. et al., "GMI-1070: a Small Glycomimetic, Pan-selectin Antagonist that Improves Blood Flow and Inhibits Blood Cell Adhesion in Sickle Mice," Abstract ID:ABSTY-5APYL-CA6TP-V2ET6, Sep. 2, 2005.
Payre, et al., "Chemoenzymatische Synthese eines zweifach modifizierten Pentasaccharids als Substrat fur einen alpha-Amylase-Assay durch Fluoreszenz-loschung" Angew. Chem., vol. 107, No. 11, 1995, pp. 1361-1364.
Payre, N. et al., "Chemoenzymatic Synthesis of a Modified Pentasaccharide as a Specific Substrate for a Sensitive Assay of a-Amylase by Fluorescence Quenching," Angew. Chem. Int. Ed. Engl. 34(11): 1239-1241 (1995).
Pejchal R. et al., "A Potent and Broad Neutralizing Antibody Recognizes and Penetrates the HIV Glycan Shield," Science 334:1097-1103, Nov. 2011.
Pelus, "Peripheral blood stem cell mobilization: new regimens, new cells, where do we stand," Curr. Opin. Hematol., 15(4): 285-292 (2008).
Pentelute, Brad et al., "A Semisynthesis Platform for Investigating Structure-Function Relationships in the N-Terminal Domain of the Anthrax Lethal Factor," ACS Chemical Biology. 5(4): 359-364 (Apr. 2010).
Pentelute, Brad L. et al., "Chemica 1 1-16 dissection of protein translocation through the anthrax toxin pore," Angewandte Chemie, 50(10): 2294-2296 (Mar. 1, 2011).
Perret, S. et al., "Structural basis for the interaction between human milk oligosaccharides and the bacterial lectin PA-IIL of Pseudomonas aeruginosa," Biochem. J. 389: 325-332, 2005. cited by other.
Phillips et al., "ELAM-1 Mediates Cell Adhesion by Recognition of a Carbohydrate Ligand, Sialyl-Le.sup.x," Science 250:1130-1132, 1990.
Picker er al., "The Neutrophil Selectin LECAM-1 Presents Carbohydrate Ligands to the Vascular Selectins ELAM-1 and GMP-140," Cell 66:921-933, 1991.
Plasterk, R. H. A., et al., "The silence of the genes", Current Opinion in Genetics and Develooment 10 (2000), 562-567.
Price et al., "Breast Cancer Cells Metastasize to Bone through E-Selectin Positive Vascular Gateways", AACR Annual Meeting 2014, Poster #4831, Apr. 9, 2014.
Prokazova et al., "Sialylated lactosylceramides. Possible inducers of non-specific immunosuppression and atherosclerotic lesions," European Journal of Biochemistry 172:1-6, 1988.
Purton, L. E. et al., "Limiting Factors in Murine Hematopoietic Stem Cell Assays," Cell Stem Cell 1: 263-270, Sep. 2007.
Rapoport, E. et al., "Probing Sialic Acid Binding Ig-Like Lectins (Siglecs) with Sulfated Oligosaccharides," Biochemistry (Moscow), 71(5): 496-504 (2006).
Rauvala et al., "Studies on Cell Adhesion and Recognition. I. Extent and Specificity of Cell Adhesion Triggered by Carbohydrate-reactive Proteins (Glycosidases and Lectins) and by Fibronectin," J. Cell Biol. 88:127-137, 1981.
Reina, J. J. et al., "1,2-Mannobioside Mimic: Synthesis, DC-SIGN Interaction by NMR and Docking, and Antiviral Activity," ChemMedChem 2:1030-1036, 2007.
Rice and Bevilacqua, "An Inducible Endothelial Cell Surface Glycoprotein Mediates Melanoma Adhesion," Science 246:1303-1306, 1989.
Richert et al., "Inhibition of CXCR4 by CTCE-9908 Inhibits Breast Cancer Metastasis to Lung and Bone," Oncology Reports 21:761-767, 2009.
Roberge, J. Y., et al., "A Strategy for a Convergent Synthesis of N-Linked Glycopeptides on a Solid Support", Science 269(5221), (1995), 202-204.
Rood, P.M.L. et al., "E-Selectin and Very Late Activation Antigen-r Mediate Adhesion of Hematopoietic Progenitor Cells to Bone Marrow Endothelium," Ann Hematol, 79:477-484, (2000).

(56) References Cited

OTHER PUBLICATIONS

Ruoslahti and Pierschbacher, "New Perspectives in Cell Adhesion: RGD and Integrins," Science 238:491-497, 1987.
Sackstein, "The Biology of CD44 and HCELL in Hematopoiesis: The 'Step 2-Bypass Pathway' and Other Emerging Perspectives", Current Opinion in Hematology, 18(4):239-248 (2011).
Sakurai et al., "Selection of a Monoclonal Antibody Reactive with a High-Molecular-Weight Glycoprotein Circulating in the Body Fluid of Gastrointestinal Cancer Patients," Cancer Research 48:4053-4058, 1988.
Sanz, M.-J., et al., "Roflumilast inhibits leukocyte-endothelial cell interactions, expression of adhesion molecules and microvascular permeability", British Journal of Pharmacology. 152(4), (2007), 481-492.
Sastry et al., "Cloning of the immunological repertoire in *Escherichia coli* for generation of monoclonal catalytic antibodies: Construction of a heavy chain variable region-specific cDNA library," Proc. Natl. Acad. Sci. USA 86:5728-5732, 1989.
Scanlan, C. N. et al., "Exploiting the Defensive Sugars of HIV-1 for Drug and Vaccine Design," Nature 446:1038-1045, Apr. 2007.
Scanlan, C. N. et al., "The Broadly Neutralizing Anti-Human Immunodeficiency Virus Type 1 Antibody 2G12 Recognizes a Cluster of a1-2 mannose Residues on the Outer Face of gp120," Journal of Virology 76:7306-7321, Jul. 2002.
Scharfman, A. et al., "Pseudomonas aeruginosa binds to neoglycoconjugates bearing mucin carbohydrate determinants and predominantly to sialyl-Lewis x conjugates," Glycobiology 9(8): 757-764, 1999.
Scharfman, A. et al., "Recognition of Lewis x Derivatives Present on Mucins by Flagellar Components of Pseudomonas aeruginosa," Infection and Immunity 69(9): 5243-5248, Sep. 2001.
Schief, W. R. et al., "Challenges for Structure-Based HIV Vaccine Design," Current Opinion in HIV and AIDS 4:431-440, 2009.
Schwizer, D. et al. "Pre-organization of the Core Structure of E-Selectin Antagonist," Chemistry—A European Journal, 18(5): 1342-1351 (Jan. 2012).
Shan, M. et al., "HIV-1 gp120 Mannoses Induce Immunosuppressive Responses from Dendritic Cells," PLoS Pathogens 3(11):e169 1637-1650, Nov. 2007.
Shitara et al., "Application of Anti-Sialyl Le.sup.a Monoclonal antibody, KM231, for Immunotherapy of Cancer," Anticancer Res. 11:2003-2014, 1991.
Simanek Eric A. et al. "Selectin-carbohydrate interactions: from natural ligands to designed mimics", Chemical Reviews vol. 98, No. 2, pp. 833-862, Jan. 1998.
Simon et al, "Effects of Selectin Antagonist GMI-1070 on the Activation State of Leukocytes in Sickle Cell Patients not in Crisis" ASH Annual Meeting 2010, Poster #32407, Dec. 6, 2010.
Simon et al., "Inhibition of E-Selectin Inflammatory Function by the Glycomimetic GMI-1070" Blood, 118, Abstract #851, Nov. 2011.
Simon et al., "Mightier than the sickle cell (editorial)", Blood, 116(10), 1633, Sep. 9, 2010.
Singh et al., "Evaluation of a CXCR4 Antagonist in a Xenograft Mouse Model of Inflammatory Breast Cancer," Clin. Exp. Metastasis 27:233-240, Mar. 2010.
Sipkins, Dorothy A. et al., "In Vivo Imaging of Specialized Bone Marrow Endothelial Microdomains for Tumor Engraftment," Nature Pub. Group GB 435 (7044):969-973, Jun. 2005.
Siuzdak et al., "Examination of the Sialyl Lewis X—Calcium Complex by Electrospray Mass Spectrometry," Bioorganic & Medicinal Chemistry Letters 4(24): 2863-2866, 1994.
Solovey et al., "Circulating Activated Endothelial Cells in Sickle Cell Anemia," The New England Journal of Medicine 337:1584-1590, Nov. 27, 1997.
Solovey, AA et al. "Modulation of endothelial cell activation in sickle cell disease: a pilot study," Blood, 97(7): 1937-1941 (Apr. 2001).
Sprengard, U. et al., "Synthesis and Biological Activity of Novel Sialyl-Lewis.sup.X Conjugates," Bioorganic & Medicinal Chemistry Letters 6(5): 509-514, 1996.

Stanley and Atkinson, "The LEC11 Chinese Hamster Ovary Mutant Synthesizes N-Linked Carbohydrates Containing Sialylated, Fucosylated Lactosamine Units. Analysis by One- and Two-Dimensional H NMR Spectroscopy," J. Biol. Chem. 263(23):11374-11381, 1988.
Steele et al., "A Small Molecule Glycomimetic Antagonist of E-selectin (GMI-1271) Prevents Pancreatic Tumor Metastasis and Offers Improved Efficacy of Chemotherapy", AACR Annual Meeting 2014, Poster #4503, Apr. 8, 2014.
Steele et al., "A Small Molecule Glycomimetic Antagonist of E-selectin (GMI-1271) Prevents Pancreatic Tumor Metastasis and Offers Improved Efficacy of Chemotherapy", Cancer Res, 74:Abstract 4503, Oct. 1, 2014.
Steele et al., "425 A small molecule glycomimetic antagonist of E-selectin and CXCR4 (GMI-1359) prevents pancreatic tumor metastasis and offers improved chemotherapy" Cancer Research, Aug. 2015.
Stephens and Cockett,"The construction of highly efficient and versatile set of mammalian expression vectors," Nucleic Acids Research. 17:7110, 1989.
Stevenson, J. et al., "Differential metastasis inhibition by clinically relevant levels of heparins," Clin. Cancer Res. 11(19): 7003-7011 (2005).
Streeter et al., "Immunohistologic and Functional Characterization of a Vascular Addressin Involved in Lymphocyte Homing into Peripheral Lymph Nodes," Journal of Cell Biology 107: 1853-1862, 1988.
Stroud et al. ,"Extended Type 1 Chain Glycosphingolipids: Dimeric Le.sup.a (III.sup.4V.sup.4Fuc.sub.2Lc.sub.6) as Human Tumor-associated Antigen," J. Biol. Chem. 266(13):8439-8446, 1991.
Styles et al., GMI-1070, a Pan-Selectin Inhibitor: Safety and PK in a Phase 1/2 Study in Adults with Sickle Cell Disease, ASH Annual Meeting 2010, Poster #31824, Dec. 4, 2010.
Sudhoff, T. et al., "Cutting Edge Communication: Circulating Endothelial Adhesion Molecules (sE-Selectin, sVCAM-1 and SICAM-1) During rHuG-CSF-Stimulated Stem Cell Mobilization," Jour. Hematother. & Stem Cell Res., 11:147-151 (2002),.
Supplementary European Search Report in EP 03739223 dated Jan. 16, 2009.
Suzuma, I. et al., "Contribution of E-Selectin to Cellular Infiltration during Endotoxin-Induced Uveitis," Invest. Ophthalmol. Vis. Sci., 39: 1620-1630 (1998).
Svenson and Lindberg, "Coupling of Acid Labile Salmonella Specific Oligosaccharides to Macromolecular Carriers," J. Immunol. Meth. 25:323-335, 1979.
Symon, FA et al., "Selectins and their Counter receptors: a bitter sweet attraction," Thorax, 51: 1155-1157 (1996).
Tabarani G. et al., "Mannose Hyperbranched Dendritic Polymers Interact with Clustered Organization of DC-SGIN and Inhibit gp120 Binding," FEBS Letters 580:2402-2408, Mar. 2006.
Takada et al., "Adhesion of Human Cancer Cells to Vascular Endothelium Mediated by a Carbohydrate Antigen, Sialyl Lewis $A^1$," Biochem. Biophys. Res. Commun. 179(2):713-719, 1991.
Takahashi, Takashi et al., "Design and Synthesis of a Water-Soluble Taxol Analogue : Taxol-Sialyl Conjugate," Bioorg. & Med. Chem. Letters 8:113-116, 1998.
Takeichi, M., "Cadherins: a molecular family essential for selective cell-cell adhesion and animal morphogenesis," Trends Genet. 3(8):213-217, 1987.
Tamamura, H. et al., "Identification of a New Class of Low Molecular Weight Antagonists against the Chemokine Receptor CXCR4 Having the Dipicolylamine-Zinc(II) Complex Structure" J. Med. Chem., 49: 3412-3415 (2006).
Tanaka, T. et al., "Azamacrocyclic Metal Complexes as CXCR4 Antagonists," ChemMedChem, 6: 834-839 (2011).
Tedder, TF et al., "The selectins: vascular adhesion molecules," FASEB J, 9(10): 866-73 (1995).
Telen et al., "GMI 1070: Reduction in Time to Resolution of Vaso-Occlusive Crisis and Decreased Opioid Use in a Prospective, Randomized, Multi-Center Double Blind, Adaptive Phase 2 Study in Sickle Cell Disease" Blood, 122(21):776, Nov. 15, 2013.
Telen et al., "Randomized phase 2 study of GMI-1070 in SCD: reduction in time to resolution of vaso-occlusive events and decreased opioid use", Blood, 125(17):2656-2664, Apr. 23, 2015.

(56) References Cited

OTHER PUBLICATIONS

The Merck Manual of Diagnosis and Therapy, Seventeenth Edition, published 1999 by Merck Research Laboratories, pp. 397, 398, 948,949, 1916, 1979-1981.
Thoma G. et al., "A readily Available, Highly Potent E-Selectin Antagonist," Angew. Chem. Int. Ed. 40(19): 3644-3647, 2001.
Thoma, G et al., "Nanomolar E-selectin inhibitors: 700-fold potentiation of affinity by multivalent ligand presentation," Journal of the American Chemical Society, 123(41): 10113-10114 (Oct. 17, 2001).
Thoma, G. et al., "Preorganization of the Bioactive Conformation of Sialyl Lewis$^x$ Analogues Correlates with Their Affinity to E-Selectin," Angew. Chem. Int. Ed. 40(10): 1941-1945, 2001.
Thoma, G. et al., "Synthesis and biological evaluation of a potent E-selectin antagonist," J. Med. Chem. 42 (23): 4909-4913, Nov. 18, 1999.
Thoma, G. et al., "Synthesis and Biological Evaluation of a Sialyl Lewis X Mimic with Significantly Improved E-selectin Inhibition," Bioorganic & Medicinal Chemistry Letters 11: 923-925, 2001.
Tilton, R.G., "Endotoxin-Induced Leukocyte Accumulation in Aqueous Fluid of Rats is Decreased by a Small Molecule Selectin," Investigative Opthalmology & Visual Science 37(3): S918, Abstract No. 4227, Feb. 15, 1996.
Titz et al., "Is adamantine a suitable substituent to pre-organize the acid orientation in E-selectin antagonists?", Bioorganic & Medicinal Chemistry, 16 (2008), 1046-1056.
Titz et al., "Mimetics of Sialyl Lewis$^x$ : The Pre-Organization of the Carboxylic Acid is Essential for Binding to Selectins", Chimia, 61:194-197, 2007.
Titz, A. et al., "Probing the carbohydrate recognition domain of E-selectin: The importance of the acid orientation in sLex mimetics," Bioorg. Med. Chem., 18(1): 19-27 (2010).
Todderund et al., "BMS-190394, a Selectin Inhbitor, Prevents Rat Cutaneous Inflammatory Reactions," J Pharmacal Exp Ther., 282(3):1298-304, Sep. 1997.
Toepfer et al., "Synthesis of Novel Mimetics of the Sialyl Lewis X Determinant," Tetrahedron Letters, vol. 36, No. 50, pp. 9161-9164, 1995.
Togel et al., "Administered mesenchymal stem cells protect against ischemic acute renal failure through differentiation-independent mechanisms," Am. J. Physical Renal Physiol., 289:F31-42, Jul. 2005.
Totani, K. et al., "Chemoenzymatic synthesis and application of glycopolymers containing multivalent sialyloligosaccharides with a poly(L-glutamic acid) backbone for inhibition of infection by influenza viruses," Glycobiology, 13(5): 315-326 (2003).
Trouet et al., "A covalent linkage between daunorubicin and proteins that is stable in serum and reversible by lysosomal hydrolases, as required for a lysosomotropic drug-carrier conjugate: In vitro and in vivo studies," Proc. Natl. Acad. Sci. USA 79:626-629, 1982.
Turhan, et al., "Primary role for adherent leukocytes in sickle cell vascular occlusion: A new paradigm," Proceedings of the National Academy of Sciences of the United States of America 99(5):3047-3051, Mar. 5, 2002.
Turner et al., "Molecular Basis of Epithelial Barrier Regulation From Basic Mechanisms to Clinical Application," The American Journal of Pathology, 169(6): 1901-1909 (Dec. 2006).
Tyrrell, D. et al. "Structural requirements for the carbohydrate ligand of E-selectin," PNAS, 88: 10372-10376 (Nov. 1991).
Ueda et. al., "Structure-Activity Relationships of Cyclic Peptide-Based Chemokine Receptor CXCR4 Antagonists: Disclosing the Importance of Side-Chain and Backbone Functionalities," J. Med. Chem. 50:192-198, 2007.
Venkataraman, Nitya, et al., "Reawakening Retrocyclins: Ancestral Human Defensins Active Against HIV-1," Plos Biology, 7(4): 720-729 (Apr. 2009).
Wai, "Blockade of Chemokine (C-X-C motif) Receptor 4 for the Inhibition of Hepatocellular Carcinoma Metastasis," A Thesis, in partial fulfillment of requirements for Ph.D. Degree at the Univ. of Hong Kong, Jun. 2008.
Waldmann, H. et al., "Synthesis of 2-Acetamindo-2-Deoxyglucosylasparagine Glyco-Tripeptide and-Pentapeptides by Selective C- and N-Terminal Elongation of the Peptide Chain," Carbohydrate Research 196: 75-93, 1990.
Walker, L. M. et al., "Rapid Development of Glycan-Specific, Broad, and Potent Anti-HIV-1 gp120 Neutralizing Antibodies in an R5 SIV/HIV Chimeric Virus Infected Macaque," Proceedings of the National Academy of Sciences 108(50):20125-20129, Dec. 2011.
Walsh, GM. "Novel Therapies for Asthma—Advances and Problems," Current Pharmaceutical Design, 11(23): 3027-3038 (2005).
Walz et al., "Recognition by ELAM-1 of the Sialyl-Le.sup.X Determinant on Myeloid and Tumor Cells," Science 250:1132-1135, 1990.
Wang, L.X. et al., "Binding of High-Mannose-Type Oligosaccharides and Synthetic Oligomannose Clusters to Human Antibody 2G12: Implications for HIV-1 Vaccine Design," Chemistry & Biology 11:127-134, Jan. 2004.
Wang, S.K. et al., "Targeting the Carbohydrates on HIV-1: Interaction of Oligomannose Dendrons with Human Monoclonal Antibody 2G12 and DC-SIGN," Proceedings of the National Academy of Sciences 105(10):3690-3695, Mar. 2008.
Wang, Y. et al. "Effect of ginsenoside rgl and rh1 on the expression of hla-dr, cd25, cd44, cd11c and e-selectin on dendritic cell," Zhongguo Mianyixue Zazhi, 23(1): 46-48 (2007)—Abstract.
Ward and Mulligan, "Blocking of adhesion molecules in vivo as anti-inflammatory therapy," Immunology 1: 165-171, 1994.
Wesche, Jorgen et al., "Characterization of membrane translocation by anthrax protective antigen," Biochemistry, 37(45): 15737-15746 (Nov. 10, 1998).
Whisler and Yates, "Regulation of Lymphocyte Responses by Human Gangliosides. I. Characteristics of Inhibitory Effects and the Induction of Impaired Activation," Journal of Immunology 125(5):2106-2111, 1980.
Winkler et al., "Absence of E-selectin at vascular niche delays hematopoietic stem cell turn-over," Blood, 110(11):188A, Nov. 2007.
Winkler et al., "Absence or blockage of E-Selectin-Mediated Cell Adhesion Delays Hematopoietic Stem Cell", ASH Annual Meeting 2009, Abstract #564, Nov. 2009.
Winkler et al., "Absence or blockage of E-Selectin-Mediated Cell Adhesion Delays Hematopoietic Stem Cell", Blood, 114(22), Abstract #564, Dec. 7, 2009.
Winkler et al., "Adhesion of E-selectin promotes growth inhibition and apoptosis of human and murine hematopoietic progenitor cells independent of PSGL-1," Blood, 103(5):1685-92, Mar. 1, 2004.
Winkler et al., "Administration of E-selectin Antagonist GMI-1271 Improves Survival to High-Dose Chemotherapy by Alleviating Mucositis and Accelerating Neutrophil Recovery", Blood, 122(21):2266, Nov. 15, 2013.
Winkler et al., "Administration of E-selectin Antagonist GMI-1271 Improves Survival to High-Dose Chemotherapy by Alleviating Mucositis and Accelerating Neutrophil Recovery", ASH Annual Meeting, Poster #63045, Dec. 8, 2013.
Winkler et al., "Mobilisation of Reconstituting HSC Is Boosted by Synergy Between G-CSF and E-Selectin Antagonist GMI-1271", Blood, 124(21):317, Dec. 6, 2014.
Winkler et al., "Vascular Niche E-Selectin Protects Acute Myeloid Leukemia Stem Cells from Chemotherapy", Blood, 124(21):620, Dec. 6, 2014.
Winkler et al., "Vascular Niche E-Selectin Regulates Hematopoietic Stem Cell Dormancy, Self Renewal and Chemoresistance", Nature Medicine, doi:10.1038/nm2969, Oct. 21, 2012.
Winnard, P. et al., "Real time non-invasive imaging of receptor-ligand interactions in vivo," J. Cell. Biochem., 90: 454-463 (2003).
Winzer, K. et al. "The Pseudomonas aeruginosa Lectins PA-IL and PA-IIL are Controlled by Quorom Sensing and by RpoS," J. Bacteriol. 182(22): 6401-6411 (2000).
Witz, "The involvement of selectins and their ligands in tumor-progression," Immunol. Lett., 104 (1-2): 89-93 (2006).
Wu, B. et al. "Structures of the CXCR4 Chemokine GPCR with Small-Molecule and Cyclic Peptide Antagonists," Science, 330(6007): 1066-1071 (Nov. 2010).

(56) References Cited

OTHER PUBLICATIONS

Wun et al., "Pan-Selectin Antagonist Rivipansel (GMI-1070) Reduces Soluble E-Selectin Levels While Improving Clinical Outcomes in SCD Vaso-Occlusive Crisis" Blood, 124(21):2704, Dec. 6, 2014.
Xu, J. et al., "Molecular insights and therapeutic targets for diabetic endothelial dysfunction," Circulation, 120: 1266-1286 (2009).
Yamazaki, F. et al,. "Synthesis of an appropriately protected core glycotetraoside, a key intermediate for the synthesis of 'bisected' complex-type glycans of a glycoprotein," Carbohydrate Research 201: 15-30, 1990.
Zeisig et al., "Effect of sialyl Lewis X-glycoliposomes on the inhibition of E-selectin-mediated tumour cell adhesion in vitro" Biochimica et Biophysica Acta (2004) 1660, pp. 31-40.
Zhan et al., "Discovery of Small Molecule CXCR4 Antagonists," J. Med. Chem. 50:5655-5664, 2007.
Zhang et al., "Chemokine CXCL 12 and its receptor CXCR4 expression are associated with perineural invasion of prostate cancer" Journal of Experimental and Clinical Cancer Research (2008) vol. 27 No. 62, pp. 1-9.
Zhang, Z. et al. "CXCR4 but not CXCR7 is mainly implicated in ocular leukocyte trafficking during ovalbumin-induced acute uveitis," Experimental Eye Research, 89: 522-531 (2009).
Zhao T. et al. "Targeting human CD34+ hematopoietic stem cells with anti-CD45 x antimyosin light-chain bispecific antibody preserves cardiac function in myocardial infarction" Journal of Applied Physiology, 10(6):1793-1800 (2008).
Zheng, CX et al. "The prognostic value of preoperative serum levels of CEA, CA19-9 and CA72-4 in patients with colorectal cancer," World J. Gastroentero, 7(3): 431-434 (2001).
Zhou et al., "The Selectin GMP-140 Binds to Sialylated, Fucosylated Lactosaminoglycans on Both Myeloid and Nonmyeloid Cells," Journal of Cell Biology 115(2):557-564, 1991.
Zhou, G. et al. "Effect of ET-RA on expression of selectin on the surface of endothelial cell in mice with severe acute pancreatitis," Chongqing Yixue, 35(7): 624-626 (2006)—Abstract.
Zopf et al., "Affinity Purification of Antibodies Using Oligosaccharide-Phenethylamine Derivatives Coupled to Sepharose," Meth. Enzymol. 50:171-175, 1978.
Zuber et al., "Mouse models of human AML accurately predict chemotherapy response," Genes. Dev., 23 (7): 877-889 (2009).

\* cited by examiner

Inhibition of SDF-1-Induced Chemotaxis by Compounds 9 and 16

Data at 35 Days Post Treatment (5 days from the end of treatments)

| Treatment | Animals | Tibiae | % Positive Tibiae | Lytic Area (Lytic units) |
|---|---|---|---|---|
| Vehicle | 8 | 16 | 11/16 (69%) | 3.71 +/- 1.37 |
| Compound 9 | 8 | 16 | 6/16 (37.5%) | 2.17 +/- 0.44 |
| DTX | 5 | 10 | 6/10 (60%) | 6.04 +/- 0.81 |
| Compound 9 + DTX | 8 | 16 | 4/16 (25%) | 1.17 +/- 0.15 |
| E-selectin antagonist | 8 | 16 | 8/16 (50%) | 6.88 +/- 0.49 |
| E-selectin antagonist + DTX | 8 | 16 | 6/16 (37.5%) | 4.97 +/- 1.03 |
| AMD3100 | 5 | 10 | 3/10 (30%) | 3.48 +/- 0.44 |
| AMD + DTX | 5 | 10 | 3/10 (30%) | 1.32 +/- 0.64 |

FIG. 9

HETEROBIFUNCTIONAL INHIBITORS OF E-SELECTINS AND CXCR4 CHEMOKINE RECEPTORS

This application is a United States national stage application filed under 35 U.S.C.§ 371 of International Patent Application No. PST/US 2015/063191 accorded an international filing date of Dec. 1, 2015; which claims the benefit under 35 U.S.C. § 119(e) to U.S. Provisional Application No. 62/087,085 filed Dec. 3, 2014, all of which are incorporated by reference herein in their entirety.

FIELD OF INVENTION

Compounds, compositions, and methods for treating cancer and inflammatory diseases and for enhancing retention of cells after releasing into circulating blood are disclosed herein. For example, heterobifunctional compounds and compositions that inhibit E-selectins and CXCR4 chemokine receptors, and uses thereof are disclosed.

BACKGROUND OF THE INVENTION

A number of cancers are treatable before the cancer has moved beyond the primary site. However, once the cancer has spread beyond the primary site, the treatment options may be limited and the survival statistics may decline dramatically. Bones are a common location for cancer to infiltrate once leaving the primary tumor location. Breast and prostate cancer are examples of cancers that migrate to bones. Even leukemic cells that arise in the bloodstream may home to the bone marrow. Once cancer resides in bone, it may cause pain in an individual. Furthermore, once in the bone marrow, the cancer cells may also become resistant to chemotherapy. In addition, if the particular bone affected produces blood cells in the bone marrow, the individual may develop a variety of blood cell related disorders. Thus, it may be desirable to prevent cancer cells from leaving the primary site and/or to prevent extravasation of cancer cells from the bloodstream and infiltration into other tissues. Retention of cancer cells in the bloodstream makes the cells more susceptible to treatment, such as chemotherapy.

Some cancers originate all or in part in bone. For such cancers, it may be desirable to mobilize cancer cells from bone to the bloodstream and/or to prevent those cells (as well as any cancer cells already in the bloodstream) from homing to bone or otherwise leaving the bloodstream. Retention of cancer cells in the bloodstream (or mobilization of cancer cells into the bloodstream and then retention therein) makes the cells more susceptible to treatment, such as chemotherapy.

Hematopoietic stem cells (HSCs) also reside in the bone marrow and are a source of material for cellular therapy. HSCs adhere to the stroma within the bone marrow and in order to be harvested must break these adhesions and mobilize out of the bone marrow. Improved agents for increasing the number of HSCs available for harvesting may be desirable. Such HSCs may be useful for engraftment.

Accordingly, there is a need in the art for the treatment of cancers that may leave the primary site and cancers that originate all or in part in bone, and for improved methods to aid in the preparation of therapeutic-grade stem cells. The present disclosure may fulfill one or more of these needs and/or may provide other advantages.

SUMMARY OF THE INVENTION

Briefly stated, compounds, compositions, and methods for treating diseases and for improving methods in which an E-selectin and a CXCR4 chemokine receptor may play a role are disclosed. Compounds disclosed herein are heterobifunctional, wherein an E-selectin inhibitor is linked to a CXCR4 chemokine receptor inhibitor. The compounds may be used to treat cancer in which the cancer cells may leave the primary site, to treat an inflammatory disease in which the adhesion or migration of cells occurs in the disease, and/or to release cells such as stem cells (e.g., bone marrow progenitor cells) into circulating blood and enhance retention of the cells in the blood (e.g., to mobilize cells out of bone marrow and maintain the cells in the peripheral bloodstream).

In some embodiments, heterobifunctional inhibitors of Formula (I) are disclosed:

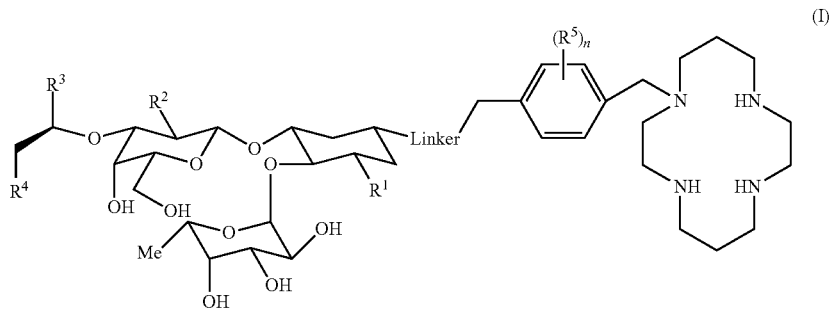

prodrugs of Formula (I), and pharmaceutically acceptable salts of any of the foregoing, wherein $R^1$ is chosen from H, $C_{1-8}$ alkyl, $C_{2-8}$ alkenyl, $C_{2-8}$ alkynyl, $C_{1-8}$ haloalkyl, $C_{2-8}$ haloalkenyl, and $C_{2-8}$ haloalkynyl groups;

$R^2$ is chosen from —OH, —NH$_2$, —OC(=O)Y$^1$, —NHC(=O)Y$^1$, and —NHC(=O)NHY$^1$ groups, wherein $Y^1$ is chosen from $C_{1-8}$ alkyl, $C_{2-8}$ alkenyl, $C_{2-8}$ alkynyl, $C_{1-8}$ haloalkyl, $C_{2-8}$ haloalkenyl, $C_{2-8}$ haloalkynyl, $C_{6-18}$ aryl, and $C_{1-13}$ heteroaryl groups;

$R^3$ is chosen from —CN, —CH$_2$CN, and —C(=O)Y$^2$ groups, wherein $Y^2$ is chosen from $C_{1-8}$ alkyl, $C_{2-8}$ alkenyl, $C_{2-8}$ alkynyl, —OZ$^1$, —NHOH, —NHOCH$_3$, —NHCN, and —NZ$^1$Z$^2$ groups, wherein $Z^1$ and $Z^2$, which may be identical or different, are independently chosen from H, $C_{1-8}$ alkyl, $C_{2-8}$ alkenyl, $C_{2-8}$ alkynyl, $C_{1-8}$ haloalkyl, $C_{2-8}$ haloalkenyl, and $C_{2-8}$ haloalkynyl groups, wherein $Z^1$ and $Z^2$ may join together to form a ring;

R[4] is chosen from $C_{3-8}$ cycloalkyl groups;

R[5] is independently chosen from H, halo, $C_{1-8}$ alkyl, $C_{2-8}$ alkenyl, $C_{2-8}$ alkynyl, $C_{1-8}$ haloalkyl, $C_{2-8}$ haloalkenyl, and $C_{2-8}$ haloalkynyl groups, with the proviso that at least one R[5] is not H;

n is chosen from integers ranging from 1 to 4; and

Linker is chosen from linker groups.

As used herein, 'compound of Formula (I)' includes heterobifunctional inhibitors of Formula (I), pharmaceutically acceptable salts of heterobifunctional inhibitors of Formula (I), prodrugs of heterobifunctional inhibitors of Formula (I), and pharmaceutically acceptable salts of prodrugs of heterobifunctional inhibitors of Formula (I).

In some embodiments, pharmaceutical compositions comprising at least one compound of Formula (I) and optionally at least one additional pharmaceutically acceptable ingredient are presented.

In some embodiments, a compound of Formula (I) and/or a pharmaceutical composition comprising at least one compound of Formula (I) may be used for the preparation and/or manufacture of a medicament for use in treating at least one of the diseases, disorders, and conditions described herein.

In some embodiments, a method for treatment and/or prevention of at least one cancer in which the cancer cells may leave the primary site is disclosed, the method comprising administering to a subject in need thereof an effective amount of at least one compound of Formula (I) and/or a pharmaceutical composition comprising at least one compound of Formula (I) and optionally at least one additional pharmaceutically acceptable ingredient.

In some embodiments, a method for treatment and/or prevention of at least one cancer in which it is desired to mobilize cancer cells from a site into the bloodstream and/or retain the cancer cells in the bloodstream is disclosed, the method comprising administering to a subject in need thereof an effective amount of at least one compound of Formula (I) and/or a pharmaceutical composition comprising at least one compound of Formula (I) and optionally at least one additional pharmaceutically acceptable ingredient.

In some embodiments, at least one compound of Formula (I) and/or a pharmaceutical composition comprising at least one compound of Formula (I) may be used in methods described herein for treatment and/or prevention of tumor metastasis. In some embodiments, the tumor metastasis arises from pancreatic cancer. In some embodiments, the tumor metastasis arises from prostate cancer. In some embodiments, the tumor metastasis arises from pancreatic cancer. In some embodiments, the tumor metastasis arises from breast cancer. In some embodiments, at least one additional chemotherapy agent such as gemcitabine is administered to the individual.

In some embodiments, a method for releasing cells into circulating blood and enhancing retention of the cells in the blood comprising administering to a subject in need thereof an effective amount of at least one compound of Formula (I) and/or a pharmaceutical composition comprising at least one compound of Formula (I) and optionally at least one additional pharmaceutically acceptable ingredient is disclosed. In some embodiments, the method further includes collecting the released cells. In some embodiments, collecting the released cells utilizes apheresis. In some emobdiments, the released cells are stem cells (e.g., bone marrow progenitor cells). In some embodiments, G-CSF is administered to the individual.

In some embodiments, a method for the treatment and/or prevention of an inflammatory disease is presented in which the adhesion and/or migration of cells occurs in the diseases comprising administering to a subject in need thereof an effective amount of at least one compound of Formula (I) and/or a pharmaceutical composition comprising at least one compound of Formula (I) and optionally at least one additional pharmaceutically acceptable ingredient.

In the following description, certain specific details are set forth in order to provide a thorough understanding of various embodiments. However, one skilled in the art will understand that the disclosed embodiments may be practiced without these details. In other instances, well-known structures have not been shown or described in detail to avoid unnecessarily obscuring descriptions of the embodiments. These and other embodiments will become apparent upon reference to the following detailed description and attached drawings.

BRIEF DESCRIPTION OF THE DRAWINGS

FIG. 9 depicts the results of an intratibial tumor assay by heterobifunctional Compound 9.

DETAILED DESCRIPTION

Figure 1A:
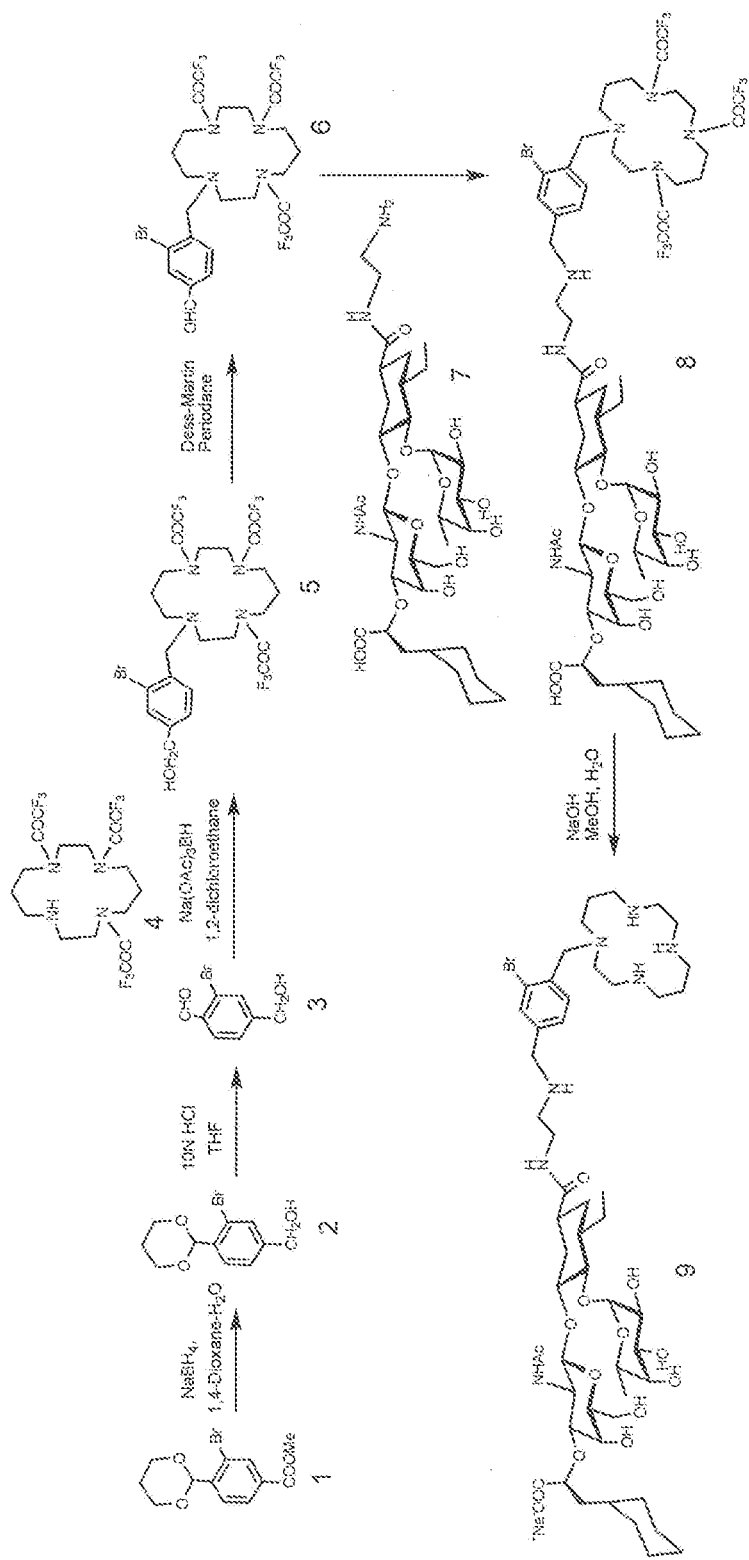
FIG. 1 (FIG. 1A and FIG. 1B) is a diagram illustrating the synthesis of heterobifunctional Compound 9 and Compound 16.

Disclosed herein are compounds, compositions, and methods for treating diseases in which an E-selectin and a CXCR4 chemokine receptor play a role, and for enhancing retention of cells after releasing into circulating blood. The compounds have a variety of uses in vitro and in vivo.

E-selectin inhibitors are known in the art. Some E-selectin inhibitors are specific for E-selectin only. Other E-selectin inhibitors have the ability to inhibit not only E-selectin but additionally P-selectin or L-selectin or both P-selectin and L-selectin. Examples of E-selectin inhibitors (specific for E-selectin or otherwise) are disclosed in U.S. Pat. No. 7,060,685; U.S. Application Publication No. US-2007-0054870; U.S. Application Publication No. US-2008-0161546; and references cited in any of these patent or published application documents. Those examples are small organic molecules. Other known E-selectin inhibitors are amino acid-based, such as antibodies. For example, the humanized monoclonal antibody CDP850 is an E-selectin inhibitor.

CXCR4 chemokine receptor inhibitors are known in the art. Such inhibitors will typically prevent the binding of stromal derived factor-1 (SDF-1) to a CXCR4 receptor. Examples of CXCR4 chemokine receptor inhibitors are AMD-3100 (Hendrix et al., Antimicrob. Agents Chemother. 44: 1667-1673, 2000); ALX40-4C (Doranz et al., AIDS Research and Human Retroviruses 17: 475-486, 2001): and T134 (Arakaki et al., J. Virol. 73: 1719-1723, 1999). These examples include a small organic molecule and amino acid-based molecules, such as the T22 peptide. AMD-3100 is a bicyclam. Each of the two cyclam rings is attached to the same phenyl ring (each cyclam ring is para to the other) via a methylene group.

Heterobifunctional compounds for inhibition of E-selectin and the CXCR4 chemokine receptor comprising E-selectin inhibitor-Linker-CXCR4 chemokine receptor inhibitor are known in the art. Examples are disclosed, for example, in U.S. Pat. No. 8,410,066.

In some embodiments, presented are heterobifunctional inhibitors of Formula (I):

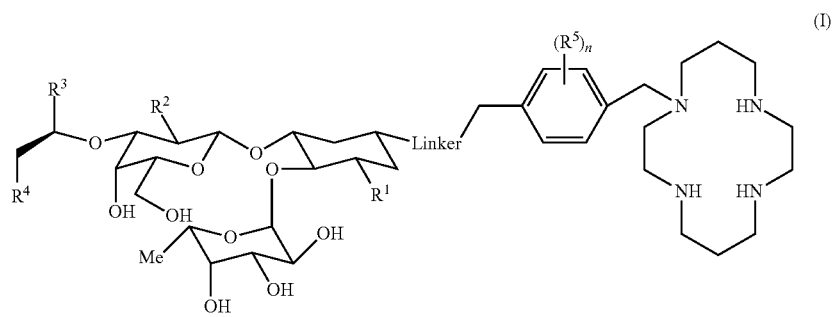

prodrugs of Formula (I), and pharmaceutically acceptable salts of any of the foregoing, wherein $R^1$ is chosen from H, $C_{1-8}$ alkyl, $C_{2-8}$ alkenyl, $C_{2-8}$ alkynyl, $C_{1-8}$ haloalkyl, $C_{2-8}$ haloalkenyl, and $C_{2-8}$ haloalkynyl groups;

$R^2$ is chosen from —OH, —$NH_2$, —OC(=O)$Y^1$, —NHC(=O)$Y^1$, and —NHC(=O)NH$Y^1$ groups, wherein $Y^1$ is chosen from $C_{1-8}$ alkyl, $C_{2-8}$ alkenyl, $C_{2-8}$ alkynyl, $C_{1-8}$ haloalkyl, $C_{2-8}$ haloalkenyl, $C_{2-8}$ haloalkynyl, $C_{6-18}$ aryl, and $C_{1-13}$ heteroaryl groups;

$R^3$ is chosen from —CN, —$CH_2$CN, and —C(=O)$Y^2$ groups, wherein $Y^2$ is chosen from $C_{1-8}$ alkyl, $C_{2-8}$ alkenyl, $C_{2-8}$ alkynyl, —O$Z^1$, —NHOH, —NHOCH$_3$, —NHCN, and —$Z^1Z^2$ groups, wherein $Z^1$ and $Z^2$, which may be identical or different, are independently chosen from H, $C_{1-8}$ alkyl, $C_{2-8}$ alkenyl, $C_{2-8}$ alkynyl, $C_{1-8}$ haloalkyl, $C_{2-8}$ haloalkenyl, and $C_{2-8}$ haloalkynyl groups, wherein $Z^1$ and $Z^2$ may join together to form a ring;

$R^4$ is chosen from $C_{3-8}$ cycloalkyl groups;

each $R^5$ is independently chosen from H, halo, $C_{1-8}$ alkyl, $C_{2-8}$ alkenyl, $C_{2-8}$ alkynyl, $C_{1-8}$ haloalkyl, $C_{2-8}$ haloalkenyl, and $C_{2-8}$ haloalkynyl groups, with the proviso that at least one $R^5$ is not H;

n is chosen from integers ranging from 1 to 4; and

Linker is chosen from linker groups.

In some embodiments, $R^1$ is chosen from H, $C_{1-4}$ alkyl, and $C_{1-4}$ haloalkyl groups. In some embodiments, $R^1$ is chosen from H, methyl, ethyl, —$CH_2$F, —$CHF_2$, —$CH_2CH_2$F, —$CH_2CHF_2$, and —$CH_2CF_3$. In some embodiments, $R^1$ is H. In some embodiments, $R^1$ is chosen from methyl and ethyl. In some embodiments, $R^1$ is methyl. In some embodiments, $R^1$ is ethyl.

In some embodiments, $R^2$ is chosen from —OC(=O)$Y^1$ and —NHC(=O)$Y^1$ groups, wherein $Y^1$ is chosen from $C_{1-8}$ alkyl, $C_{1-8}$ haloalkyl, $C_{6-18}$ aryl, and $C_{1-13}$ heteroaryl groups. In some embodiments, $R^2$ is chosen from

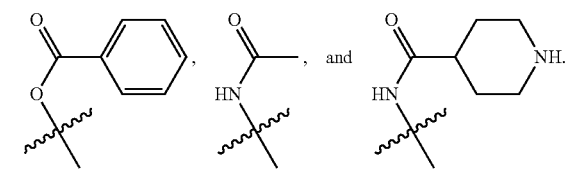

In some embodiments, $R^3$ is —C(=O)$Y^2$, wherein $Y^2$ is chosen from —O$Z^1$ and —N$Z^1Z^2$ groups, wherein $Z^1$ and $Z^2$, which may be identical or different, are independently chosen from H, $C_{1-8}$ alkyl, and $C_{1-8}$ haloalkyl, wherein $Z^1$ and $Z^2$ may join together to form a ring. In some embodiments, $R^3$ is —C(=O)OH.

In some embodiments, $R^4$ is chosen from cyclopropyl and cyclohexyl groups. In some embodiments, $R^4$ is chosen from

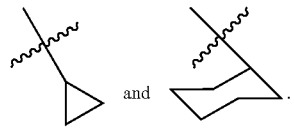

In some embodiments, each $R^5$ is independently chosen from H, halo, $C_{1-8}$ alkyl, and $C_{1-8}$ haloalkyl groups, with the proviso that at least one $R^5$ is not H. In some embodiments, at least one $R^5$ is halo. In some embodiments, at least one $R^5$ is fluoro. In some embodiments, at least one $R^5$ is chloro. In some embodiments, at least one $R^5$ is bromo. In some embodiments, at least one $R^5$ is iode.

In some embodiments, n is 2. In some embodiments, n is 2 and $R^5$ is halo. In some embodiments, n is 2 and $R^5$ is bromo. In some embodiments, n is 1. In some embodiments, n is 1 and $R^5$ is halo. In some embodiments, n is 1 and $R^5$ is bromo.

In some embodiments, the compound is chosen from compounds of Formula (Ia):
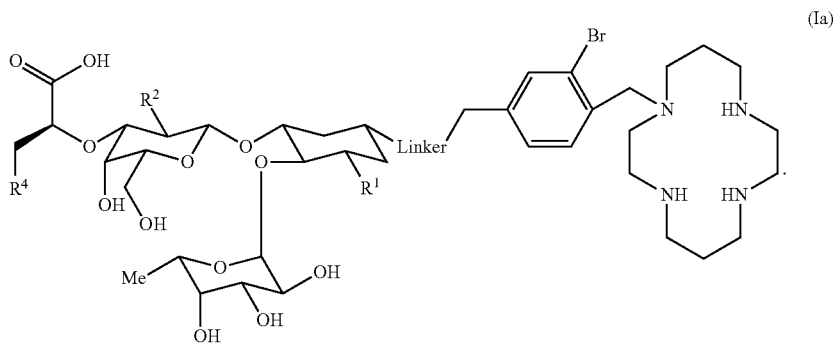
In some embodiments, the compound is chosen from compounds of the following Formulae:
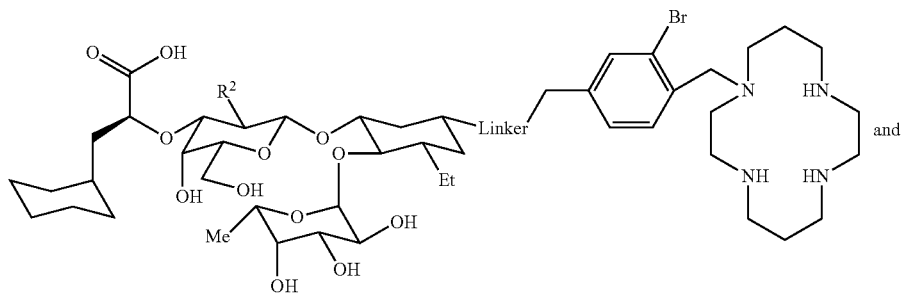
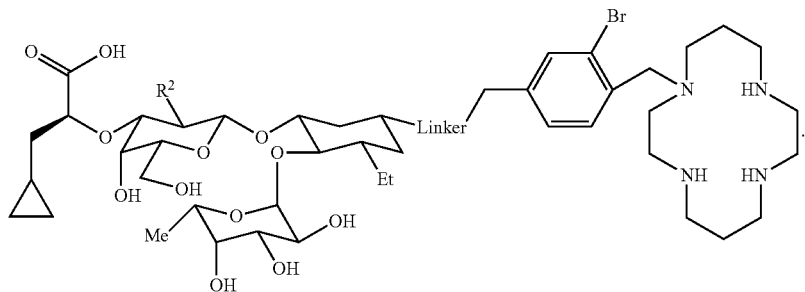
In some embodiments, the compound is chosen from compounds of Formula (Ib):
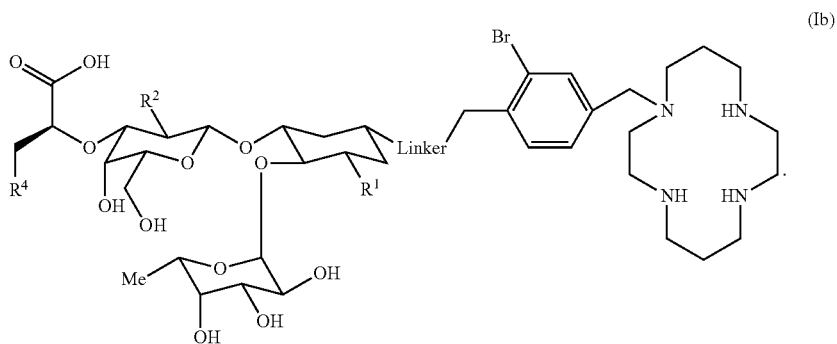

In some embodiments, the compound is chosen from compounds of the following Formulae:
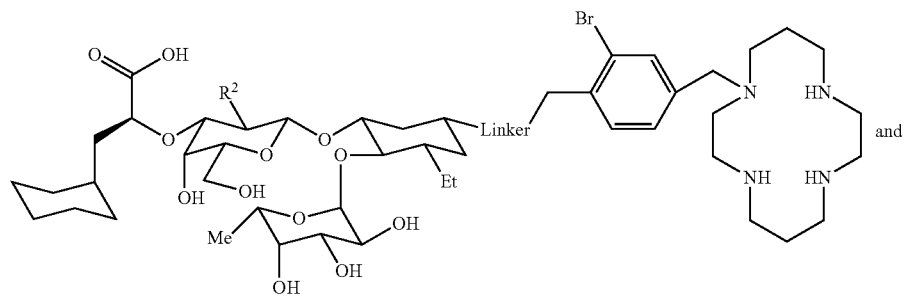
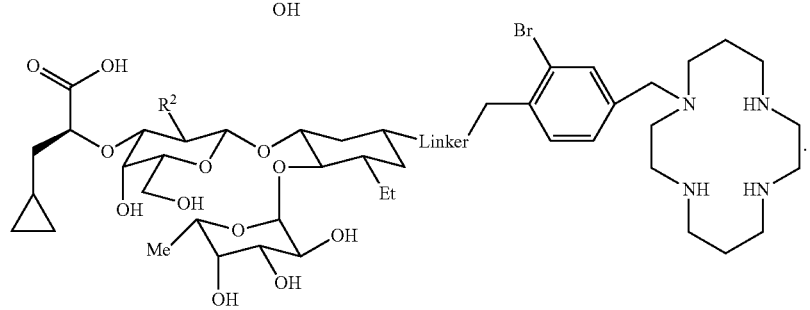
In some embodiments, the compound is chosen from compounds of the following Formulae:
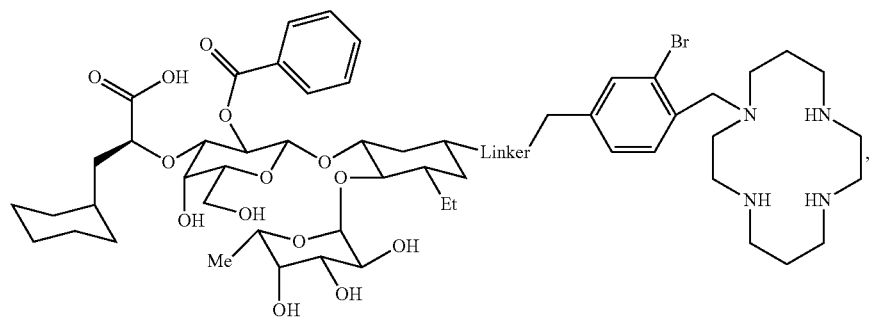
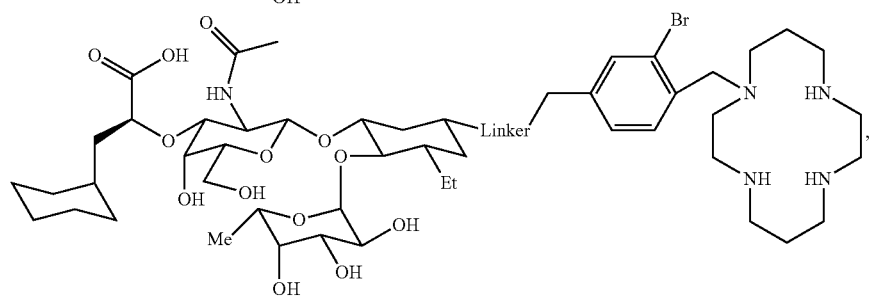
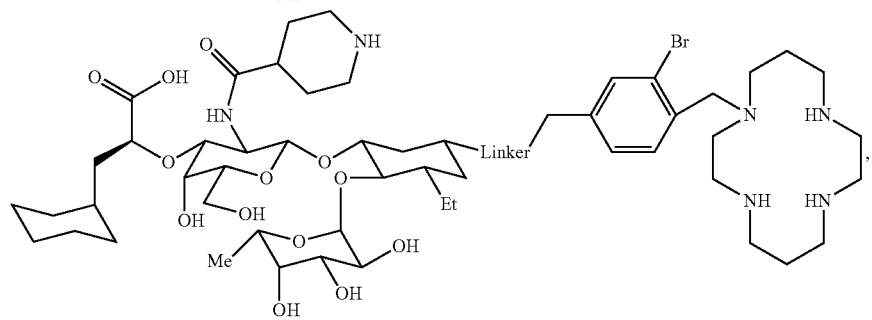

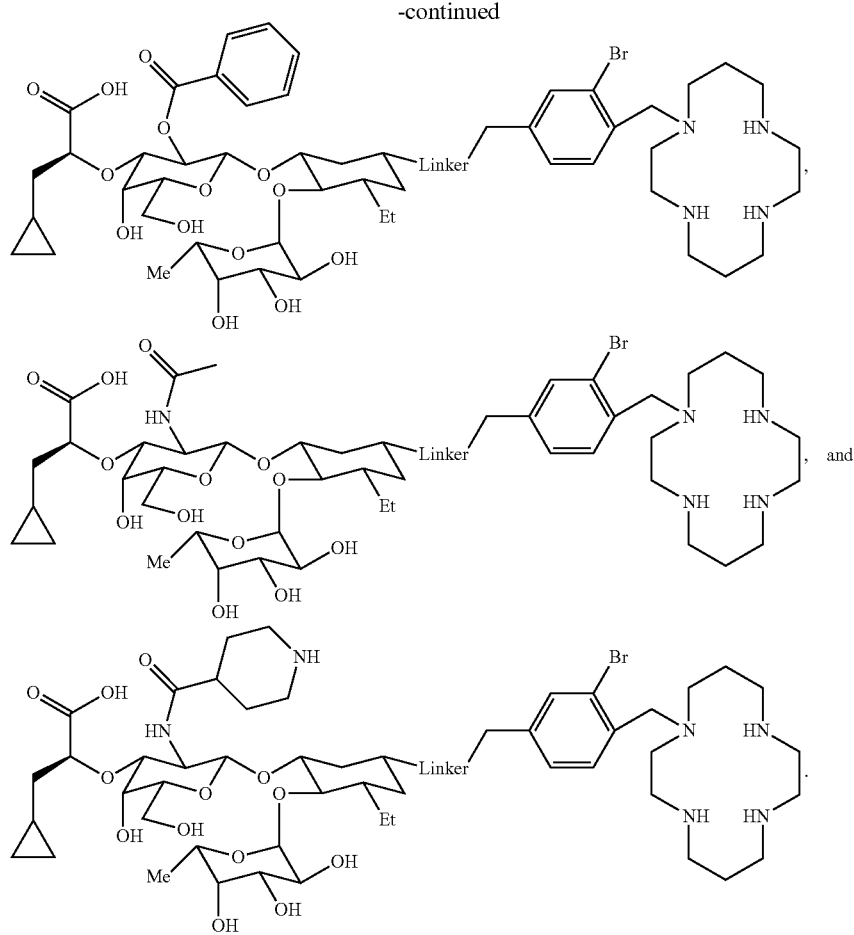
In some embodiments, the compound is chosen from compounds of the following Formulae:
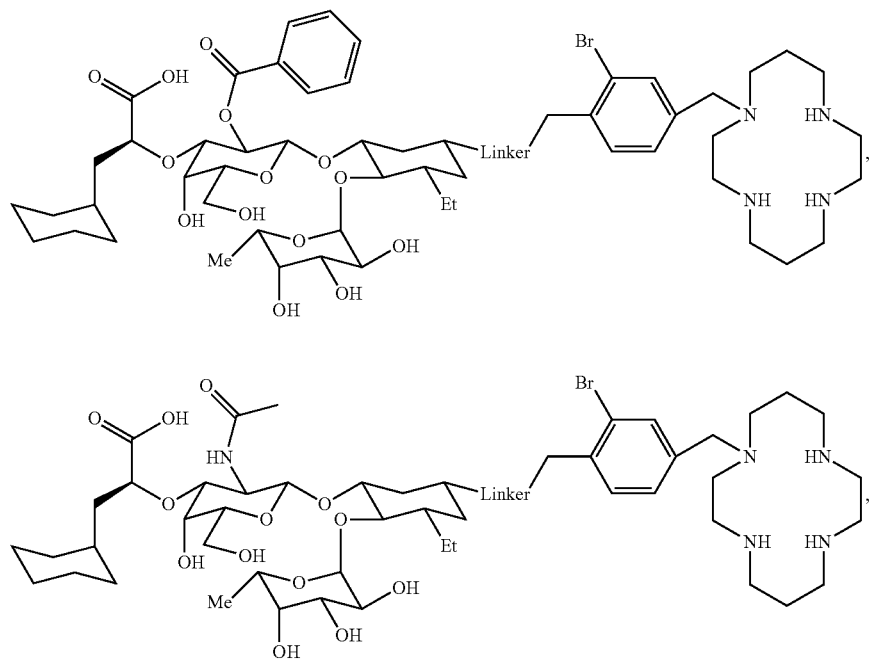

-continued

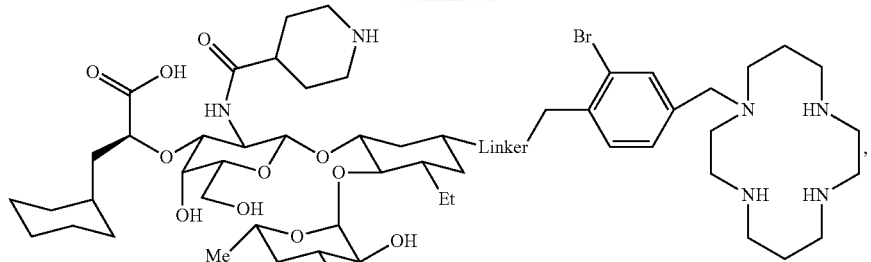

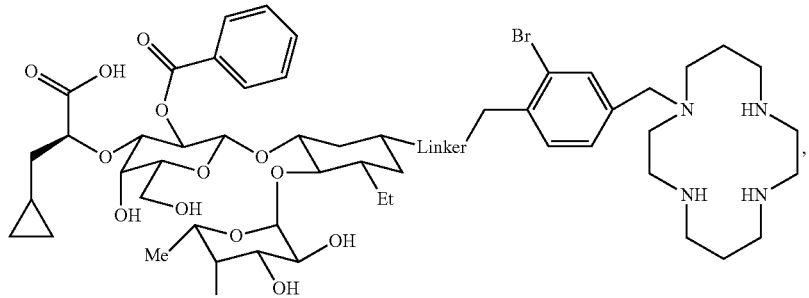

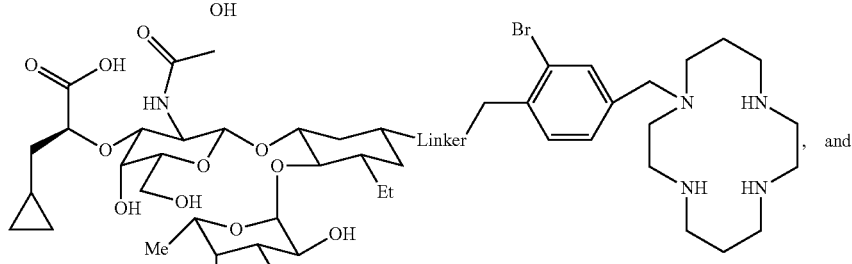

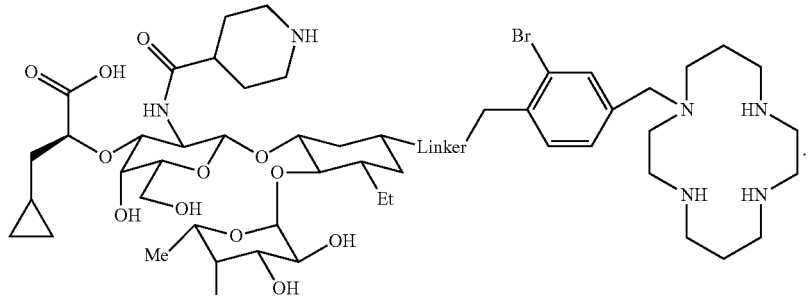

In some embodiments, linker groups may be chosen from groups comprising spacer groups, such spacer groups as, for example, —(CH$_2$)$_p$— and —O(CH$_2$)$_p$—, wherein p is chosen from integers ranging from 1 to 20. Other non-limiting examples of spacer groups include carbonyl groups and carbonyl-containing groups such as, for example, amide groups. A non-limiting example of a spacer group is

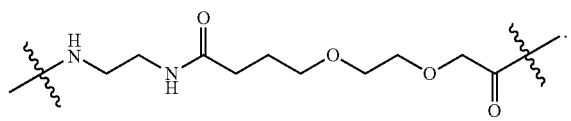 [SMILES: *NCCNC(=O)CCCOCCOCC(*)=O]

In some embodiments, the linker group is chosen from

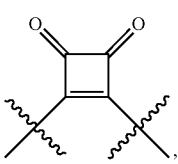 , 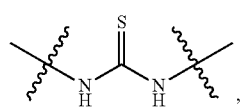 ,

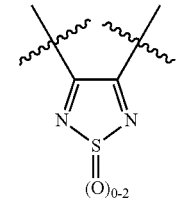 , 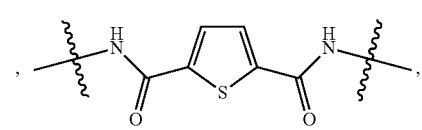 .

-continued

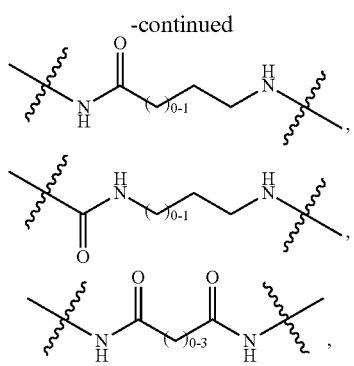

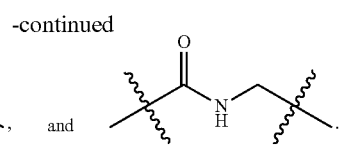

Other linker groups, such as, for example, polyethylene glycols (PEGS) and —C(=O)—NH—(CH$_2$)$_p$—C(=O)—NH—, wherein p is chosen from integers ranging from 1 to 20, will be familiar to those of ordinary skill in the art and/or those in possession of the present disclosure.

In some embodiments, the linker group is

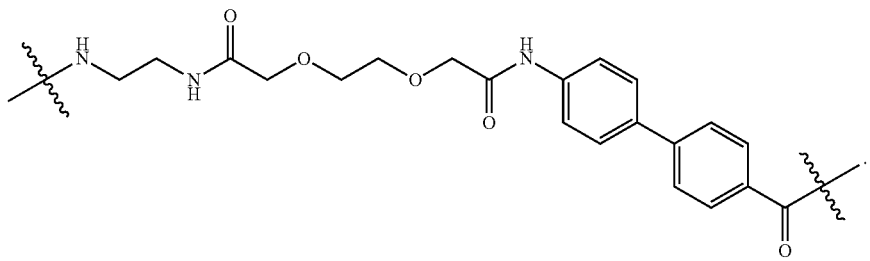 [SMILES: *NCCNC(=O)COCCOCC(=O)Nc1ccc(-c2ccc(C(*)=O)cc2)cc1]

In some embodiments, the linker group is

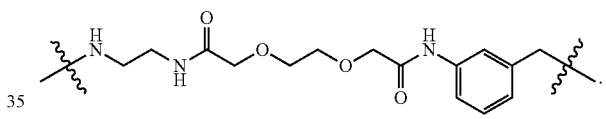

In some embodiments, the linker group is chosen from —C(=O)NH(CH$_2$)$_2$NH—, —CH$_2$NHCH$_2$—, and —C(=O)NHCH$_2$—. In some embodiments, the linker group is —C(=O)NH(CH$_2$)$_2$NH—.

In some embodiments, the compound is chosen from compounds of the following Formulas:

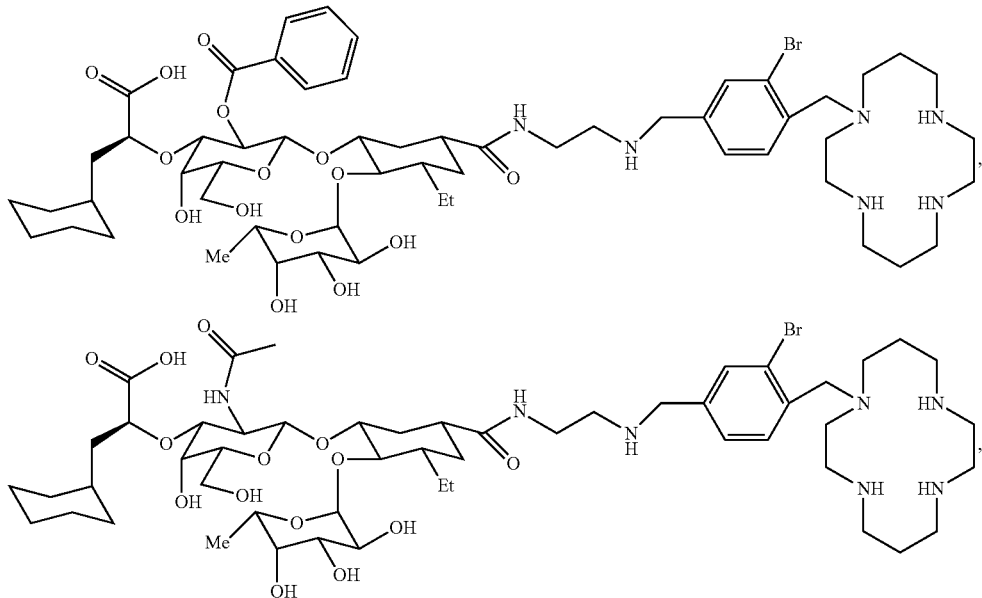

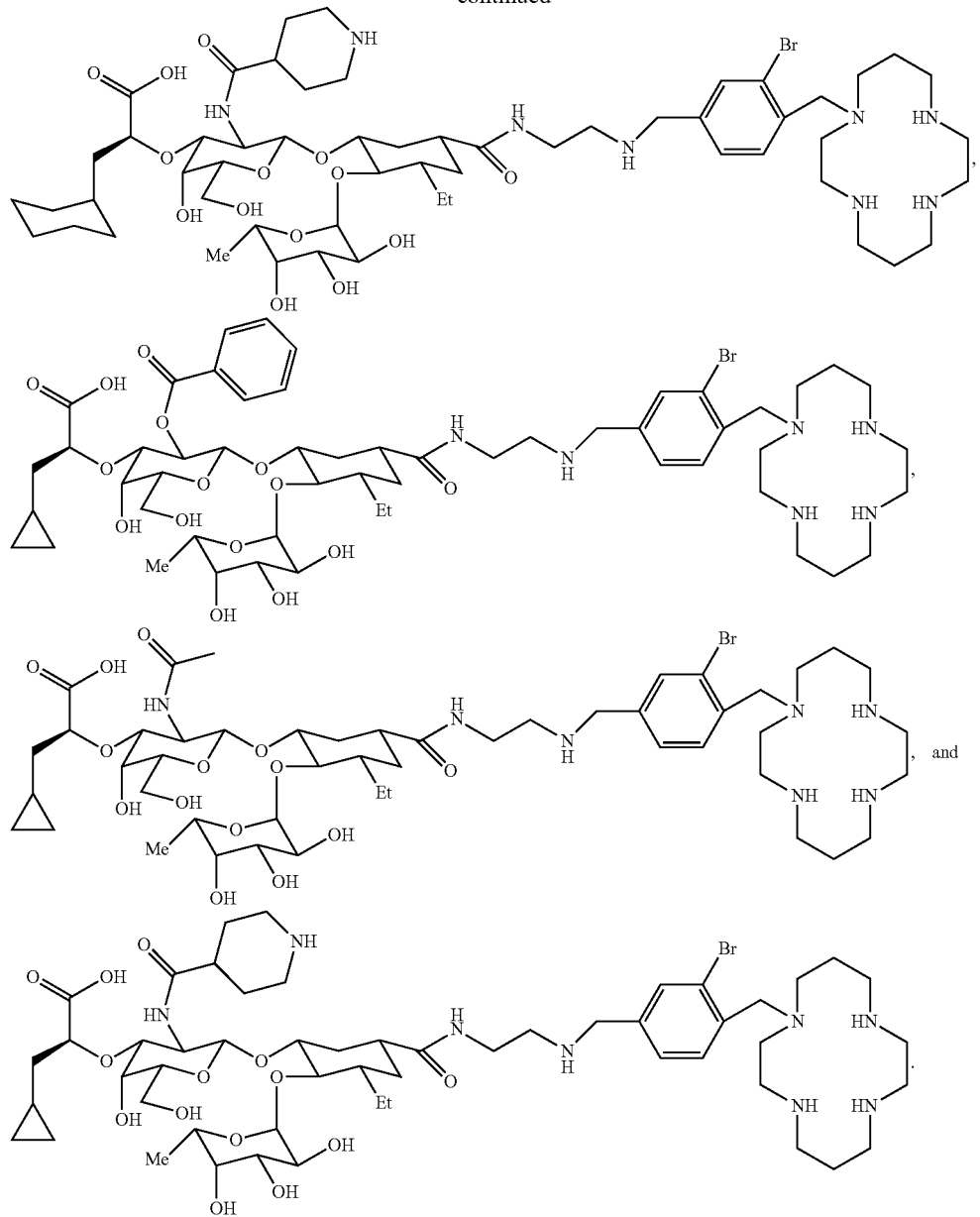
In some embodiments, the compound is chosen from compounds of the following Formulae:
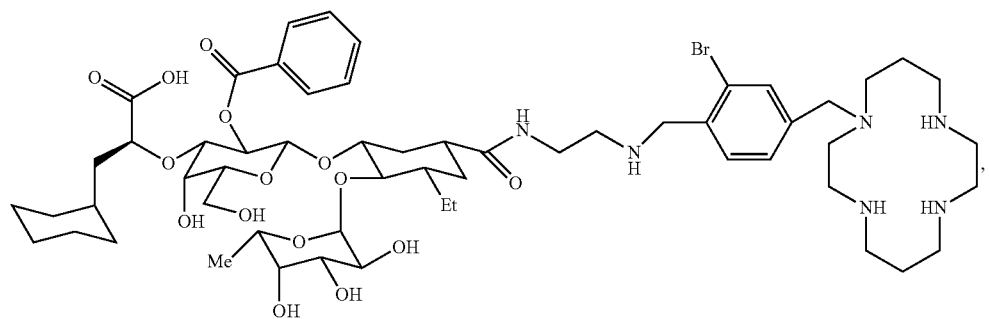

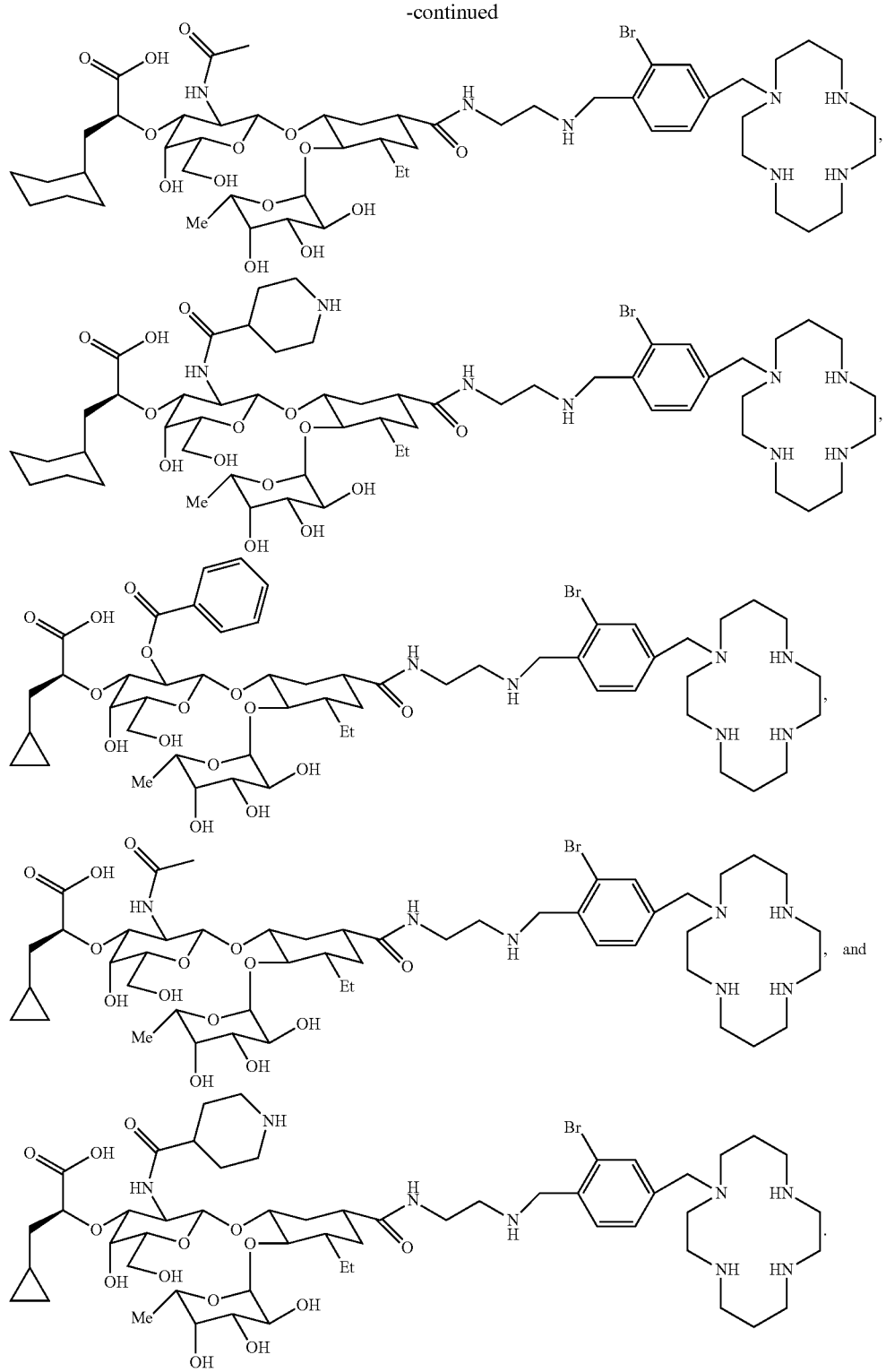

Also provided are pharmaceutical compositions comprising at least one compound of Formula (I). Such pharmaceutical compositions are described in greater detail herein. These compounds and compositions may be used in the methods described herein.

In some embodiments, at least one compound of Formula (I) and/or a pharmaceutical composition comprising at least one compound of Formula (I) may be used in methods described herein for treatment and/or prevention of a cancer in which the cancer cells may leave the primary site. A primary site may be, for example, solid tissue (e.g., breast, prostate, or pancreatic) or the bloodstream.

In addition to breast cancer, prostate cancer, and pancreatic cancer, other examples of infiltrating diseases include lung cancer and melanoma, as well as the hematological malignancies (e.g., leukemias and myelomas). As used herein, the term "treatment" (including variations such as "treating") includes for the disease or a complication associated with the disease. For example, a complication associated with the cancer may not have presented itself in an individual with the disease, and a compound may be administered to prevent presentation of the complication in the individual. Complications associated with a cancer in which the cancer cells may leave the primary site include, for example, metastasis and infiltration of cancer cells to other tissues. For example, acute myelogenous leukemia (AML) and multiple myeloma (MM) cells migrate to the endosteal region of the bone marrow where the cells become quiescent and are protected from chemotherapy-induced apoptosis. Administration of a compound described herein may prevent adhesion or migration of cancer cells. Such prevention can result in making the cancer cells more susceptible to treatment with chemotherapy. Administration of a compound described herein in the context of prevention may be to an individual who is at risk of occurrence of a cancer for the first time, or for recurrence of a cancer. For example, while a brain cancer such as glioblastoma multiforme is typically treated with another type of therapy (such as radiation or chemotherapy) for the first occurrence, such therapy is usually not effective to prevent recurrence.

In some embodiments, at least one compound of Formula (I) and/or a pharmaceutical composition comprising at least one compound of Formula (I) may be used in methods described herein for treatment and/or prevention of a cancer in which it is desired to mobilize cancer cells from a site into the bloodstream and retain the cancer cells in the bloodstream.

Examples of cancers for such treatment include leukemias and myelomas (e.g., AML and MM). Mobilizing cancer cells into the bloodstream from a site and retaining the cells therein can result in making the cancer cells more susceptible to treatment with chemotherapy. An example of a site from which to mobilize cancer cells is bone. Cancer cells may, for example, be in circulation and then home to bone. Once in bone, the cancer cells are protected from chemotherapy. A compound described herein may be used, for example, to mobilize cancer cells from bone into the bloodstream and prevent cancer cells from homing to bone, thereby retaining the cancer cells in the bloodstream. Administration of a compound described herein in the context of prevention may be to an individual who is at risk of occurrence of a cancer for the first time, or for recurrence of a cancer. For example, while a brain cancer such as glioblastoma multiforme is typically treated with another type of therapy (such as radiation or chemotherapy) for the first occurrence, such therapy is usually not effective to prevent recurrence.

In some embodiments, at least one compound of Formula (I) and/or a pharmaceutical composition comprising at least one compound of Formula (I) may be used in methods for relaxing cells (cush as hematopoietic stem cells) into circulating blood and enhancing retention of the cells in the blood.

One use of the method is, for example, for stem cell harvesting. Stem cells may be needed, for example, after high-dose chemotherapy treatment. Many chemotherapies suppress bone marrow which disrupts the production of certain components of blood in an individual. As a result, the individual may develop a variety of blood cell related disorders and continuation of chemotherapy may be compromised. A compound described herein may be used, for example, to release stem cells into circulating blood and enhance retention of the stem cells in the blood. The method may include a further step of collecting cells that are released. For example, released stem cells may be collected. A variety of techniques are known in the art for collecting cells. For example, apheresis may be utilized. An example of a stem cells is a bone marrow progenitor cell. The release of such cells from bone marrow into circulating blood and retention therein has a variety of uses. For example, the mobilized bone marrow progenitor cells may be collected from the blood. A use of such collected cells is to obtain healthy bone marrow progenitor cells from an individual prior to treatment of the individual in a manner such that bone marrow is suppressed. Following treatment, the individual can receive a bone marrow transplantation utilizing the bone marrow progenitor cells collected prior to treatment. This is useful, for example, where an individual needs to be subjected to a chemotherapy protocol that will suppress bone marrow.

It can be desirable to additionally treat an individual with at least one (i.e., one or more) colony stimulating factor. Such a factor may be administered, for example, before or simultaneous with administration of at least one of the above-described compounds. Where administration is simultaneous, the combination may be administered from a single container or two (or more) separate containers. An example of a suitable colony stimulating factor is granulocyte-colony stimulating factor (G-CSF). G-CSF induces the bone marrow to grow and produce more stem cells. A compound described herein aids in releasing stem cells into circulating blood. Stem cells produced in bone marrow and released into circulating blood, as a result of the combination of the administration (separately or together) of a compound described herein and G-CSF, may be collected as described above. Such collected stem cells may be, for example, administered to the individual after chemotherapy. The stem cells return to the bone marrow and produce blood cells. Application of a compound described herein to mobilization and harvesting of healthy bone marrow progenitor cells from bone marrow treated with G-CSF provides cells useful, for example, for bone marrow transplantation.

In some embodiments, at least one compound of Formula (I) and/or a pharmaceutical composition comprising at least one compound of Formula (I) may be used in methods described herein for treatment and/or prevention of tumor metastasis. In some embodiments, the tumor metastasis arises from pancreatic cancer. In some emobidments, the tumor metastasis arises from prostate cancer. In some embodiments, the tumor metastasis arises from pancreatic cancer. In some embodiments, the tumor metastasis arises from breast cancer. In some embodiments, at least one additional chemotherapy agent such as gemcitabine is administered to the individual.

In some embodiments, at least one compound of Formula (I) and/or a pharmaceutical composition comprising at least one compound of Formula (I) may be used in methods for treatment and/or prevention of an inflammatory disease in which the adhesion or migration of cells occurs in the disease.

Examples of inflammatory diseases include inflammatory skin disorders such as atopic dermatitis and psoriasis. The treatment may reduce (partially or totally) the disease or a complication associated therewith, such as pain. The treatment may be used in conjunction with one or more other therapies for such an inflammatory disease or a complication associated therewith.

In some embodiments, a compound of Formula (I) and/or a pharmaceutical composition comprising at least one compound of Formula (I) may be used for treating at least one of the diseases, disorders, and conditions described herein or for the preparation or manufacture of a medicament for use in treating at least one of the diseases, disorders, and/or conditions described herein. Each of these methods and uses is described in greater detail.

Definitions

Whenever a term in the specification is identified as a range (e.g., $C_{1-4}$ alkyl), the range independently discloses and includes each element of the range. As a non-limiting example, $C_{1-4}$ alkyls includes, independently, $C_1$ alkyls, $C_2$ alkyls, $C_3$ alkyls, and $C_4$ alkyls.

The term "at least one" refers to one or more, such as one, two, etc. For example, the term "at least one $C_{1-4}$ alkyl" refers to one or more $C_{1-4}$ alkyl groups, such as one $C_{1-4}$ alkyl group, two $C_{1-4}$ alkyl groups, etc.

The term "alkyl" includes saturated straight, branched, and cyclic (also identified as cycloalkyl), primary, secondary, and tertiary hydrocarbon groups. Non-limiting examples of alkyl groups include methyl, ethyl, propyl, isopropyl, cyclopropyl, butyl, secbutyl, isobutyl, tertbutyl, cyclobutyl, 1-methylbutyl, 1,1-dimethylpropyl, pentyl, cyclopentyl, isopentyl, neopentyl, cyclopentyl, hexyl, isohexyl, and cyclohexyl. Unless stated otherwise specifically in the specification, an alkyl group may be optionally substituted.

The term "alkenyl" includes straight, branched, and cyclic hydrocarbon groups comprising at least one double bond. The double bond of an alkenyl group can be unconjugated or conjugated with another unsaturated group. Non-limiting examples of alkenyl groups include vinyl, allyl, butenyl, pentenyl, hexenyl, butadienyl, pentadienyl, hexadienyl, 2-ethylhexenyl, and cyclopent-1-en-1-yl. Unless stated otherwise specifically in the specification, an alkenyl group may be optionally substituted.

The term "alkynyl" includes straight and branched hydrocarbon groups comprising at least one triple bonds. The triple bond of an alkynyl group can be unconjugated or conjugated with another unsaturated group. Non-limiting examples of alkynyl groups include ethynyl, propynyl, butyryl, pentynyl, and hexynyl. Unless stated otherwise specifically in the specification, an alkynyl group may be optionally substituted.

The term "aryl" includes hydrocarbon ring system group comprising 6 to 18 carbon ring atoms and at least one aromatic ring. The aryl group may be a monocyclic, bicyclic, tricyclic or tetracyclic ring system, which may include fused or bridged ring systems. Non-limiting examples of aryl groups include aryl groups derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group may be optionally substituted.

The term "arylalkyl" or "aralkyl" includes aryl groups, as described herein, appended to the parent molecular moiety through an alkyl group, as defined herein. Non-limiting examples of an arylalkyl or aralkyl group include benzyl, phenethyl, and diphenylmethyl. Unless stated otherwise specifically in the specification, an arylalkyl or aralkyl group may be optionally substituted.

The term "cycloalkyl" or "carbocyclic ring" includes saturated monocyclic or polycyclic hydrocarbon group, which may include fused or bridged ring systems. Non-limiting examples of a cycloalkyl group include cyclopropyl, cyclobutyl, cyclopentyl, cyclohexyl, cycloheptyl, cyclooctyl, adamantyl, and norbornyl. Unless otherwise stated specifically in the specification, a cycloalkyl group may be optionally substituted.

The term "E-selectin antagonist" includes inhibitors of E-selectin only, as well as inhibitors of E-selectin and either P-selectin car L-selectin, and inhibitors of E-selectin, P-selectin, and L-selectin.

The term "fused" includes any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

The term "halo" or "halogen" includes fluoro, chloro, bromo, and iodo.

The term "haloalkyl" includes alkyl groups, as defined herein, substituted by at least one halogen, as defined herein. Non-limiting examples include trifluoromethyl, difluoromethyl, trichloromethyl, 2,2,2-trifluoroethyl, 1,2-difluoroethyl, 3-bromo-2-fluoropropyl, and 1,2-dibromoethyl. A "fluoroalkyl" is a haloalkyl that is substituted with at least one fluoro group. Unless stated otherwise specifically in the specification, a haloalkyl group may be optionally substituted.

The term "haloalkenyl" includes alkenyl groups, as defined herein, substituted by at least one halogen, as defined herein. Non-limiting examples include fluoroethenyl, 1,2-difluoroethenyl, 3-bromo-2-fluoropropenyl, and 1,2-dibromoethenyl. A "fluoroalkenyl" is a haloalkenyl substituted with at least one fluoro group. Unless stated otherwise specifically in the specification, a haloalkenyl group may be optionally substituted.

The term "haloalkynyl" includes alkynyl groups, as defined herein, substituted by at least one halogen, as defined herein. Non-limiting examples include fluoroethynyl, 1,2-difluoroethynyl, 3-bromo-2-fluoropropynyl, and 1,2-dibromoethynyl. A "fluoroalkynyl" is a haloalkynyl substituted with at least one fluoro group. Unless stated otherwise specifically in the specification, a haloalkynyl group may be optionally substituted.

The term "heterocyclyl" or "heterocyclic ring" includes 3- to 18-membered saturated or partially unsaturated non-aromatic ring groups comprising 2 to 12 ring carbon atoms and 1 to 6 ring heteroatom(s) each independently chosen from N, O, and S. Unless stated otherwise specifically in the specification, the heterocyclyl groups may be a monocyclic, bicyclic, tricyclic or tetracyclic ring system, which may include fused or bridged ring systems; and the nitrogen, carbon or sulfur atoms in the heterocyclyl group may be optionally oxidized; the nitrogen atom may be optionally quaternized; and the heterocyclyl group may be partially or fully saturated. Non-limiting examples include dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group may be optionally substituted.

The term "heteroaryl" includes 5- to 14-membered ring groups comprising 1 to 13 ring carbon atoms and 1 to 6 ring heteroatom(s) each independently chosen from N, O, and S, and at least one aromatic ring. Unless stated otherwise specifically in the specification, the heteroaryl group may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Non-limiting examples include azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

The term "pharmaceutically acceptable salts" includes both acid and base addition salts. Non-limiting examples of pharmaceutically acceptable acid addition salts include chlorides, bromides, sulfates, nitrates, phosphates, sulfonates, methane sulfonates, formates, tartrates, maleates, citrates, benzoates, salicylates, and ascorbates. Non-limiting examples of pharmaceutically acceptable base addition salts include sodium, potassium, lithium, ammonium (substituted and unsubstituted), calcium, magnesium, iron, zinc, copper, manganese, and aluminum salts. Pharmaceutically acceptable salts may, for example, be obtained using standard procedures well known in the field of pharmaceuticals.

The term "prodrug" includes compounds that may be converted, for example, under physiological conditions or by solvolysis, to a biologically active compound described herein. Thus, the term "prodrug" includes metabolic precursors of compounds described herein that are pharmaceutically acceptable. A discussion of prodrugs can be found, for example, in Higuchi, T., et al., "Pro-drugs as Novel Delivery Systems," A.C.S. Symposium Series, Vol, 14, and in Bioreversible Carriers in Drug Design, ed. Edward B. Roche, American Pharmaceutical Association and Pergamon Press, 1987. The term "prodrug" also includes covalently bonded carriers that release the active compound(s) as described herein in vivo when such prodrug is administered to a subject. Non-limiting examples of prodrugs include ester and amide derivatives of hydroxy, carboxy, mercapto and amino functional groups in the compounds described herein.

The term "substituted" includes the situation where, in any of the above groups, at least one hydrogen atom is replaced by a non-hydrogen atom such as, for example, a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also includes the situation where, in any of the above groups, at least one hydrogen atom is replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles.

The term "thioalkyl" includes —$SR_a$ groups wherein $R_a$ is chosen from alkyl, alkenyl, and alkynyl groups, as defined herein. Unless stated otherwise specifically in the specification, a thioalkyl group may be optionally substituted.

The present disclosure includes within its scope all the possible geometric isomers, e.g., Z and E isomers (cis and trans isomers), of the compounds as well as all the possible optical isomers, e.g. diastereomers and enantiomers, of the compounds. Furthermore, the present disclosure includes in its scope both the individual isomers and any mixtures thereof, e.g. racemic mixtures. The individual isomers may be obtained using the corresponding isomeric forms of the starting material or they may be separated after the preparation of the end compound according to conventional separation methods. For the separation of optical isomers, e.g., enantiomers, from the mixture thereof conventional resolution methods, e.g. fractional crystallization, may be used.

The present disclosure includes within its scope all possible tautomers. Furthermore, the present disclosure includes in its scope both the individual tautomers and any mixtures thereof.

Compound Synthesis Procedures

Compounds of Formula (I) may be prepared according to General Reaction Schemes I and II below. It is understood that one of ordinary skill in the art may be able to make these compounds by similar methods or by combining other methods known to one of ordinary skill in the art. It is also understood that one of ordinary skill in the art would be able to make, in a similar manner as described below, other compounds of Formula (I) not specifically illustrated herein by using appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. and/or synthesized according to sources known to those of ordinary skill in the art (see, for example, Advanced Organic Chemistry: Reactions, Mechanisms, and Structure, 5th edition (Wiley, December 2000)) and/or prepared as described herein.

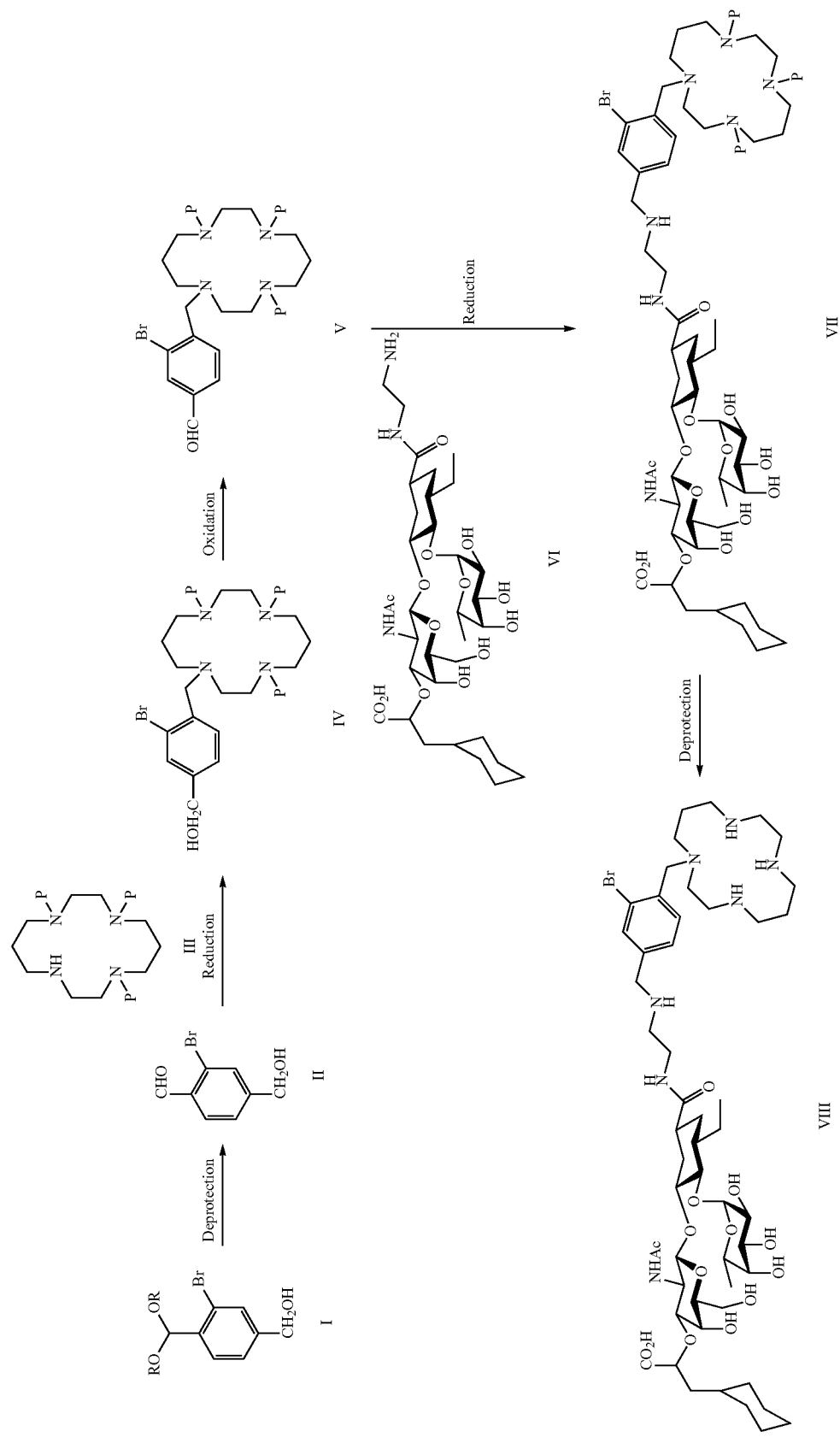

Deprotection of compound I gives brominated hydroxymethyl aldehyde II. Reductive amination with a suitably tri-protected cyclam generates compound IV. Oxidation gives aldehyde V which can be coupled to compound VI (WO 2013/096926) via reductive amination. Deprotection then gives a compound of the invention.

Alternatively, the regioisomeric bromide can be prepared according to Scheme II. Oxidation of compound I gives the aldehyde IX. Reductive amination with a suitably tri-protected cyclam gives intermediate X. Deprotection provides XI which can be coupled with compound VI via reductive amination to provide XIII. Deprotection then gives a compound of the invention.

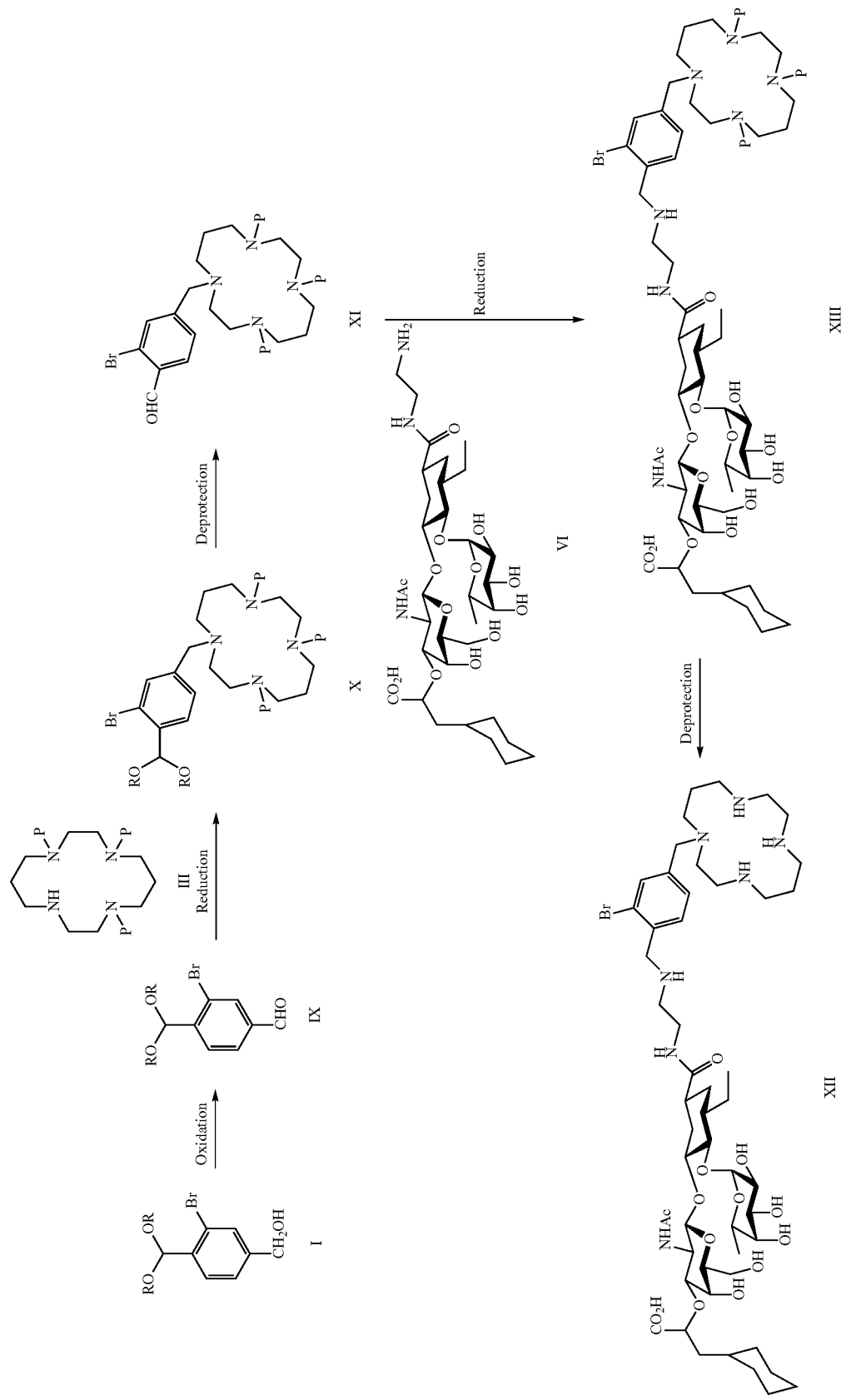

Those of ordinary skill in the art will understand that, in processes described herein, the functional groups of intermediate compounds may need to be protected by at least one suitable protecting group. Non-limiting examples of such functional groups include, hydroxyl groups, aldehyde groups, amino groups, mercapto groups, and carboxylic acid groups. Non-limiting examples of suitable protecting groups for hydroxy groups include trialkylsilyl and diarylalkylsilyl groups (for example, t-butyldimethylsilyl, t-butyldiphenylsilyl or trimethylsilyl), tetrahydropyranyl, and benzyl. Non-limiting examples of suitable protecting groups for aldehyde groups include 1,3-dioxanes and 1,3-dioxolanes. Non-limiting examples of suitable protecting groups for amino, amidino and guanidino include t-butoxycarbonyl, benzyloxycarbonyl, allyloxycarbonyl, and trifluoroacetyl groups. Non-limiting examples of suitable protecting groups for mercapto include -C(0)-R" (where R" is alkyl, aryl or arylalkyl), p-methoxybenzyl, and trityl groups. Non-limiting examples of suitable protecting groups for carboxylic acid include alkyl, aryl and arylalkyl esters. Protecting groups may be added or removed in accordance with standard techniques, which are known to one of ordinary skill in the art and as described herein. The use of protecting groups is, for example, described in detail in Green, T. W. and P. G. M. Wutz, Protective Groups in Organic Synthesis (1999), 3rd Ed., Wiley. As one of ordinary skill in the art would appreciate, the protecting group may also be a polymer resin such as a Wang resin, Rink resin or a 2-chlorotrityl-chloride resin.

Methods for Characterizing Heterobifuctional Compounds

Biological activity of a heterobifunctional compound described herein may be determined, for example, by performing at least one in vitro and/or in vivo study routinely practiced in the art and described herein or in the art. In vitro assays include without limitation binding assays, immunoassays, competitive binding assays and cell based activity assays.

An inhibition assay may be used to screen for antagonists of E-selectin. For example, an assay may be performed to characterize the capability of a compound described herein to inhibit (i.e., reduce, block, decrease, or prevent in a statistically or biologically significant manner) interaction of E-selectin with $sLe^a$ or $sLe^x$. The inhibition assay may be a competitive binding assay, which allows the determination of $IC_{50}$ values. By way of example, E-selectin/Ig chimera may be immobilized onto a matrix (e.g., a multi-well plate, which may be made from a polymer, such as polystyrene; a test tube, and the like); a composition may be added to reduce nonspecific binding (e.g., a composition comprising non-fat dried milk or bovine serum albumin or other blocking buffer routinely used by a person skilled in the art); the immobilized E-selectin may be contacted with the candidate compound in the presence of $sLe^a$ comprising a reporter group under conditions and for a time sufficient to permit $sLe^a$ to bind to the immobilized E-selectin; the immobilized E-selectin may be washed; and the amount of $sLe^a$ bound to immobilized E-selectin may be detected. Variations of such steps can be readily and routinely accomplished by a person of ordinary skill in the art.

An inhibition assay may be used to screen for antagonism of CXCR4 mediated chemotaxis. For example, an assay may be performed to measure the ability of a glycomimetic CXCR4 antagonist to inhibit migration of CCRF-CEM cells, which express CXCR4 on their cell surfaces, across a membrane toward the CXCR4 ligand CXCL12 (SDF-1α). By way of example. CCRF-CEM cells are human T lymphoblasts that express CXCR4 on the cell surface. The cells may be labeled with 3 uM Calcein AM to enable detection by fluorescence. The cells may be treated with a CXCR4 antagonist and placed into the upper chamber of a transwell insert. The transwells may be placed into the wells of a 24-well plate with each well containing 600 ul of RPMI 1640 plus 2% FBS and 50 ng/mL CXCL12 (SDF1α). The cells may be allowed to migrate across the membrane from the upper chamber into the lower chamber for 3 hours at 37° C. in 5% CO2. The transwell inserts may be removed from the 24-well plate and the fluorescence in the lower chambers measured using a Molecular Devices FlexStation 3 with an excitation wavelength of 485 nm and an emission wavelength of 538 nm.

Alternatively, an assay may be used to measure the ability of a glycomimetic CXCR4 antagonist to inhibit the binding of CXCL12 (SDF-1α) to CHO cells that have been genetically engineered to express CXCR4 on the cell surface. One skilled in the art may activate CXCR4 by ligand binding (CXCL12), causing Gi to dissociate from the CXCR4 complex. The activated CXCR4 may bind to adenylyl cyclase, thus inactivating it, resulting in decreased levels of intracellular cAMP. Intracellular cAMP is usually low, so the decrease of the low level of cAMP by a Gi-coupled receptor will be hard to detect. Forskolin is added to the CHO cells to directly activate adenylyl cyclase (bypassing all GPCRs), thus raising the level of cAMP in the cell, so that a Gi response can be easily observed. CXCL12 interaction with CXCR4 decreases the intracellular level of cAMP and inhibition of CXCL12 interaction with CXCR4 by a CXCR4 antagonist increases the intracellular cAMP level, which is measured by luminescence.

Alternatively, one skilled in the art may use an assay to measure the ability of a glycomimetic CXCR4 antagonist to block the binding of an anti-CXCR4 antibody to Jurkat cells, which express CXCR4 on the cell surface. Jurkat cells may be treated with a CXCR4 antagonist followed by a phycoerythrin-conjugated anti-CXCR4 antibody. The antibody may be allowed to bind to the cells for 1 hour at 4° C. The cells may be washed and the binding of the anti-CXCR4-PE antibody to the cells may be assessed by flow cytometry.

Conditions for a particular assay include temperature, buffers (including salts, cations, media), and other components that maintain the integrity of any cell used in the assay and the compound, which a person of ordinary skill in the art will be familiar and/or which can be readily determined. A person of ordinary skill in the art also readily appreciates that appropriate controls can be designed and included when performing the in vitro methods and in vivo methods described herein.

The source of a compound that is characterized by at least one assay and techniques described herein and in the art may be a biological sample that is obtained from a subject who has been treated with the compound. The cells that may be used in the assay may also be provided in a biological sample. A "biological sample" may include a sample from a subject, and may be a blood sample (from which serum or plasma may be prepared), a biopsy specimen, one or more body fluids (e.g., lung lavage, ascites, mucosal washings, synovial fluid, urine), bone marrow, lymph nodes, tissue explant, organ culture, or any other tissue or cell preparation from the subject or a biological source. A biological sample may further include a tissue or cell preparation in which the morphological integrity or physical state has been disrupted, for example, by dissection, dissociation, solubilization, fractionation, homogenization, biochemical or chemical extraction, pulverization, lyophilization, sonication, or any other means for processing a sample derived from a subject or biological source. In some embodiments, the subject or biological source may be a human or non-human animal, a primary cell culture (e.g., immune cells), or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, and the like.

As described herein, methods for characterizing heterobifunctional inhibitors include animal model studies. Non-limiting examples of animal models for liquid cancers used in the art include multiple myeloma (see, e.g., DeWeerdt, Nature 480:S38-S39 (15 Dec. 2011) doi: 10.1038/480S38a; Published online 14 Dec. 2011; Mitsiades et al., *Clin. Cancer Res.* 2009 15: 1210021 (2009)); acute myeloid leukemia (AML) (Zuher et al., *Genes Dev.* 2009 April 1; 23(7): 877-889). Animal models for acute lymphoblastic leukemia (ALL) have been used by persons of ordinary skill in the art for more than two decades. Numerous exemplary animal models for solid tumor cancers are routinely used and are well known to persons of ordinary skill in the art.

As understood by a person of ordinary skill in the medical art, the terms, "treat" and "treatment," include medical management of a disease, disorder, or condition of a subject (i.e., patient, individual) (see, e.g., Stedman's Medical Dictionary). In general, an appropriate dose and treatment regimen provide at least one of the compounds of the present disclosure in an amount sufficient to provide therapeutic and/or prophylactic benefit. For both therapeutic treatment and prophylactic or preventative measures, therapeutic and/or prophylactic benefit includes, for example, an improved clinical outcome, wherein the object is to prevent or slow or retard (lessen) an undesired physiological change or disorder, or to prevent or slow or retard (lessen) the expansion or severity of such disorder. As discussed herein, beneficial or desired clinical results from treating a subject include, but are not limited to, abatement, lessening, or alleviation of symptoms that result from or are associated with the disease, condition, or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival. "Treatment" can include prolonging survival when compared to expected survival if a subject were not receiving treatment. Subjects in need of treatment include those who already have the disease, condition, or disorder as well as subjects prone to have or at risk of developing the disease, condition, or disorder, and those in which the disease, condition, or disorder is to be prevented (i.e., decreasing the likelihood of occurrence of the disease, disorder, or condition).

In some embodiments of the methods described herein, the subject is a human. In some embodiments of the methods described herein, the subject is a non-human animal. A subject in need of treatment as described herein may exhibit at least one symptom or sequelae of the disease, disorder, or condition described herein or may be at risk of developing the disease, disorder, or condition. Non-human animals that may be treated include mammals, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

The effectiveness of the compounds of the present disclosure in treating and/or preventing a disease, disorder, or condition described herein can readily be determined by a person of ordinary skill in the medical and clinical arts. Determining and adjusting an appropriate dosing regimen (e.g., adjusting the amount of compound per dose and/or number of doses and frequency of dosing) can also readily be performed by a person of ordinary skill in the medical and clinical arts. One or any combination of diagnostic methods, including physical examination, assessment and monitoring of clinical symptoms, and performance of analytical tests and methods described herein, may be used for monitoring the health status of the subject.

Pharmaceutical Compositions and Methods of Using Pharmaceutical Compositions

Also provided herein are pharmaceutical compositions comprising at least one compound of Formula (I). In some embodiments, the pharmaceutical composition further comprises at least one additional pharmaceutically acceptable ingredient.

In pharmaceutical dosage forms, any one or more of the compounds of the present disclosure may be administered in the form of a pharmaceutically acceptable derivative, such as a salt, and/or it/they may also be used alone and/or in appropriate association, as well as in combination, with other pharmaceutically active compounds.

An effective amount or therapeutically effective amount refers to an amount of a compound of the present disclosure or a composition comprising at least one such compound that, when administered to a subject, either as a single dose or as part of a series of doses, is effective to produce at least one therapeutic effect. Optimal doses may generally be determined using experimental models and/or clinical trials. Design and execution of pre-clinical and clinical studies for each of the therapeutics (including when administered for prophylactic benefit) described herein are well within the skill of a person of ordinary skill in the relevant art. The optimal dose of a therapeutic may depend upon the body mass, weight, and/or blood volume of the subject. In general, the amount of at least one compound of Formula (I) as described herein, that is present in a dose, may range from about 0.01 µg to about 1000 µg per kg weight of the subject. The minimum dose that is sufficient to provide effective therapy may be used in some embodiments. Subjects may generally be monitored for therapeutic effectiveness using assays suitable for the disease or condition being treated or prevented, which assays will be familiar to those having ordinary skill in the art and are described herein. The level of a compound that is administered to a subject may be monitored by determining the level of the compound (or a metabolite of the compound) in a biological fluid, for example, in the blood, blood fraction (e.g., serum), and/or in the urine, and/or other biological sample from the subject. Any method practiced in the art to detect the compound, or metabolite thereof, may be used to measure the level of the compound during the course of a therapeutic regimen.

The dose of a compound described herein may depend upon the subject's condition, that is, stage of the disease, severity of symptoms caused by the disease, general health status, as well as age, gender, and weight, and other factors apparent to a person of ordinary skill in the medical art. Similarly, the dose of the therapeutic for treating a disease or disorder may be determined according to parameters understood by a person of ordinary skill in the medical art.

Pharmaceutical compositions may be administered in any manner appropriate to the disease or disorder to be treated as determined by persons of ordinary skill in the medical arts. An appropriate dose and a suitable duration and frequency of administration will be determined by such factors as discussed herein, including the condition of the patient, the type and severity of the patient's disease, the particular form of the active ingredient, and the method of administration. In general, an appropriate dose (or effective dose) and treatment regimen provides the pharmaceutical composition(s) as described herein in an amount sufficient to provide therapeutic and/or prophylactic benefit (for example, an improved clinical outcome, such as more frequent complete or partial remissions, or longer disease-free and/or overall survival, or a lessening of symptom severity or other benefit as described in detail above).

The pharmaceutical compositions described herein may be administered to a subject in need thereof by any one of several routes that effectively delivers an effective amount of the compound. Non-limiting suitable administrative routes include topical, oral, nasal, intrathecal, enteral, buccal, sublingual, transdermal, rectal, vaginal, intraocular, subconjunctival, sublingual, and parenteral administration, including subcutaneous, intravenous, intramuscular, intrasternal, intracavernous, intrameatal, and intraurethral injection and/or infusion.

The pharmaceutical composition described herein may be sterile aqueous or sterile non-aqueous solutions, suspensions or emulsions, and may additionally comprise at least one pharmaceutically acceptable excipient (i.e., a non-toxic material that does not interfere with the activity of the active ingredient). Such compositions may be in the form of a solid, liquid, or gas (aerosol). Alternatively, the compositions described herein may be formulated as a lyophilizate, or compounds described herein may be encapsulated within liposomes using technology known in the art. The pharmaceutical compositions may further comprise at least one additional pharmaceutical acceptable ingredient, which may be biologically active or inactive. Non-limiting examples of such ingredients include buffers (e.g., neutral buffered saline or phosphate buffered saline), carbohydrates (e.g., glucose, mannose, sucrose or dextrans), mannitol, proteins, polypeptides, amino acids (e.g., glycine), antioxidants, chelating agents (e.g., EDTA and glutathione), stabilizers, dyes, flavoring agents, suspending agents, and preservatives.

Any suitable excipient or carrier known to those of ordinary skill in the art for use in pharmaceutical compositions may be employed in the compositions described herein. Excipients for therapeutic use are well known, and are described, for example, in Remington: The Science and Practice of Pharmacy (Gennaro, 21$^{st}$ Ed. Mack Pub. Co., Easton, Pa. (2005)). In general, the type of excipient is selected based on the mode of administration, as well as the chemical composition of the active ingredient(s). Pharmaceutical compositions may be formulated for the particular mode of administration. For parenteral administration, pharmaceutical compositions may further comprise water, saline, alcohols, fats, waxes, and buffers. For oral administration, pharmaceutical compositions may further comprise at least one ingredient chosen, for example, from any of the aforementioned excipients, solid excipients and carriers, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose, and magnesium carbonate.

The pharmaceutical compositions (e.g., for oral administration or delivery by injection) may be in the form of a liquid. A liquid pharmaceutical composition may include, for example, at least one the following: a sterile diluent such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. In some embodiments, the pharmaceutical composition comprises physiological saline. In some embodiments, the pharmaceutical composition an injectable pharmaceutical composition, and in some embodiments, the injectable pharmaceutical composition is sterile.

For oral formulations, at least one of the compounds of the present disclosure can be used alone or in combination with at least one additive appropriate to make tablets, powders, granules and/or capsules, for example, those chosen from conventional additives, disintegrators, lubricants, diluents, buffering agents, moistening agents, preservatives, coloring agents, and flavoring agents. The pharmaceutical compositions may be formulated to include at least one buffering agent, which may provide for protection of the active ingredient from low pH of the gastric environment and/or an enteric coating. A pharmaceutical composition may be formulated for oral delivery with at least one flavoring agent, e.g., in a liquid, solid or semi-solid formulation and/or with an enteric coating.

Oral formulations may be provided as gelatin capsules, which may contain the active compound or biological along with powdered carriers. Similar carriers and diluents may be used to make compressed tablets. Tablets and capsules can be manufactured as sustained release products to provide for continuous release of active ingredients over a period of time. Compressed tablets can be sugar coated or film coated to mask any unpleasant taste and protect the tablet from the atmosphere, or enteric coated for selective disintegration in the gastrointestinal tract.

A pharmaceutical composition may be formulated for sustained or slow release. Such compositions may generally be prepared using well known technology and administered by, for example, oral, rectal or subcutaneous implantation, or by implantation at the desired target site. Sustained-release formulations may contain the active therapeutic dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active therapeutic contained within a sustained release formulation depends upon the site of implantation, the rate and expected duration of release, and the nature of the condition to be treated or prevented.

The pharmaceutical compositions described herein can be formulated as suppositories by mixing with a variety of bases such as emulsifying bases or water-soluble bases. The pharmaceutical compositions may be prepared as aerosol formulations to be administered via inhalation. The compositions may be formulated into pressurized acceptable propellants such as dichlorodifluoromethane, propane, nitrogen and the like.

The compounds of the present disclosure and pharmaceutical compositions comprising these compounds may be administered topically (e.g., by transdermal administration). Topical formulations may be in the form of a transdermal patch, ointment, paste, lotion, cream, gel, and the like. Topical formulations may include one or more of a penetrating agent or enhancer (also call permeation enhancer), thickener, diluent, emulsifier, dispersing aid, or binder. Physical penetration enhancers include, for example, electrophoretic techniques such as iontophoresis, use of ultrasound (or "phonophoresis"), and the like. Chemical penetration enhancers are agents administered either prior to, with, or immediately following administration of the therapeutic, which increase the permeability of the skin, particularly the stratum corneum, to provide for enhanced penetration of the drug through the skin. Additional chemical and physical penetration enhancers are described in, for example, Transdermal Delivery of Drugs, A. F. Kydonieus (ED) 1987 CRL Press; Percutaneous Penetration Enhancers, eds. Smith et al. (CRC Press, 1995); Lennerås et al., *J. Pharm. Pharmacol.* 54: 499-508 (2002); Karande et al., *Pharm. Res.* 19: 655-60 (2002); Vaddi et al., *Int. J. Pharm.* 91: 1639-51 (2002); Ventura et al., *J. Drug Target* 9: 379-93 (2001); Shokri et al., *Int. J. Pharm.* 228 (1-2): 99-107 (2001); Suzuki et al., *Biol. Pharm. Bull.* 24: 698-700 (2001); Alberti et al., *J. Control Release* 71; 319-27 (2001); Goldstein et al., *Urology* 57: 301-5 (2001); Kiijavainen et al., *Eur. J. Pharm. Sci.* 10; 97-102 (2000); and Tenjarla et al., *Int. J. Pharm.* 192: 147-58 (1999).

Kits comprising unit doses of at least one compound of the present disclosure, for example in oral or injectable doses, are provided. Such kits may include a container comprising the unit dose, an informational package insert describing the use and attendant benefits of the therapeutic in treating the pathological condition of interest, and/or optionally an appliance or device for delivery of the at least one compound or composition comprising the same,

EXAMPLES

Example 1

Heterobifunctional Inhibitor of E-Selectin AND CXCR4 Chemokine Receptor (Compounds 9 and 16)

Figure 1B:
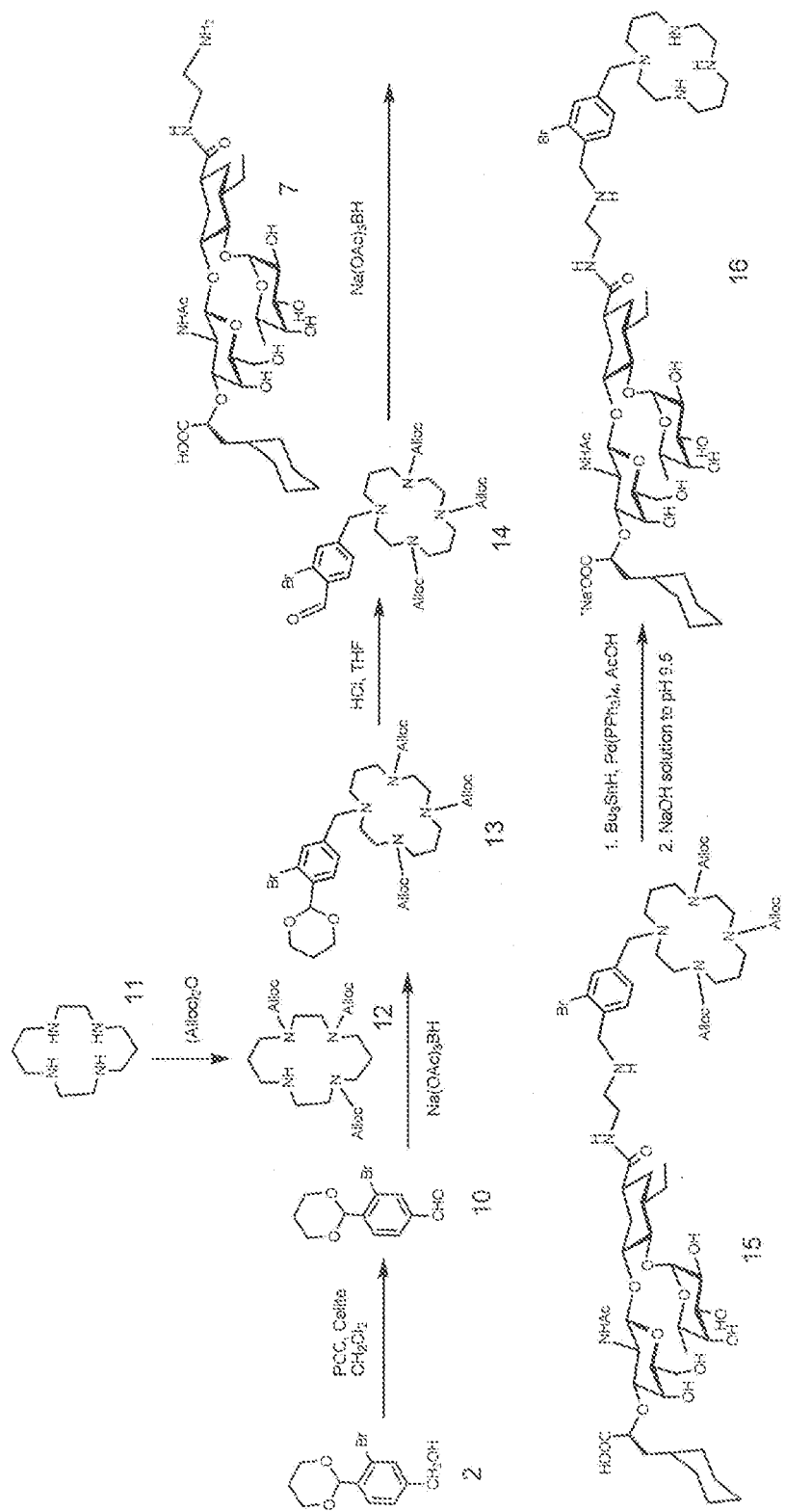
Figure 2:
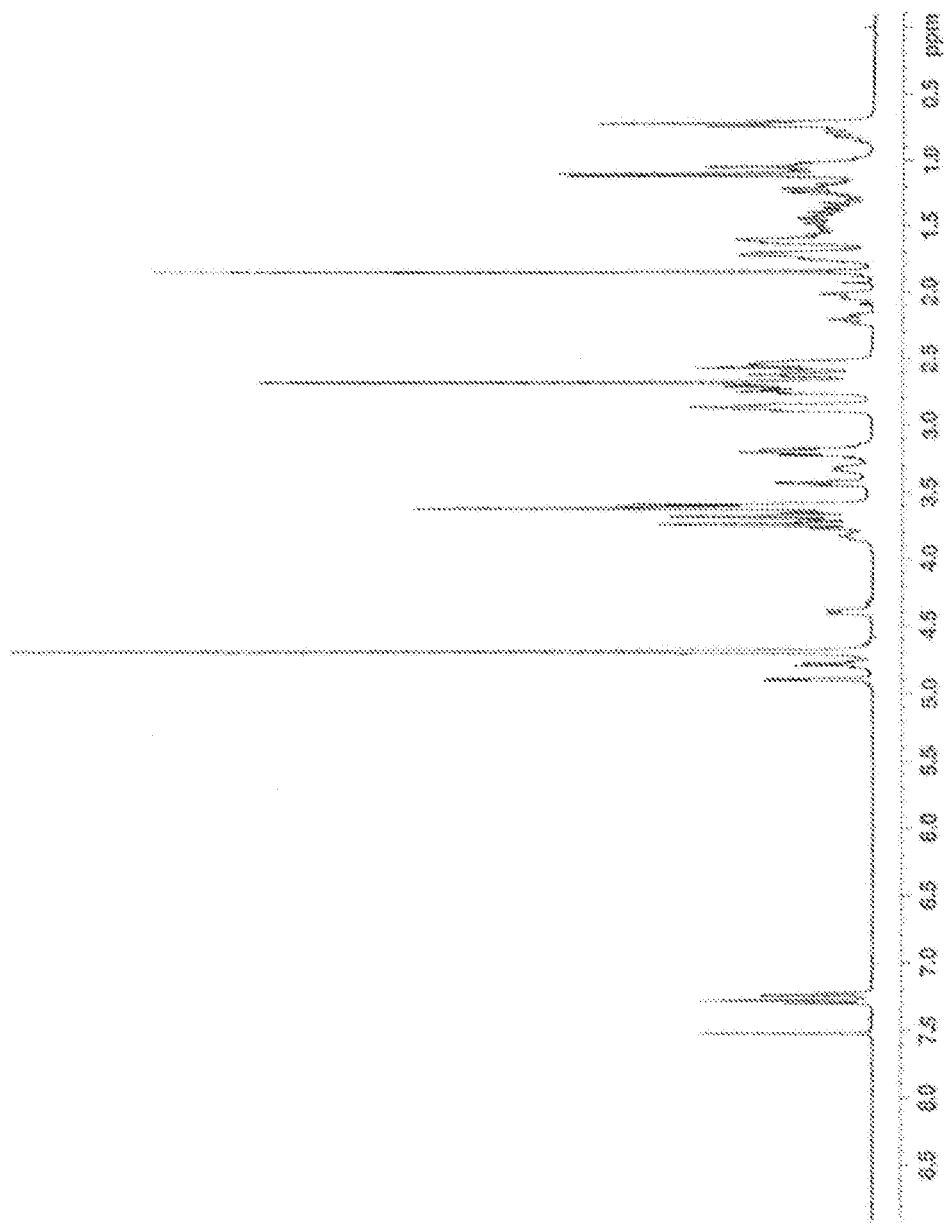
FIG. 2 shows the 400 MHz $^1$H NMR spectrum of Compound 9
Figure 3:
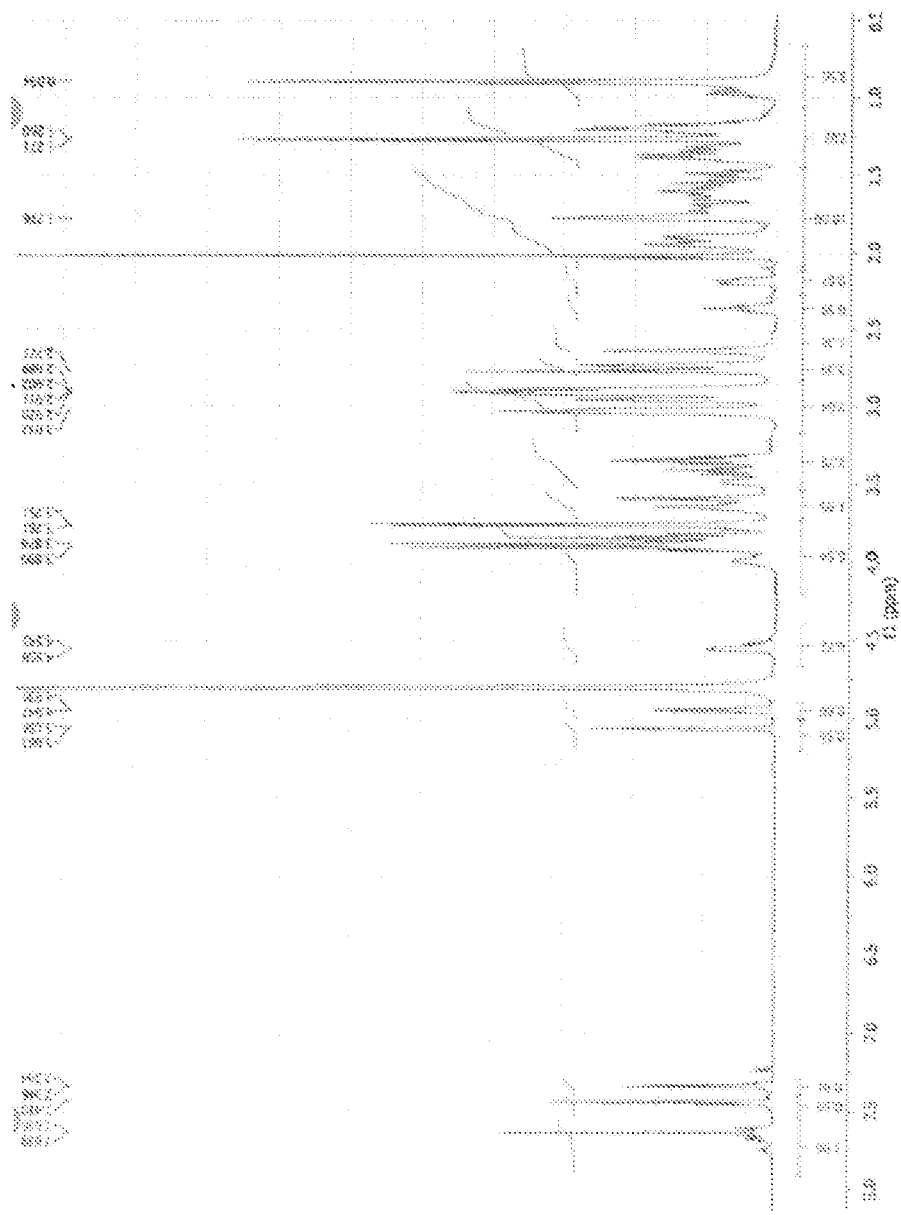
FIG. 3 shows the 600 MHz $^1$H NMR spectrum of Compound 16

Exemplary heterobifunctional compounds of Formula (I) were synthesized as described in Examples 1-2 and as shown in the exemplary synthesis schemes set forth in FIG. 1.

Synthesis of compound 2: Compound 1 (2.5 g, 8.3 mmol, Qian et al, Nature Communications, 2, 2011, 495) was dissolved in dioxane (30 ml) and $H_2O$ (20 ml) was added slowly with stirring at room temperature. The solution was cooled to 0° C. (ice bath) and $NaBH_4$ (3 g, 79.3 mmol) was added slowly with stirring. The reaction mixture was stirred at 64° C. for 16 h. The reaction mixture was cooled to 0° C. and quenched with 5N HCl. A solid mass precipitated out of solution which was removed by filtration. The filtrate was diluted with EtOAC (125 ml) and transferred to a separatory funnel. The phases were separated. The organic phase was washed with saline (100 ml), dried ($Na_2SO_4$), and concentrated. The residue was purified by column chromatography using hexanes-EtOAc as mobile phase to give compound 2 (1.8 g, 6.6 mmol, 79.3%).

Synthesis of compound 3: Compound 2 (1.7 g, 6.2 mmol) was dissolved in THF (32 ml) and 10N HCl (30 ml) was added with stirring at room temperature. The reaction mixture was stirred at room temperature 4.5 h. The reaction mixture was diluted with $H_2O$ (150 ml) and extracted with EtOAC (3×125 ml). Combined organic phases were with washed saturated solution of $NaHCO_3$ (1×125 ml) and brine (1×125 ml), dried ($Na_2SO_4$), filtered, and concentrated. The residue was purified by column chromatography using hexanes and EtOAc as mobile phase to give compound 3 (1.22 g. 5.7 mmol, 91.7%).

Synthesis of compound 5: A mixture of compound 4 (3.7 g, 7.58 mmol, Tetrahedron Letters, 2003, 44, 2481-2483) and compound 3 (2.05 g, 9.53 mmol) was co-evaporated with toluene (2×40 ml) and kept under vacuum for 30 min. The mixture was dissolved in 1, 2-dichloroethane, 40 ml) and stirred at room temperature for 30 min under argon, $Na(OAc)_3BH$ (3.2 g, 15 mmol) was added and the reaction mixture stirred overnight at room temperature under argon. Water (60 ml) was added followed by $CH_2Cl_2$ (80 ml). The reaction mixture was transferred to a seperatory funnel and organic phase was collected. Aqueous phase was washed with $CH_2Cl_2$ (2×60 ml). Combined organic phases were washed successively with cold saturated solution of $NaHCO_3$ (80 ml) and brine (80 ml), dried ($Na_2SO_4$), filtered, and concentrated. The residue was purified by column chromatography using Hexanes and EtOAc as mobile phase to give compound 5 (4.5 g, 6.54 mmol, 86.3%).

Synthesis of compound 6: Compound 5 (4.5 g, 6.54 mmol) was dissolved in $CH_2Cl_2$ (50 ml) under argon and cooled on an ice-bath. Dess-Martin reagent (3.6 g, 8.49 mmol) was added and the reaction mixture was stirred for 3 h under argon during which time the reaction mixture attained the room temperature slowly. The reaction mixture was diluted with $CH_2Cl_2$ (40 ml) and washed with cold saturated solution of $NaHCO_3$ and cold brine. Organic phase was dried ($Na_2SO_4$), filtered, and concentrated. The residue was purified by column chromatography using Hexanes-EtOAc as mobile phase to give compound 5 (3.6g, 5.25 mmol, 80.28%).

Synthesis of compound 8: A mixture of compound 6 (3.5 g, 5.11 mmol) and compound 7 (2.8 g, WO2013/096926) was co-evaporated with MeOH (3×50 ml) and dried under vacuum. The residue was dissolve in MeOH (50 ml) and stirred under argon for 1 h at room temperature. $Na(OAc)_3BH$ (3.6 g, 16.99 mmol) was added and the reaction mixture was stirred under argon for 17 h at room temperature. The reaction mixture was concentrated. The solid residue was suspended in $CHCl_3$ (100 ml), (250 ml) was added with stirring. The mixture was stirred for 10 min at room temperature during which time the solid product precipitated. The solid product was collected by filtration, washed with water, and dried under vacuum to give compound 8 (4.4 g, 3.14 mmol, 82.2% based on compound 6).

Synthesis of compound 9: To a solution of compound 8 (4.2 g, 3 mmol) in MeOH (100 ml) was added an aqueous solution of 1N NaOH (50 ml) with stirring at room temperature. The reaction mixture (pH 12.9) was stirred for 2 h at room temperature. The pH of resulting reaction mixture was adjusted to 8.9 by adding AcOH (3 ml). Solvent was evaporated off and then lyophilized. The solid mass was dissolve in $H_2O$ (20 ml) and pH of the solution was adjusted to 9.5 by adding NaOH solution. Desalting was performed by using pre-packed Sep-Pak C18 column (2×10 g) using $H_2O$ (150 ml each column), 50% MeOH in $H_2O$ (60 ml each column), 70% MeOH in $H_2O$ (100 ml each column), and 80% MeOH in $H_2O$ (50ml each column). Desired compound eluted in 50-80% MeOH in $H_2O$. They were combined and concentrated to ¼ of the total volume. The resulting solution was lyophilized to give compound 8 (2.9 g, 2.6 mmol, 86.7%). m/z calculated for $C_{52}H_{88}BrN_7O_{14}$ [M+H]: 1116.2; found: 1116.4.

Synthesis of compound 10: To a solution of compound 2 (0.225 g, 0.73 mmol) in $CH_2Cl_2$ was added Celite followed by pyridinium chlorochomate (0.28 g, 1.3 mmol) with stirring at room temperature. The reaction mixture was stirred at room temperature for 2 h and filtered through a bed of silica and celite. The filtrate was evaporated to dryness and purified by column chromatography to give compound 10 (0.2 g).

Synthesis of compound 12: To a suspension of cyclam (5 g, 25 mmol,) in anhydrous $CH_2Cl_2$ (150 ml) was added a solution of diallyldicarbonate (12 ml, d 0.991 g/ml, 83.7 mmol) in $CH_2Cl_2$ (100 ml) drop-wise with stirring. The reaction mixture was stirred at room temperature overnight during which the reaction turn light green and gave a clear solution. The solvent was removed and the residue was purified by column chromatography using $CH_2Cl_2$ and MeOH as mobile phase to give compound 12 (10.5 g, 23.2 mmol, 92.9%). TLC: $CH_2Cl_2$—MeOH (95:5).

Synthesis of compound 13: A solution of compound 10 (0.19 g, 0.7 mmol) and compound 12 (0.45 g, 1 mmol) in MeOH (1 ml and THF 0.5 ml) was stirred at room temperature for 30 min. To this solution was added $Na(OAc)_3BH$ (0.36 g, 1.6 mmol) and the reaction mixture was stirred room temperature for overnight. The solution was diluted with EtOAc and washed with $H_2O$. Organic layer was dried ($Na_2SO_4$), filtered, and concentrated to dryness. The residue was purified by column chromatography to give compound 13 (0.2 g).

Synthesis of compound 14: To a solution of compound 13 (0.24 g, 0.34 mmol) in THF (7 ml) was added concentrated HCl (5 ml) and the reaction mixture was stirred at room temperature for 10 h. The reaction mixture was diluted with $H_2O$ (20 ml) and extracted with EtOAc (3×16 ml). The combined organic phases were dried ($Na_2SO4$), filtered, and concentrated. The residue was purified by column chromatography to give compound 14 (0.15 g).

Synthesis of compound 15: A mixture of compound 7 (0.1 g, 0.14 mmol, WO2013/096926) and compound 14 (0.15 g, 0.23 mmol) in MeOH (1.5 ml) was stirred at room temperature for 30 min. followed by the addition of $Na(OAc)_3BH$ (0.096 g, 0.45 mmol). The reaction mixture was stirred at room temperature overnight. The reaction mixture was concentrated and the residue was suspended in MeOH. The resulting solid was removed by filtration and the filtrate was concentrated. The residue was purified by column chromatography to give compound 15 (35 mg).

Synthesis of compound 16: To a solution of compound 15 (0.028 g, 0.02 mmol) in $CH_2Cl_2$ (2 ml) was added AcOH (0.005 ml, 0.09 mmol) followed by $Pd(PPh_3)_4$ (0.003 g, 0.003 mmol) and $Bu_3SnH$ (0.017 ml, 0.06 mmol) and the reaction mixture was stirred at room temperature for 3 h. The reaction mixture was diluted with $CH_2Cl_2$ (10 ml) and extracted with $H_2O$ (8 ml). The aqueous layer was lyophilized, dissolved in $H_2O$ and purified by Sep-Pak C-18 Column. Fraction corresponding to the product was concentrated and dissolved in $H_2O$. The pH of the solution was adjusted 9.5 by a solution of NaOH and lyophilized to give compound 16 (6.5 mg) as Na-Salt. m/z calculated for $C_{52}H_{88}BrN_7O_{14}$ [M+H]: 1116.2; found: 1116.6

Example 2

CXCR4 Assay to Assess Inhibition of SDF-1 Induced Chemotaxis

Figure 4:
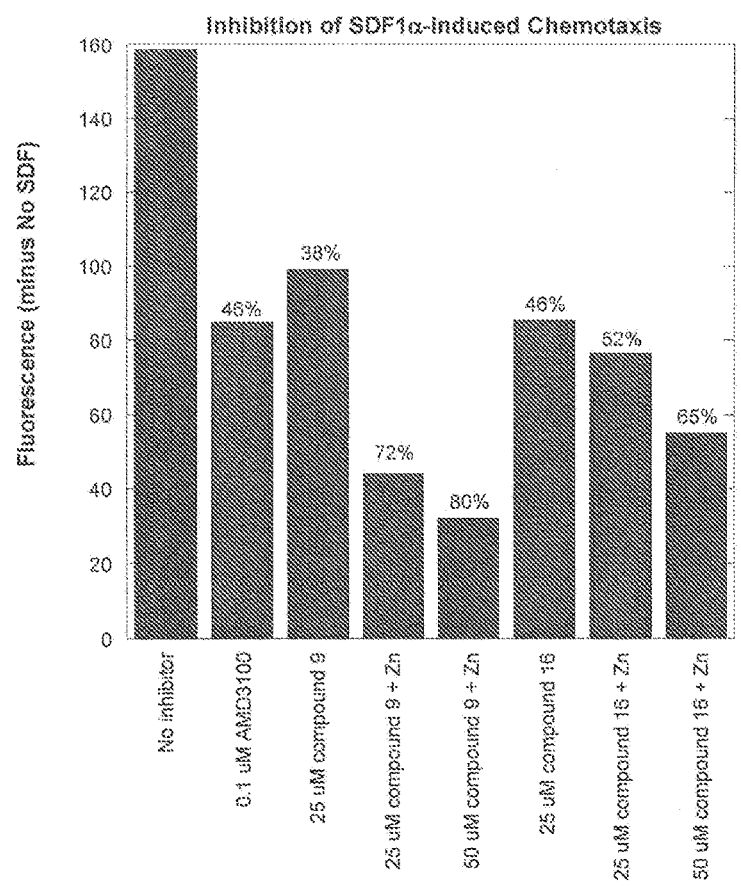
FIG. 4 depicts the results of the inhibition of SDF-1-induced chemotaxis assay by heterobifunctional Compounds 9 and 16.

A chemotaxis assay was used to measure the ability of a glycomimetic CXCR4 antagonist to inhibit migration of CCRF-CEM cells, which express CXCR4 on their cell surfaces, across a membrane toward the CXCR4 ligand CXCL12 (SDF-1α). CCRF-CEM cells are human T lymphoblasts that express CXCR4 on the cell surface. The cells were labeled with 3 uM Calcein AM for 15 minutes at 37° C. to enable detection by fluorescence. Subsequently, the cells were pelleted at 250×g for 10 minutes and resuspended to a final concentration of about $5\times10^5$ cells per mL in RPMI 1640 medium supplemented with 2% FBS. Typically, 200 ul of cells were mixed with 22 ul of a 10× concentration of the compound to be tested and placed at room temperature for 10 minutes. The treated cells were evaluated in duplicate, so 100 ul of the cells were placed into the upper chamber of each of two transwell inserts (Costar number 3421; 5.0 um pores; 6.5 mm diameter inserts). The transwells were place into the wells of a 24-well plate with each well containing 600 ul of RPMI 1640 plus 2% FBS and 50 ng/mL CXCL12. Negative control wells contained no CXCL12 in the lower chamber. The cells were allowed to migrate across the membrane from the upper chamber into the lower chamber for 3 hours at 37° C. in 5% $CO_2$. The transwell inserts were removed from the 24-well plate and the fluorescence in the lower chambers was measured using a Molecular Devices FlexStation 3 with an excitation wavelength of 485 nm and an emission wavelength of 538 nm. See FIG. 4.

Example 3

E-Selectin Activity—Binding Assay

The inhibition assay to screen and characterize antagonists of E-selectin is a competitive binding assay, from which $IC_{50}$ values may be determined. E-selectin/Ig chimera was immobilized in 96 well microtiter plates by incubation at 37° C. for 2 hours. To reduce nonspecific binding, bovine serum albumin was added to each well and incubated at room temperature for 2 hours. The plate was washed and serial dilutions of the test compounds were added to the wells in the presence of conjugates of biotinylated, $sLe^a$ polyacrylamide with streptavidin/horseradish peroxidase and incubated for 2 hours at room temperature.

Figure 5A:
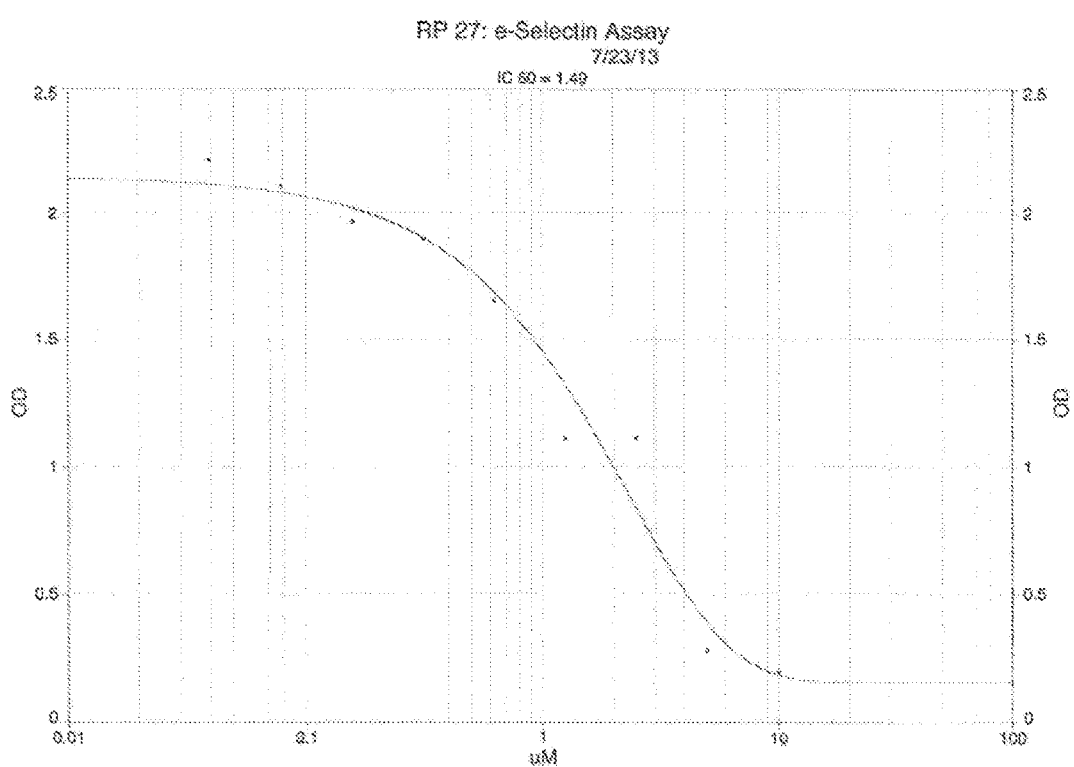
FIG. 5 (FIG. 5A and FIG. 5B) depicts the results of an E-selectin assay in which heterobifunctional Compounds 9 and 16 are used as the inhibitor.
Figure 5B:
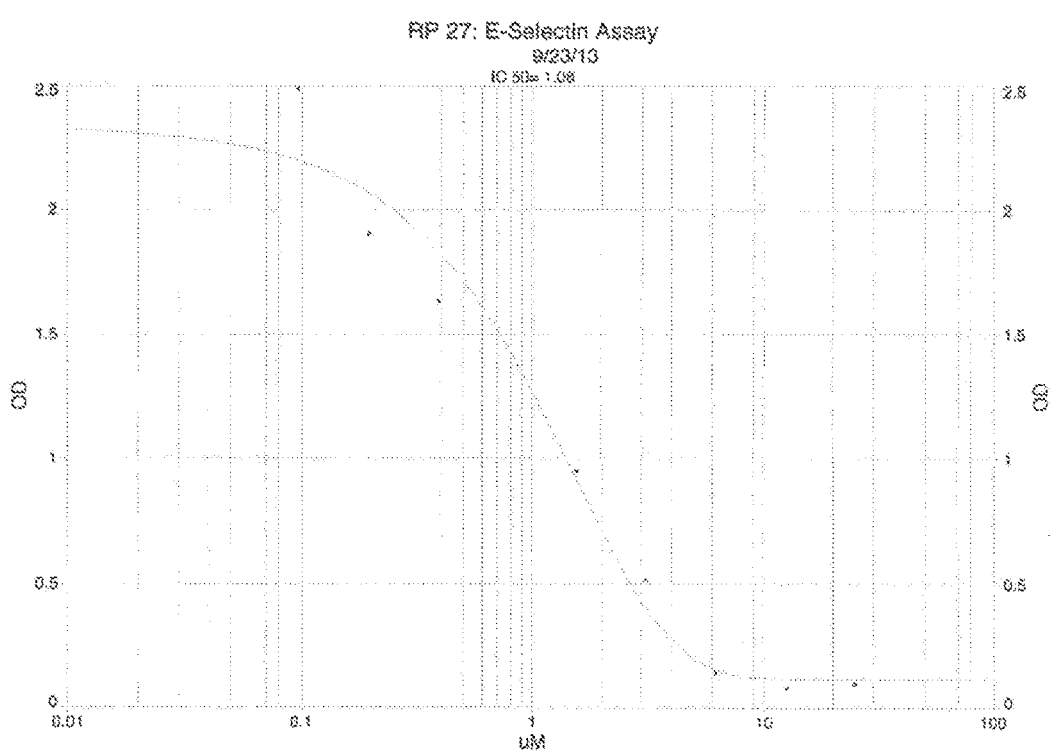

To determine the amount of $sLe^a$ bound to immobilized E-selectin after washing, the peroxidase substrate, 3,3',5,5' tetramethylbenzidine (TMB) was added. After 3 minutes, the enzyme reaction was stopped by the addition of $H_3PO_4$, and the absorbance of light at a wavelength of 450 nm was determined. The concentration of test compound required to inhibit binding by 50% was determined and reported as the $IC_{50}$ value for each E-selectin antagonist as shown in the table below. $IC_{50}$ values for exemplary compounds disclosed herein are provided in the following table. See FIG. 5.

E-Selectin Antagonist Activity of Heterobifunctional Compounds

| Compound | IC50 (μM) | rIC50 |
| --- | --- | --- |
| Compound 9 | 1.49 | 0.60 |
| Compound 16 | 1.08 | 0.23 |

Example 4

CXCR4 Assay—Inhibition of Cyclic AMP

Figure 6:
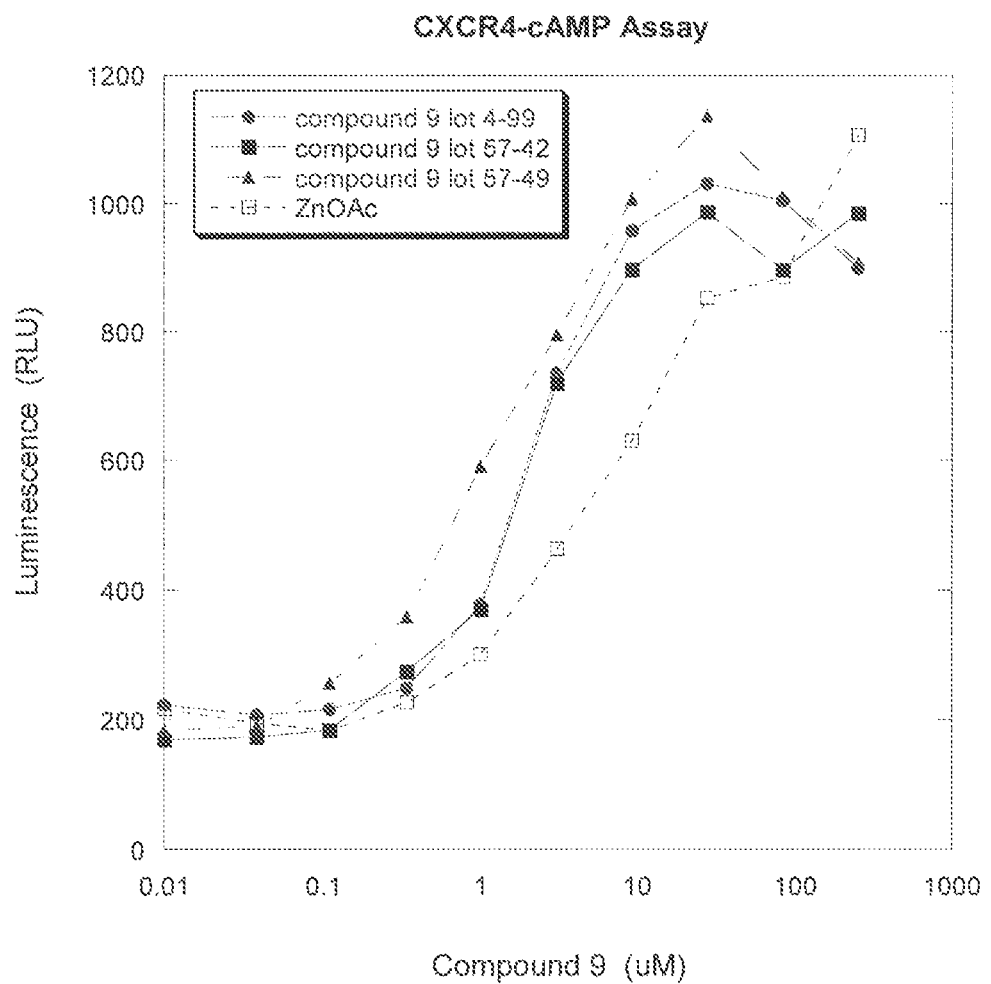
FIG. 6 depicts the results of a CXCR4 assay by heterobifunctional Compound 9.

The CXCR4-cAMP assay measures the ability of a CXCR4 antagonist to inhibit the binding of CXCL12 (SDF- 1α) to CHO cells that have been genetically engineered to express CXCR4 on the cell surface. Assay kits may be purchased from DiscoveRx (95-0081E2CP2M; cAMP Hunter eXpress CXCR4 CHO-K1). The $G_i$-coupled receptor antagonist response protocol described in the kit instruction manual was followed. GPCRs, such as CXCR4, are typically coupled to one of the 3 G-proteins: Gs, Gi or Gq. In the CHO cells supplied with the kit, CXCR4 is coupled to Gi. After activation of CXCR4 by ligand binding (CXCL12), Gi dissociates from the CXCR4 complex, becomes activated, and binds to adenylyl cyclase, thus inactivating it, resulting in decreased levels of intracellular cAMP. Intracellular cAMP is usually low, so the decrease of the low level of cAMP by a Gi-coupled receptor will be hard to detect. Forskolin is added to the CHO cells to directly activate adenylyl cyclase (bypassing all GPCRs), thus raising the level of cAMP in the cell, so that a Gi response can be easily observed. CXCL12 interaction with CXCR4 decreases the intracellular level of cAMP and inhibition of CXCL12 interaction with CXCR4 by a CXCR4 antagonist increases the intracellular cAMP level, which is measured by luminescence. See FIG. 6.

Example 5

Figure 7:
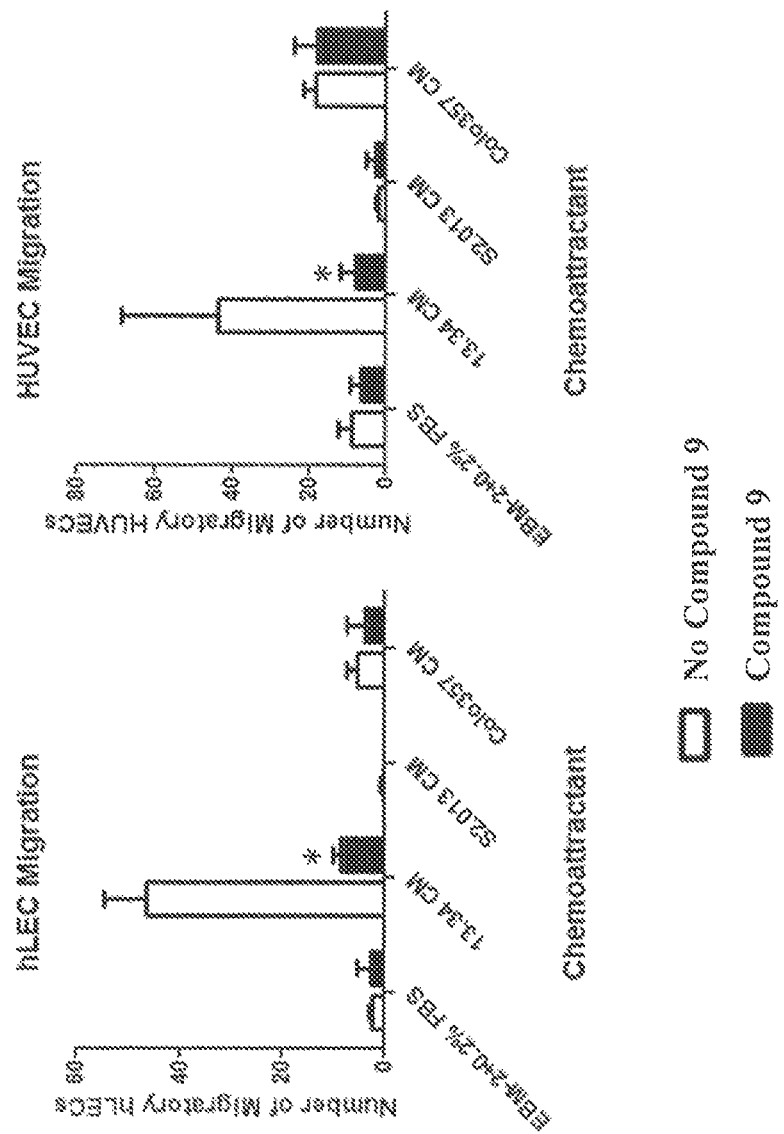
FIG. 7 depicts the results of a lymphatic and vacular endothelial migration toward tumor-associated fibroblasts assay by heterobifunctional Compound 9.

Inhibition of Lymphatic and Vascular Endothelial Migration Toward Tumor-Associated Fibroblasts Plated $8.0 \times 10^5$ 13.34 fibroblasts, S2.013 tumor cells, and Colo357 tumor cells in a T-25. Incubated overnight. Changed media to serum-free EBM-2 and allowed cells to condition media for 24 hours. Collected media and filtered to remove debris. Added 750 ul conditioned media to lower wells of a Boyden chamber migration plate (3 replicate/cell type/treatment). Plated specifications: 24 well; 8.0 um pores. Added $3.0 \times 10_4$ hLECs or HUVECs to the upper wells of the Boyden chamber diluted in serum-free EBM-2 (500 ul/insert). Added 100 ug/ml compound 9 to upper wells. Allowed hLECs or HUVECs to migrate overnight. After migration, washed inserts and removed non-migrated cells on the upper side of the membrane with a Q-tip. Fixed and stained migrated cells with Diff-Quik Kit. Removed membranes from the inserts and mounted on a slide. Drew quadrants over the membranes and imaged each quadrant. Quantified the number of migratory endothelial cells. See FIG. 7.

Example 6

Inhibition of PDAC Cell Binding to Lymphatic Monolayers

Figure 8:
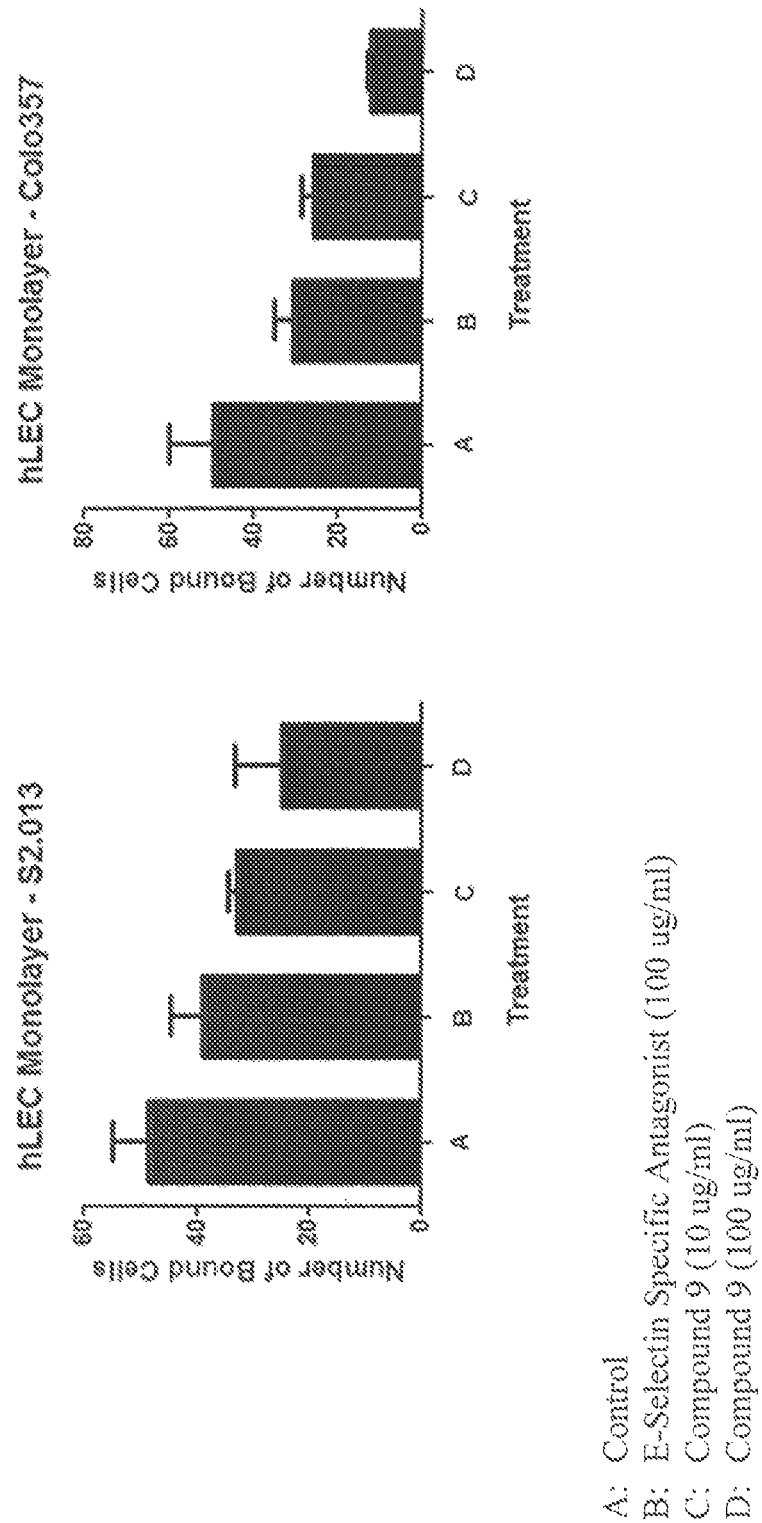
FIG. 8 depicts the results of a PDAC cell binding to lymphatic monolayers assay by heterobifunctional Compound 9.

Plated $4.5 \times 10^4$ hLECs into the wells of 8-well chamber slides. Incubated cells until a confluent monolayer of endothelial cells is achieved. Pretreated the endothelial cells for 2 hours with designated treatments: control media, 100 ug/ml an E-selectin specific antagonist, 10 ug/ml compound 9, or 100 ug/ml compound 9. Dyed S2.013 or Colo357 with CFDA-SE Cell Tracker Dye. Following endothelial cell pretreatment, added $3.0 \times 10^4$ S2.013 or Colo357 cells diluted in serum-free EBM-2 to the wells along with designated treatments (400 ul/well; 3 replicate wells/treatment). Incubated the tumor cells on the endothelial monolayer for 1 hour. Following binding incubation, washed each well 3X with PBS+0.5% FBS to remove non-adherent cells. Fixed with 4% PFA and coverslip slides. Imaged 5 locations/well at 10× magnification. Quantified the number of adherent cells in each image. See FIG. 8.

Example 7

Prostate Cancer Model

Luciferase transfected PC3Luc cells were injected at $2 \times 105$ cells/10 µl of serum-free medium into the proximal tibiae of 4-week old male CD1 nu/nu mice. The development of metastases was monitored by using a Faxitron cabinet x-ray system and tumor burden evaluated by bioluminescence analyses (see below). The development of metastases was monitored by radiography using a Faxitron cabinet x-ray system (Faxitron x-ray corp., Wheeling, Ill., USA). Radiographic analyses were performed at days 28, 35, 42 and 50 after cell injection. No Faxitron analysis was performed after the 50th day since after this time the estimated risk of anesthesia-related mortality of mice was significantly increased. However, in order to determine both cumulative incidence of bone metastases and disease free survival (DSF), Xrays were also repeated at the death of each animal or in the survived animal at the end of follow-up, that we have defined to be 170 days, when animals were sacrificed. Burden of osteolytic lesions was evaluated by digital examination of radiography (ImageJ, a public domain software by Wayne Rasband, NIH, USA). Animals were sacrificed by carbon dioxide inhalation 170 days after heart injections, or earlier if there were early signs of serious distress. All animals were subjected to an accurate post mortem examination and samples of various organs were processed for routine histological analyses.

For luminescence imaging, mice received 150 mg firefly luciferase (Synchem Ug and Co.KG, Felsberg-Altenburg, Germany) per kg body weight given intraperitoneally. Following anesthesia with ketamine/xylazine mixture mice were placed into a Hamamatsu imaging station (Hamamatsu photonics, Italian distributor, Rome Italy). Bioluminescence generated by the luciferin/luciferase reaction was used for quantification using a dedicated Living Image software on a red (high intensity/cell number) to blue (low intensity/cell number) visual scale. A digital grayscale animal image was acquired followed by acquisition and overlay of a pseudo-color image representing the spatial distribution of detected photon counts emerging from active luciferase within the animal. Signal intensity was quantified as the sum of all detected photons within the region of interest during a 1-minute luminescent integration time. Tumor incidence was scored on a dichotomous scale as being either positive or negative if animals had at least one lesion detected in either the humeri or tibia/femur region. See FIG. 9.

The various embodiments described above can be combined to provide further embodiments. All U.S. patents, U.S. patent application publications, U.S. patent applications, non-U.S. patents, non-U.S. patent applications, and non-patent publications referred to in this specification and/or listed in the Application Data Sheet are incorporated herein by reference, in their entirety. Aspects of the embodiments can be modified, if necessary, to employ concepts of the various patents, applications, and publications to provide yet further embodiments.

What is claimed is:

1. At least one compound chosen from compounds of Formula (I):

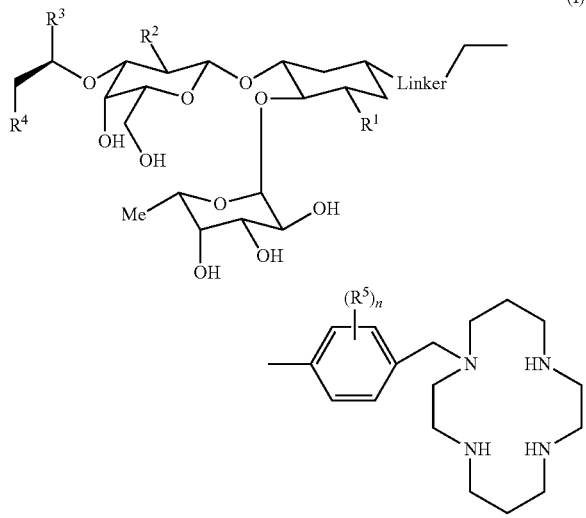

and pharmaceutically acceptable salts thereof, wherein
$R^1$ is chosen from H, $C_{1-8}$ alkyl, $C_{2-8}$ alkenyl, $C_{2-8}$ alkynyl, $C_{1-8}$ haloalkyl, $C_{2-8}$ haloalkenyl, and $C_{2-8}$ haloalkynyl groups;
$R^2$ is chosen from —OH, —NH$_2$, —OC(=O)Y$^1$, —NHC(=O)Y$^1$, and —NHC(=O)NHY$^1$ groups, wherein Y$^1$ is chosen from $C_{1-8}$ alkyl, $C_{2-8}$ alkenyl, $C_{2-8}$ alkynyl, $C_{1-8}$ haloalkyl, $C_{2-8}$ haloalkenyl, $C_{2-8}$ haloalkynyl, $C_{6-18}$ aryl, and $C_{1-13}$ heteroaryl groups;
$R^3$ is chosen from —CN, —CH$_2$CN, and —C(=O)Y$^2$ groups, wherein Y$^2$ is chosen from $C_{1-8}$ alkyl, $C_{2-8}$ alkenyl, $C_{2-8}$ alkynyl, —OZ$^1$, —NHOH, —NHOCH$_3$, —NHCN, and —NZ$^1$Z$^2$ groups, wherein Z$^1$ and Z$^2$, which may be identical or different, are independently chosen from H, $C_{1-8}$ alkyl, $C_{2-8}$ alkenyl, $C_{2-8}$ alkynyl, $C_{1-8}$ haloalkyl, $C_{2-8}$ haloalkenyl, and $C_{2-8}$ haloalkynyl groups, wherein Z$^1$ and Z$^2$ may join together to form a ring;
$R^4$ is chosen from $C_{3-8}$ cycloalkyl groups;
each $R^5$ is independently chosen from H, halo, $C_{1-8}$ alkyl, $C_{2-8}$ alkenyl, $C_{2-8}$ alkynyl, $C_{1-8}$ haloalkyl, $C_{2-8}$ haloalkenyl, and $C_{2-8}$ haloalkynyl groups, with the proviso that at least one $R^5$ is not H;
n is chosen from integers ranging from 1 to 4; and Linker is chosen from linker groups.

2. The at least one compound according to claim 1, wherein $R^1$ is chosen from $C_{1-8}$ alkyl groups.

3. The at least one compound according to claim 2, wherein $R^1$ is chosen from ethyl and methyl.

4. The at least one compound according to claim 3, wherein $R^1$ is ethyl.

5. The at least one compound according to claim 1, wherein $R^2$ is chosen from —OH, —NH$_2$, —OC(=O)Y$^1$, and —NHC(=O)Y$^1$, wherein Y$^1$ is chosen from $C_{1-8}$ alkyl, $C_{6-18}$ aryl, and $C_{1-13}$ heteroaryl groups.

6. The at least one compound according to claim 5, wherein $R^2$ is chosen from

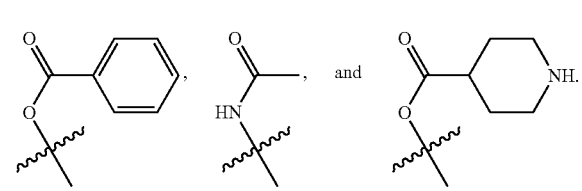

7. The at least one compound according to claim 1, wherein $R^3$ is chosen from —C(=O)Y$^2$, wherein Y$^2$ is chosen from —OZ$^1$, —NHOH, —NHOCH$_3$, and —NZ$^1$Z$^2$ groups, wherein Z$^1$ and Z$^2$, which may be identical or different, are independently chosen from H, and $C_{1-8}$ alkyl, wherein Z$^1$ and Z$^2$ may join together to form a ring.

8. The at least one compound according to claim 7, wherein $R^3$ is —C(=O)OH.

9. The at least one compound according to claim 1, wherein $R^4$ is chosen from

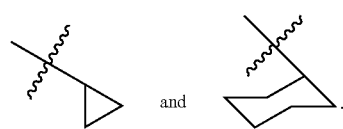

10. The at least one compound according to claim 1, wherein at least one $R^5$ is halo.

11. The at least one compound according to claim 10, wherein at least one $R^5$ is Bromo.

12. The at least one compound according to claim 10, wherein n is 1.

13. The at least one compound according to claim 1, wherein the at least one compound is chosen from compounds of Formula (Ia):

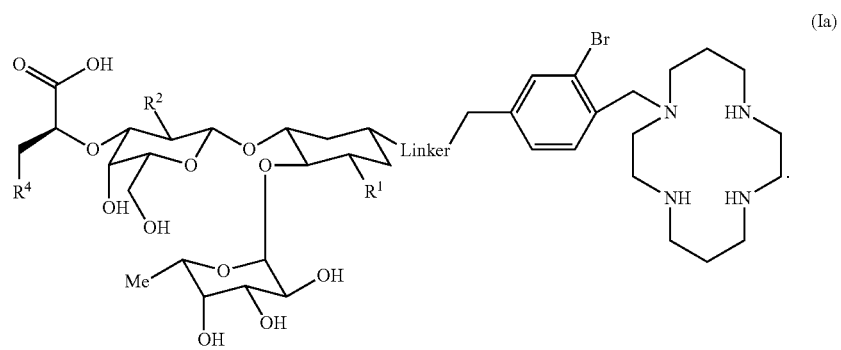

14. The at least one compound according to claim 1, wherein the at least one compound is chosen from compounds of Formula (Ib):
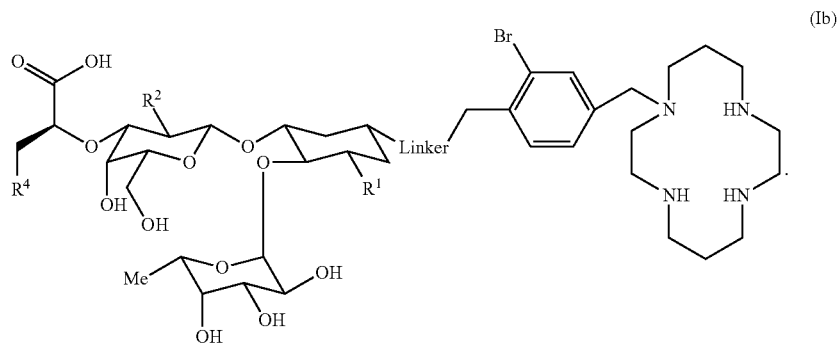
(Ib)
15. The at least one compound according to claim 13, wherein the at least one compound is chosen from the following Formulae:
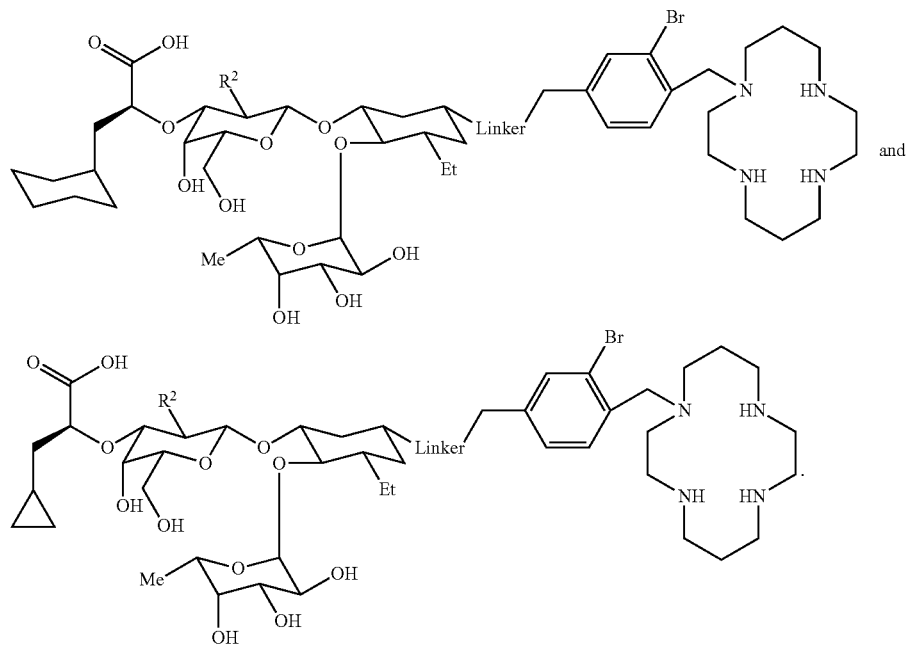
and
16. The at least one compound according to claim 14, wherein the at least one compound is chosen from the following Formulae:
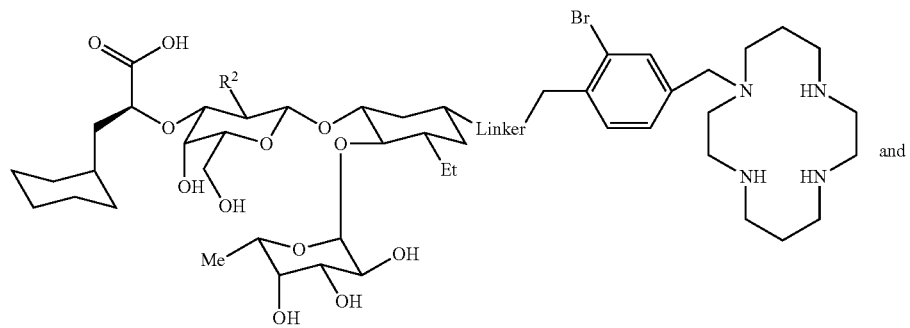
and

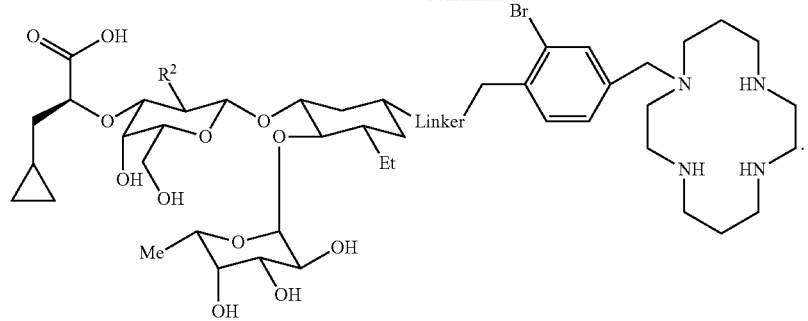
17. The at least one compound according to claim 1, wherein the at least one compound is chosen from the following Formulae:
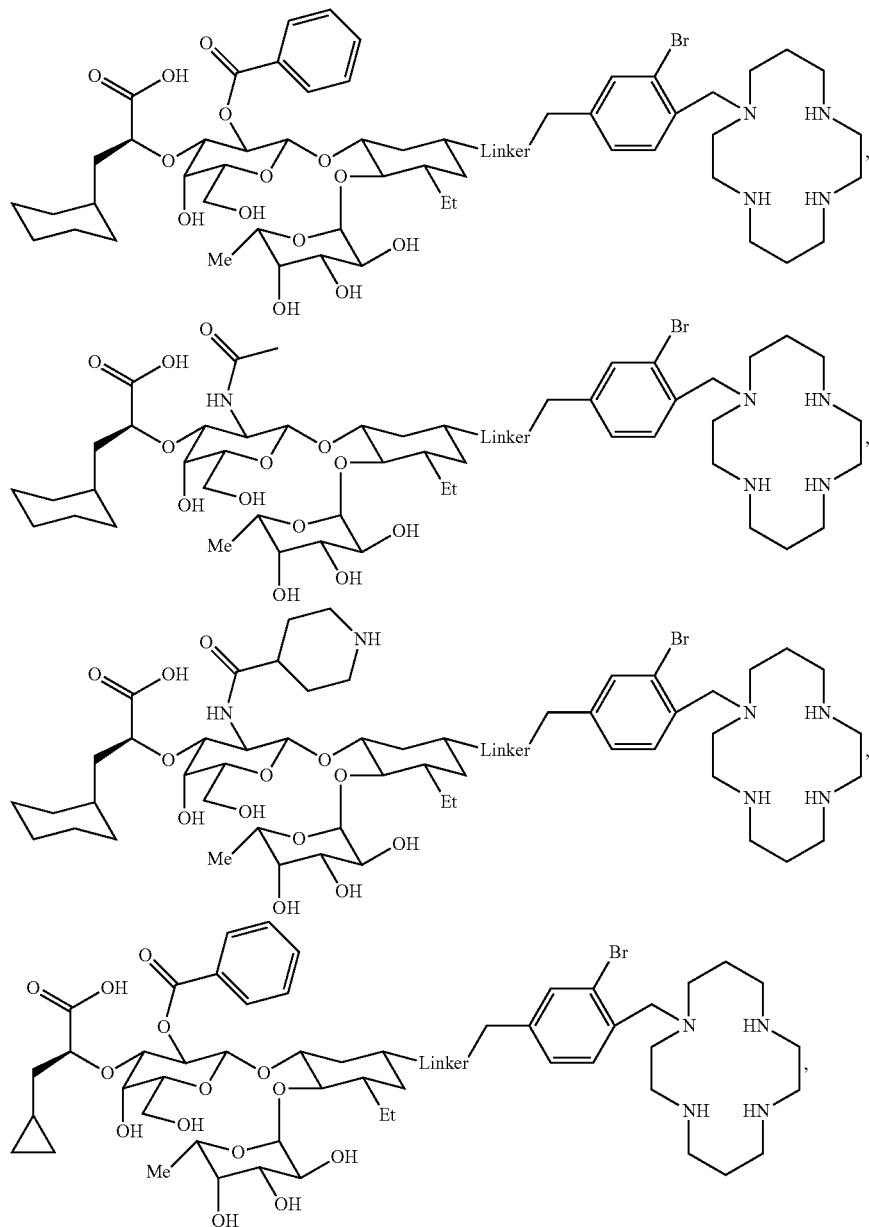

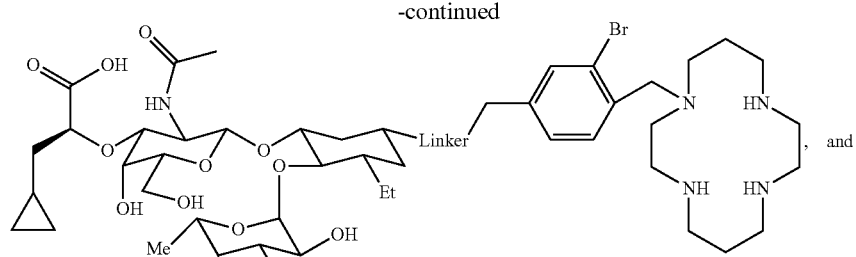
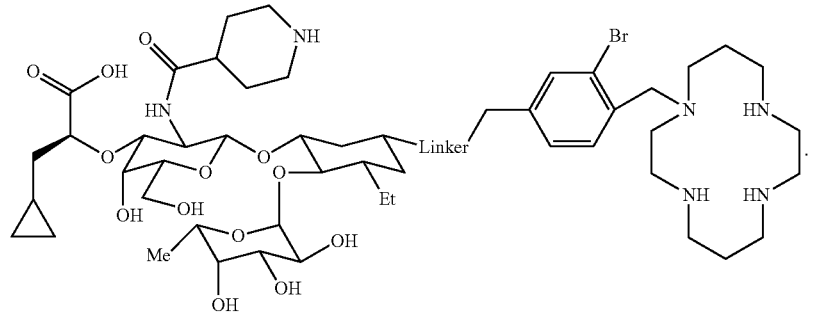
18. The at least one compound according to claim 1, wherein the at least one compound is chosen from the following Formulae:
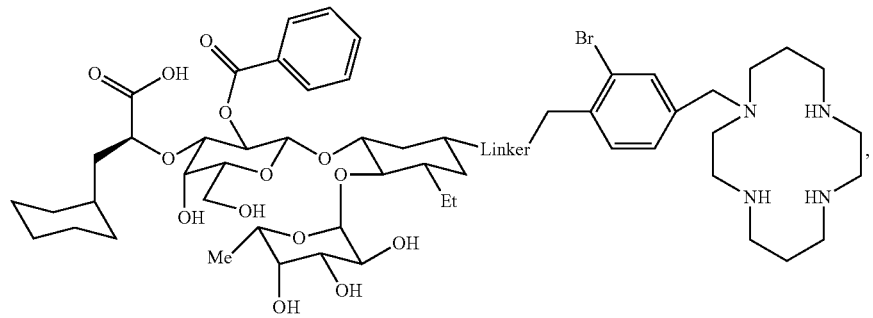
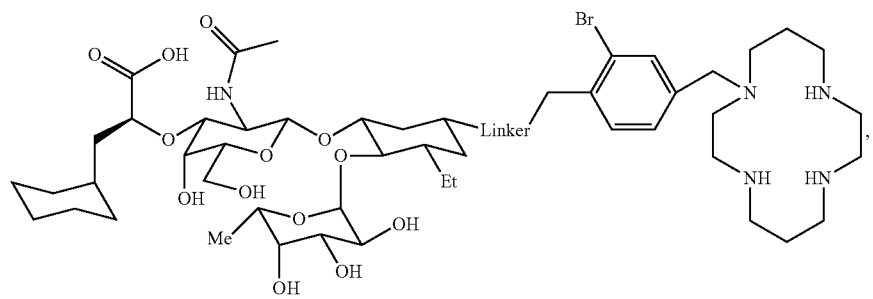
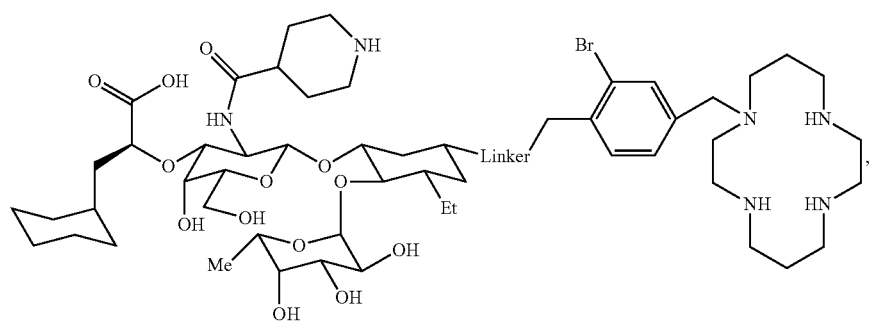

-continued

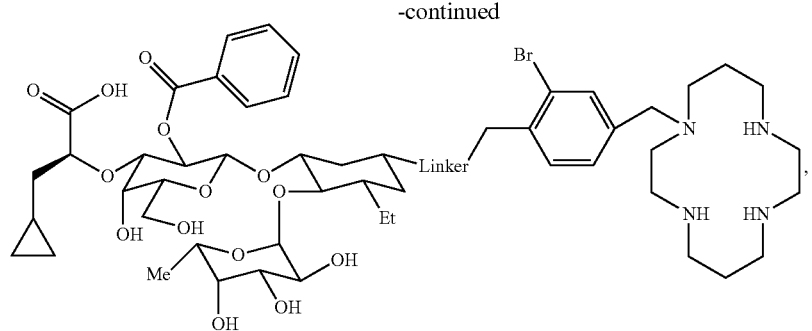

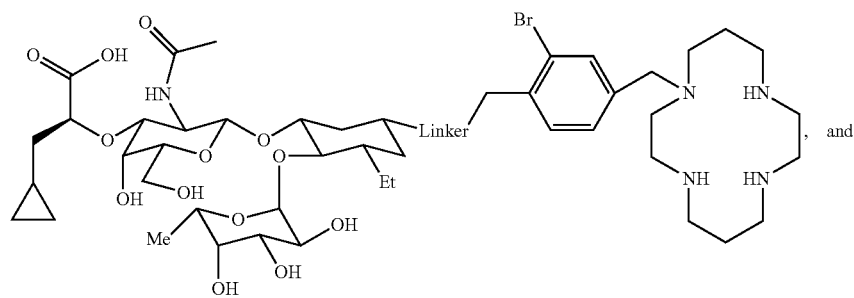

, and

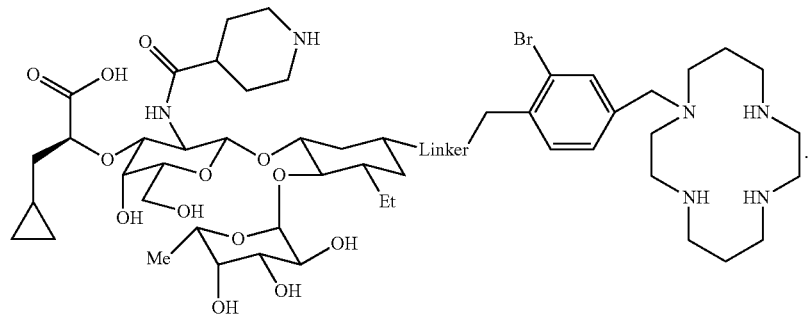

.

19. The at least one compound according to claim 1, wherein the linker group is —C(=O)NH(CH$_2$)$_2$NH—.

20. The at least one compound according to claim 1, wherein the linker group is —CH$_2$NHCH$_2$—.

21. The at least one compound according to claim 1, wherein the linker group is —C(=O)NHCH$_2$—.

22. The at least one compound according to claim 1, wherein the at least one compound is chosen from the following Formulae:

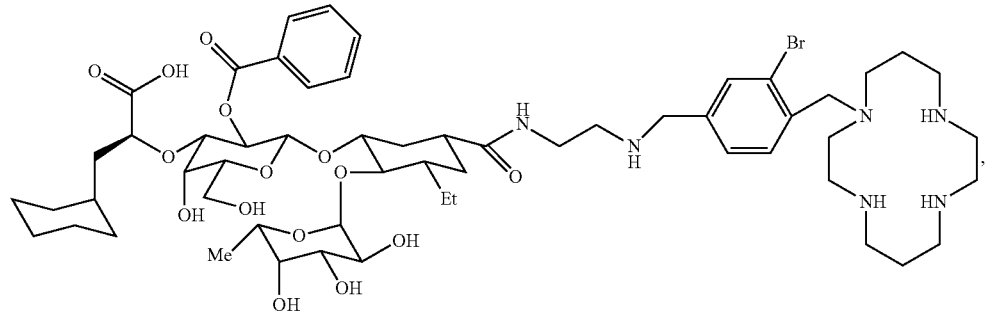

,

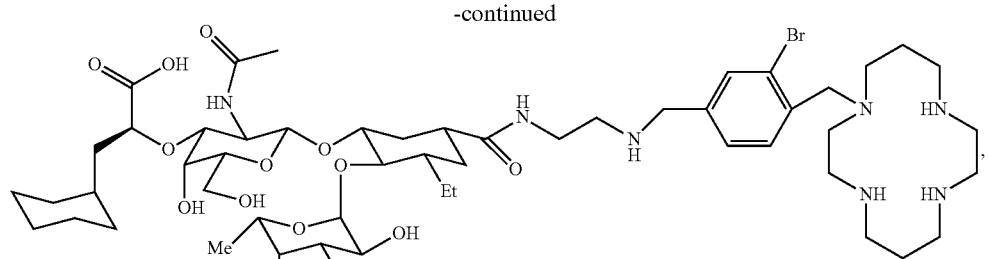
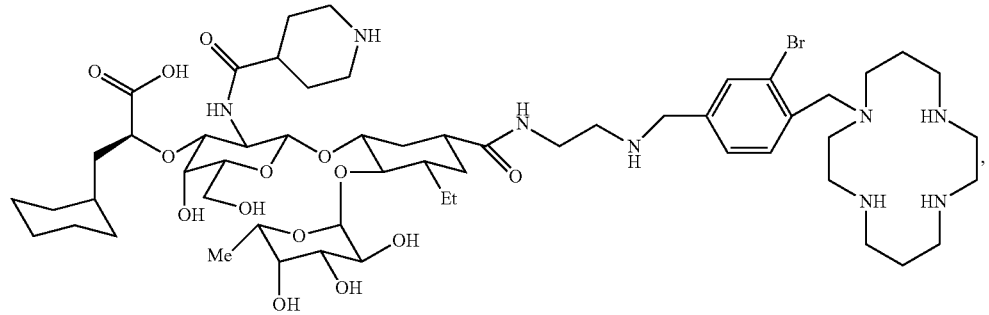
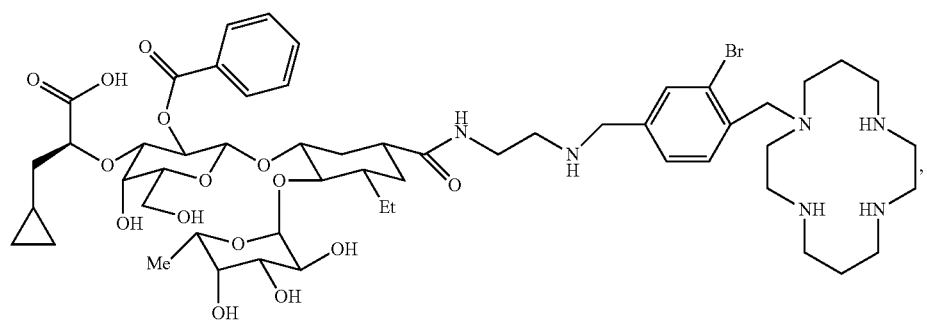
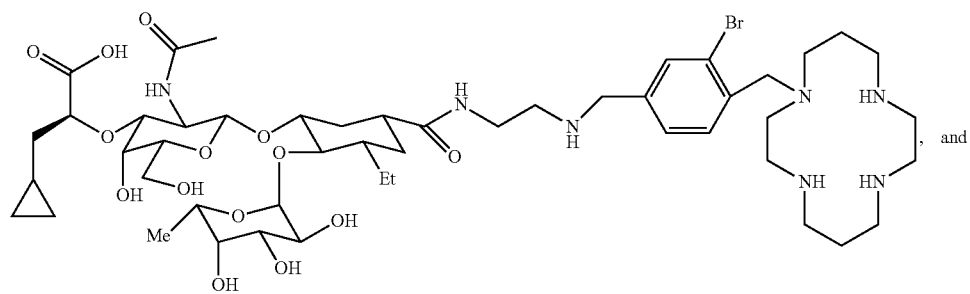
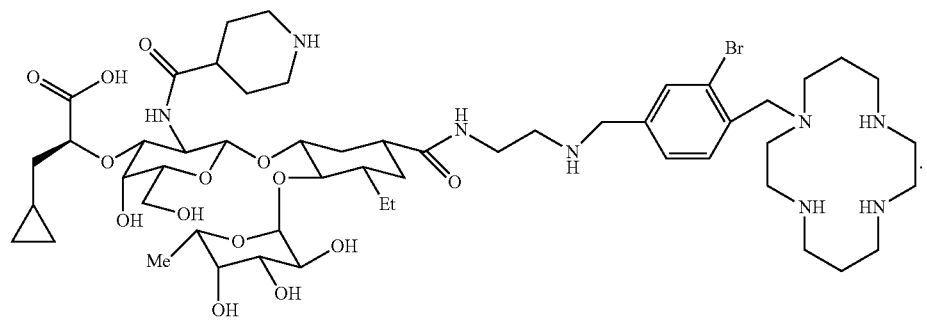

23. The at least one compound according to claim 1, wherein the at least one compound is chosen from the following Formulae:
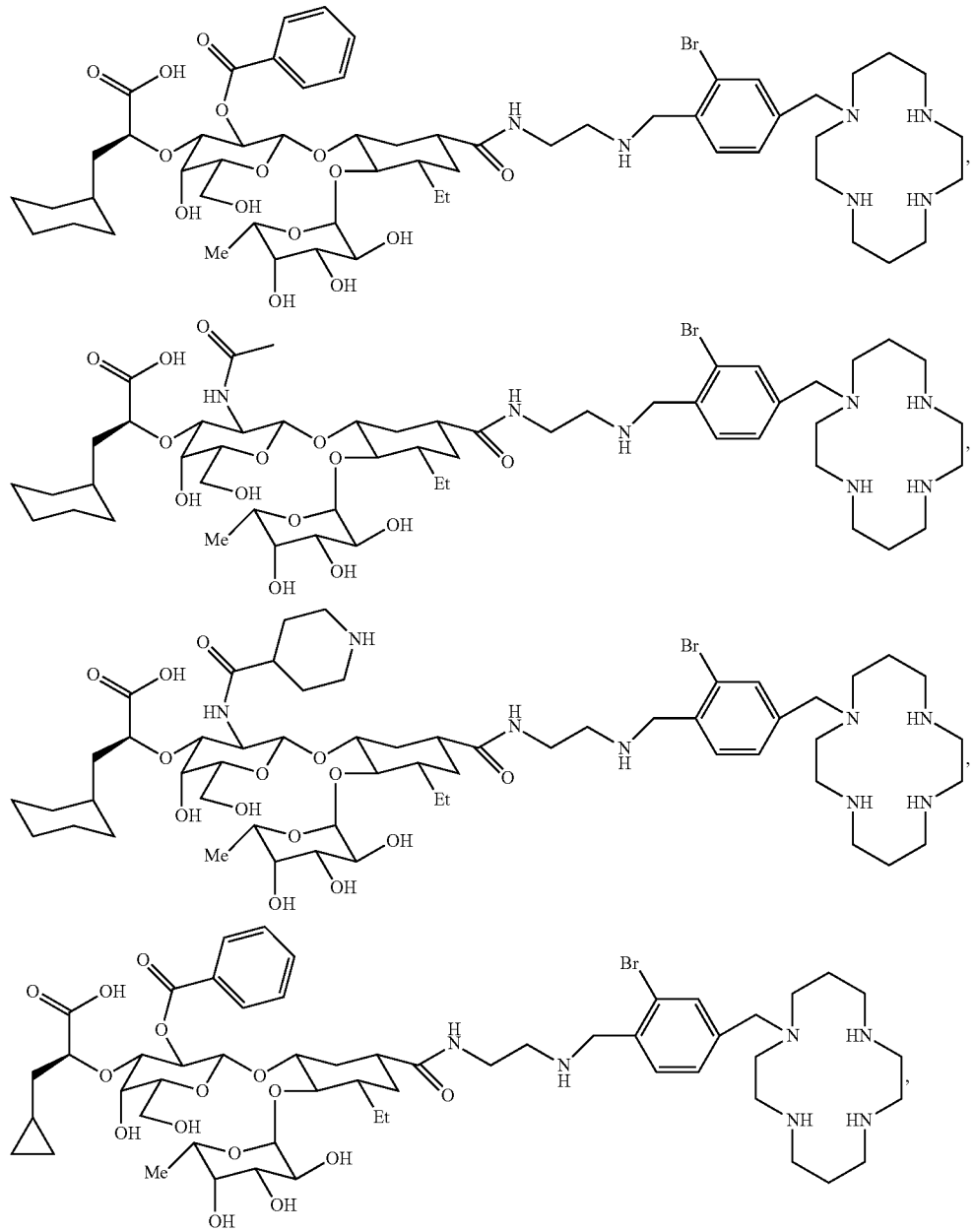
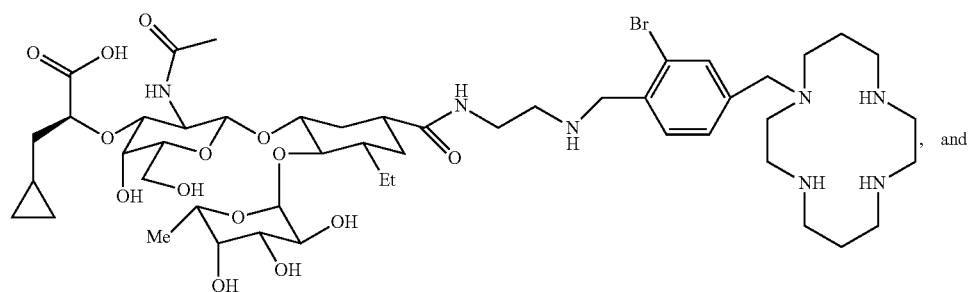

-continued

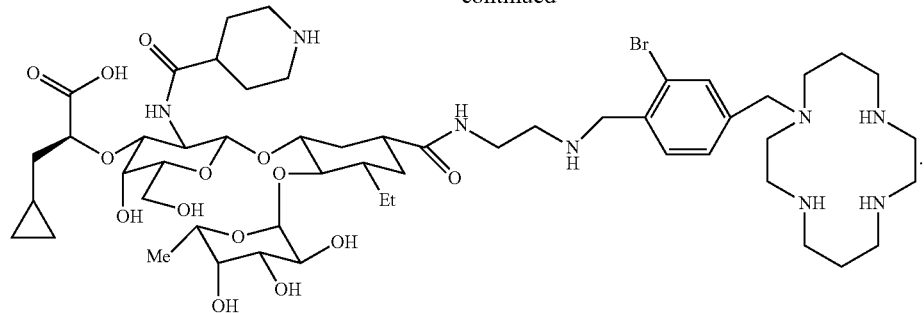

24. The at least one compound according to claim 1, wherein the at least one compound is

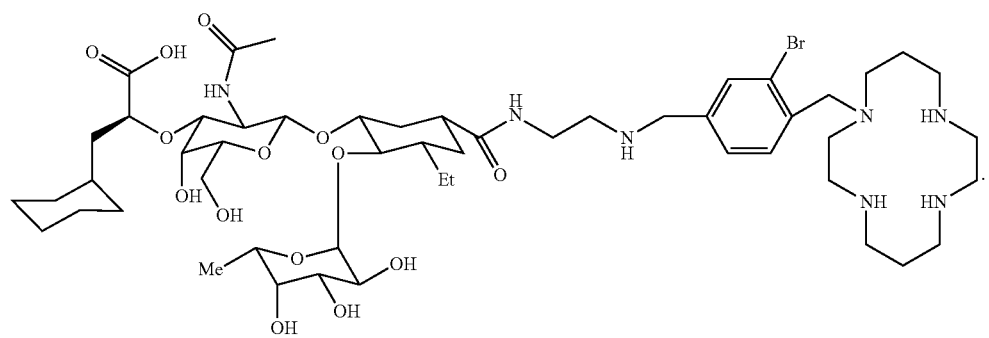 [SMILES: CCC1CC(C(=O)NCCNCc2ccc(CN3CCCNCCNCCCNCC3)c(Br)c2)CC(OC2OC(CO)C(O)C(O[C@@H](CC3CCCCC3)C(=O)O)C2NC(C)=O)C1OC1OC(C)C(O)C(O)C1O]

25. The at least one compound according to claim 1, wherein the at least one compound is

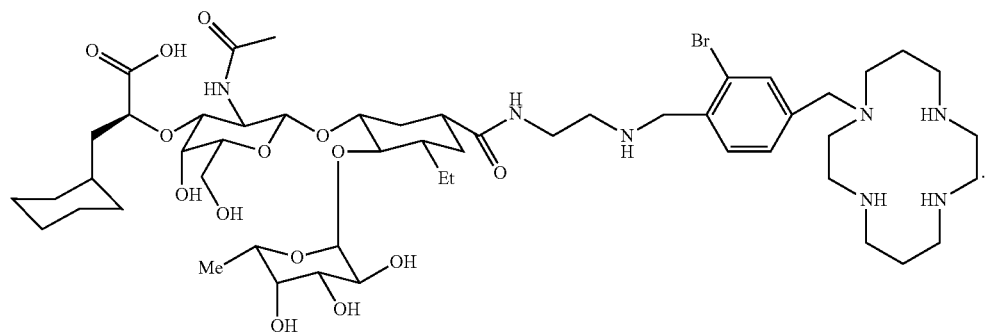 [SMILES: CCC1CC(C(=O)NCCNCc2ccc(CN3CCCNCCNCCCNCC3)cc2Br)CC(OC2OC(CO)C(O)C(O[C@@H](CC3CCCCC3)C(=O)O)C2NC(C)=O)C1OC1OC(C)C(O)C(O)C1O]

26. A composition comprising at least one compound of claim 1 and at least one additional pharmaceutically acceptable ingredient.

27. A method for the treatment of a cancer in which the cancer cells may leave the primary site comprising administering to a subject in need thereof an effective amount of at least one compound of claim 1 and optionally at least one additional pharmaceutically acceptable ingredient.

28. A method for the treatment of a cancer in which it is desired to mobilize cancer cells from a site into the bloodstream and retain the cancer cells in the bloodstream comprising administering to a subject in need thereof an effective amount of at least one compound of claim 1 and optionally at least one additional pharmaceutically acceptable ingredient.

29. A method for releasing cells into circulating blood and enhancing retention of the cells in the blood comprising administering to a subject in need thereof an effective amount of at least one compound of claim 1 and optionally at least one additional pharmaceutically acceptable ingredient.

30. A method for the treatment of tumor metastasis comprising administering to a subject in need thereof an effective amount of at least one compound of claim 1 and optionally at least one additional pharmaceutically acceptable ingredient.

31. A method for the treatment of an inflammatory disease in which the adhesion or migration of cells occurs in the disease comprising administering to a subject in need thereof an effective amount of at least one compound of claim 1 and optionally at least one additional pharmaceutically acceptable ingredient.

* * * * *

UNITED STATES PATENT AND TRADEMARK OFFICE
CERTIFICATE OF CORRECTION

| | |
|---|---|
| PATENT NO. | : 10,519,181 B2 |
| APPLICATION NO. | : 15/531951 |
| DATED | : December 31, 2019 |
| INVENTOR(S) | : John L. Magnani et al. |

It is certified that error appears in the above-identified patent and that said Letters Patent is hereby corrected as shown below:

In the Specification

Column 3, Line 45, "emobidments" should read --embodiments--.
Column 3, Line 61, "emobdiments" should read --embodiments--.
Column 6, Line 62, "iode" should read --iodo--.
Column 16, Line 43, "Formulas" should read --Formulae--.
Column 21, Line 57, "cush" should read --such--.
Column 22, Line 7, "cells" should read --cell--.
Column 22, Line 48, "emobidments" should read --embodiments--.
Column 23, Line 39, "bonds" should read --bond--.
Column 23, Line 43, "butyryl" should read --butynyl--.
Column 23, Line 66, "group" should read --groups--.
Column 24, Line 8, "car" should read --or--.
Column 34, Line 9, "CO2" should read --$CO_2$--.
Column 39, Line 65, "temperature 4.5 h" should read --temperature for 4.5 h--.
Column 39, Line 67 to Column 40, Line 1, "with washed" should read --washed with--.
Column 40, Line 10, "1, 2-dichloroethane, 40 ml)" should read --1,2-dichloroethane (40 ml)--.
Column 40, Line 39, "dissolve" should read --dissolved--.
Column 40, Line 44, "$CHCl_3$ (100 ml), (250 ml)" should read --$CHCl_3$ (100 ml), $H_2O$ (250 ml)--.
Column 40, Line 57, "dissolve" should read --dissolved--.
Column 41, Line 3, "chlorochomate" should read --chlorochromate--.
Column 41, Line 14, "turn" should read --turned--.
Column 41, Line 23-24, "stirred room temperature for overnight" should read --stirred at room temperature overnight--.
Column 41, Line 34, "(Na2SO4)" should read --$(Na_2SO_4)$--.
Column 41, Line 57, "adjusted 9.5" should read --adjusted to 9.5--.
Column 42, Line 14, "place" should read --placed--.
Column 43, Line 37, "$3.0 \times 10_4$" should read --$3.0 \times 10^4$--.

Signed and Sealed this
Second Day of August, 2022

Katherine Kelly Vidal
*Director of the United States Patent and Trademark Office*

CERTIFICATE OF CORRECTION (continued)
U.S. Pat. No. 10,519,181 B2

In the Claims

Claim 1, Column 45, Lines 5-25, Formula (I),

" 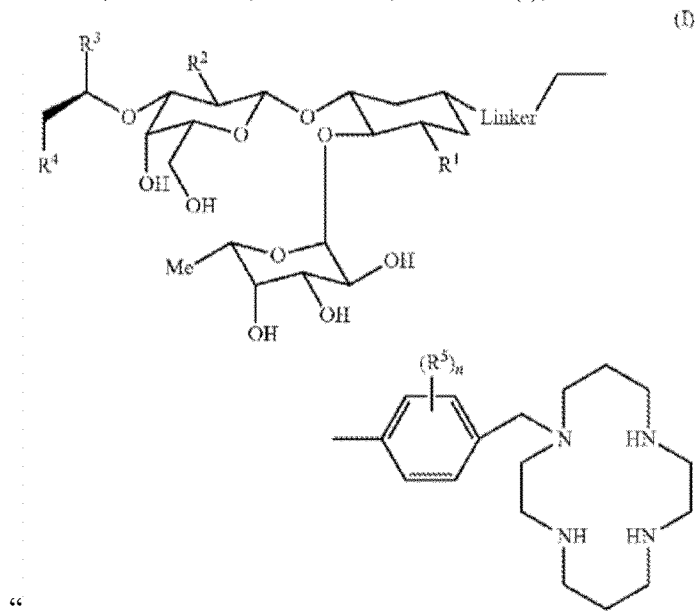 " should read as

-- 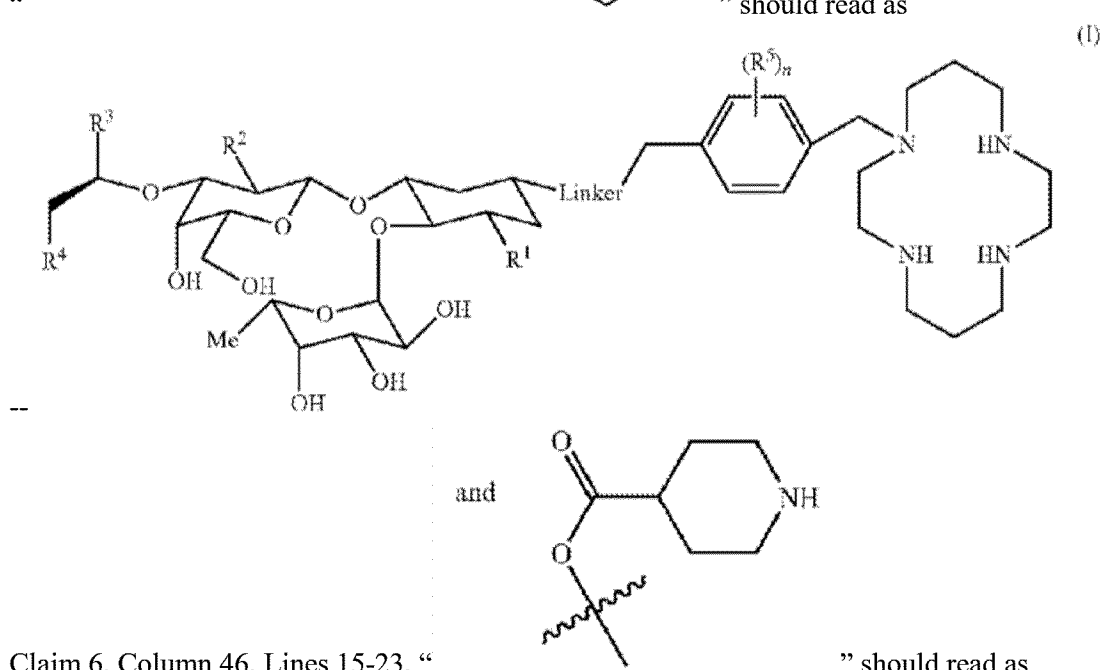 --.

Claim 6, Column 46, Lines 15-23, " 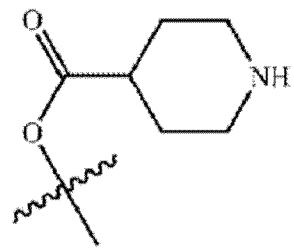 " should read as

--and 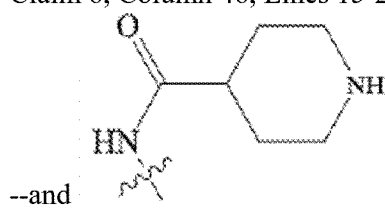 --.

Claim 11, Column 46, Line 44, "Bromo" should read --bromo--.